(12) United States Patent
Tsai et al.

(10) Patent No.: US 10,485,790 B1
(45) Date of Patent: Nov. 26, 2019

(54) SALTS OF CYCLOSERINE COMPOUNDS AND APPLICATIONS THEREOF

(71) Applicant: SyneuRx International (Taiwan) Corp., New Taipei (TW)

(72) Inventors: Guochuan Emil Tsai, Pasadena, CA (US); Ching-Cheng Wang, New Taipei (TW); Tsai-Miao Shih, New Taipei (TW)

(73) Assignee: SyneuRx International (Taiwan) Corp., New Taipei (TW)

( * ) Notice: Subject to any disclaimer, the term of this patent is extended or adjusted under 35 U.S.C. 154(b) by 0 days.

(21) Appl. No.: 16/130,836

(22) Filed: Sep. 13, 2018

(51) Int. Cl.
| | |
|---|---|
| A61K 31/42 | (2006.01) |
| A23L 33/10 | (2016.01) |
| A61P 25/28 | (2006.01) |
| A61P 25/22 | (2006.01) |
| A61P 25/18 | (2006.01) |
| A61P 25/24 | (2006.01) |
| A61P 25/16 | (2006.01) |
| A61P 31/06 | (2006.01) |
| A61K 31/194 | (2006.01) |
| A61K 45/06 | (2006.01) |

(52) U.S. Cl.
CPC .............. *A61K 31/42* (2013.01); *A23L 33/10* (2016.08); *A61K 31/194* (2013.01); *A61P 25/16* (2018.01); *A61P 25/18* (2018.01); *A61P 25/22* (2018.01); *A61P 25/24* (2018.01); *A61P 25/28* (2018.01); *A61P 31/06* (2018.01); *A23V 2002/00* (2013.01); *A23V 2200/322* (2013.01); *A61K 45/06* (2013.01); *A61K 2300/00* (2013.01)

(58) Field of Classification Search
None
See application file for complete search history.

(56) References Cited

FOREIGN PATENT DOCUMENTS

CS            119472         *    8/1966

* cited by examiner

*Primary Examiner* — Kristin A Vajda
(74) *Attorney, Agent, or Firm* — Polsinelli P.C.

(57) ABSTRACT

The present invention relates to salts of formula [A][B], wherein [A] is a cation form of a cycloserine compound and [B] is an anion form of a compound of Formula (I):

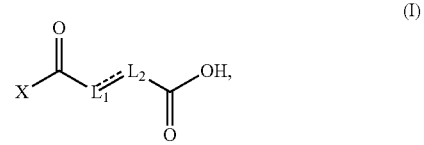

wherein the ratio between the cycloserine compound and the compound of formula (I) ranges from 10:1 to 1:10. The salts described herein have improved properties, including greatly increased stability and decreased hygroscopicity. Also provided in the present invention are methods for treating and/or reducing the risk of a neuropsychiatric disorder and/or a bacterial infectious disease (e.g., tuberculosis), comprising administering a subject in need a composition comprising salts of formula [A][B] described herein.

15 Claims, 42 Drawing Sheets

SALTS OF CYCLOSERINE COMPOUNDS AND APPLICATIONS THEREOF

BACKGROUND OF THE INVENTION

D-Cycloserine (i.e., 4-amino-3-isoxazolidinone), is a natural product of *Streptomyces orchidaceus* and *Streptomyces garyphalus*, which acts as a competitive antagonist of D-alanine, one component of bacterial cell walls. D-cycloserine inhibits alanine racemase and alanine synthetase, accumulation of an incomplete cell wall component results in bacterial cell walls damaging. It has been known as an antibiotic drug since the late 1950s and marketed under a brand name Seromycin®. It was classified on the World Health Organization's List of Essential Medicines as a second-line drug for the treatment of multidrug-resistant tuberculosis (MDR-TB).

In addition, D-cycloserine can penetrate into the central nervous system (CNS), and it has a unique potential to target the glycine-binding site of N-methyl-D-aspartate (NMDA) receptors in humans. As a selective partial NMDA-agonist, it was later proven on slice preparations, that D-cycloserine influences long-term potentiation (LTP), a neuronal mechanism for learning processes. Interestingly, it acts as a positive modulator at the NMDA receptor at low dose, but as a negative modulator at high dose. Therefore, the use of D-cycloserine is limited due to its side effects including headaches, drowsiness, depression, dizziness, vertigo, confusion, paresthesia, dysarthria, hyperirritability, psychosis, convulsions, and shaking (tremors) when the dosing is inappropriate. Meanwhile, overdosing with D-cycloserine may result in paresis, seizures, and coma, in addition, alcohol consumption may increase the risk of seizures as well.

Since LTP is important for cognitive functions, D-cycloserine has been introduced to neuropsychiatric studies, with a proper dosage, to evaluate its therapeutic potentials for neurological and psychiatric conditions such as Alzheimer's disease, schizophrenia, depression, obsessive compulsive disorder, autism, post-traumatic stress disorder and anxiety disorders.

SUMMARY OF THE INVENTION

The present disclosure is based, at least in part, on the finding that salts of cycloserine compounds as disclosed herein have improved qualities, for example, unexpectedly high stability and significantly decreased hygroscopicity.

In one aspect, the present disclosure provides a salt of formula [A][B]. [A] is a cation form of a cycloserine compound; and [B] is an anion form of a compound of formula (I):

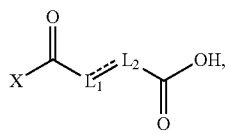

(I)

in which
X is —NH$_2$ or —OH;
each of L$_1$ and L$_2$, independently, is C$_{1-6}$ alkylene, C$_{2-6}$ alkenylene, or C$_{2-6}$ alkynylene, or one of L$_1$ and L$_2$ is N, O, or S, and the other one is C$_{1-6}$ alkylene, C$_{2-6}$ alkenylene, or C$_{2-6}$ alkynylene, as valency permits;
==== is either a single or double bond;
and the ratio between of [A] and [B] in the salt ranges from 10:1 to 1:10.

In another aspect, the present disclosure provides a composition comprising the salt of formula [A][B] as described herein, and a carrier. The composition can be a pharmaceutical composition, a nutraceutical composition, a health food, or a medical food.

In yet another aspect, the present disclosure provides a method for treating a neuropsychiatric disorder or a bacterial infectious disease, the method comprising administering to a subject in need of the treatment an effective amount of the salt of formula [A][B] as disclosed herein. In some embodiments, the subject has, is suspected of having, or at risk for a neuropsychiatric disorder or a bacterial infectious disease (e.g., tuberculosis). Exemplary neuropsychiatric disorders include, but are not limited to, schizophrenia, psychotic disorders, Alzheimer's disease, frontotemporal dementia, vascular dementia, dementia with Lewy bodies, senile dementia, mild cognitive impairment, benign forgetfulness, closed head injury, autistic spectrum disorder, Asperger's disorder, fragile X syndrome, attention deficit hyperactivity disorders, attention deficit disorder, obsessive compulsive disorder, tic disorders, childhood learning disorders, premenstrual syndrome, depression, major depressive disorder, anhedonia, suicidal ideation and/or behaviors, bipolar disorder, anxiety disorders, panic disorder, post-traumatic stress disorder, chronic mild and unpredictable stress, eating disorders, addiction disorders, personality disorders, Parkinson's disorder, Huntington's disorder, multiple sclerosis, amyotrophic lateral sclerosis, ataxia, Friedreich's ataxia, Tourette's syndrome, nocturnal enuresis, non-epileptic seizures, blepharospasm, Duchenne muscular dystrophy, stroke, chronic pain, neuropathic pain including hyperalgesia and allodynia, diabetic polyneuropathy, and chronic pain syndromes.

Also provided herein are pharmaceutical compositions comprising any of the salt of formula [A][B] disclosed herein for use in treating a neuropsychiatric disorder or a bacterial infectious disease such as those disclosed herein, and use of the salt of formula [A][B] for manufacturing a medicament for use in treating the target disease as disclosed herein.

The details of one or more embodiments of the disclosure are set forth herein. Other features, objects, and advantages of the disclosure will be apparent from the Detailed Description, the Examples, and the Claims.

DEFINITIONS

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987. The disclosure is not intended to be limited in any manner by the exemplary listing of substituents described herein.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, NY, 1962); and Wilen, *Tables of Resolving Agents and Optical Resolutions* p. 268 (E. L. Eliel, Ed., Univ. of Notre Dame Press, Notre Dame, Ind. 1972). The disclosure additionally encompasses compounds described herein as individual isomers substantially free of other isomers, and alternatively, as mixtures of various isomers.

When a range of values is listed, it is intended to encompass each value and sub-range within the range. For example, "$C_{1-6}$" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$.

The term "aliphatic" includes both saturated and unsaturated, straight chain (i.e., unbranched), branched, acyclic, cyclic, or polycyclic aliphatic hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, the term "alkyl" includes straight, branched and cyclic alkyl groups. An analogous convention applies to other generic terms such as "alkenyl", "alkynyl", and the like. Furthermore, the terms "alkyl", "alkenyl", "alkynyl", and the like encompass both substituted and unsubstituted groups. In certain embodiments, "lower alkyl" is used to indicate those alkyl groups (cyclic, acyclic, substituted, unsubstituted, branched or unbranched) having 1-6 carbon atoms.

In certain embodiments, the alkyl, alkenyl, and alkynyl groups employed in the disclosure contain 1-20 aliphatic carbon atoms. In certain other embodiments, the alkyl, alkenyl, and alkynyl groups employed in the disclosure contain 1-10 aliphatic carbon atoms. In yet other embodiments, the alkyl, alkenyl, and alkynyl groups employed in the disclosure contain 1-8 aliphatic carbon atoms. In still other embodiments, the alkyl, alkenyl, and alkynyl groups employed in the disclosure contain 1-6 aliphatic carbon atoms. In yet other embodiments, the alkyl, alkenyl, and alkynyl groups employed in the disclosure contain 1-4 carbon atoms. Illustrative aliphatic groups thus include, but are not limited to, for example, methyl, ethyl, n-propyl, isopropyl, cyclopropyl, —$CH_2$-cyclopropyl, vinyl, allyl, n-butyl, sec-butyl, isobutyl, tert-butyl, cyclobutyl, —$CH_2$-cyclobutyl, n-pentyl, sec-pentyl, isopentyl, tert-pentyl, cyclopentyl, —$CH_2$-cyclopentyl, n-hexyl, sec-hexyl, cyclohexyl, —$CH_2$-cyclohexyl moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl, and the like.

The term "alkyl" refers to a radical of a straight-chain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), propyl ($C_3$) (e.g., n-propyl, isopropyl), butyl ($C_4$) (e.g., n-butyl, tert-butyl, sec-butyl, iso-butyl), pentyl ($C_5$) (e.g., n-pentyl, 3-pentanyl, amyl, neopentyl, 3-methyl-2-butanyl, tertiary amyl), and hexyl ($C_6$) (e.g., n-hexyl). Additional examples of alkyl groups include n-heptyl ($C_7$), n-octyl ($C_8$), and the like. Unless otherwise specified, each instance of an alkyl group is independently unsubstituted (an "unsubstituted alkyl") or substituted (a "substituted alkyl") with one or more substituents (e.g., halogen, such as F). In certain embodiments, the alkyl group is an unsubstituted $C_{1-10}$ alkyl (such as unsubstituted $C_{1-6}$ alkyl, e.g., —$CH_3$). In certain embodiments, the alkyl group is a substituted $C_{1-10}$ alkyl (such as substituted $C_{1-6}$ alkyl, e.g., —$CF_3$).

"Alkenyl" refers to a radical of a straight-chain or branched hydrocarbon group having from 2 to 20 carbon atoms, one or more carbon-carbon double bonds, and no triple bonds ("$C_{2-20}$ alkenyl"). In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently optionally substituted, i.e., unsubstituted (an "unsubstituted alkenyl") or substituted (a "substituted alkenyl") with one or more substituents. In certain embodiments, the alkenyl group is unsubstituted $C_{2-10}$ alkenyl. In certain embodiments, the alkenyl group is substituted $C_{2-10}$ alkenyl. In an alkenyl group, a C=C double bond for which the stereochemistry is not specified (e.g., —CH=CHCH$_3$ or

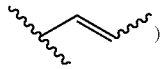)

may be an (E)- or (Z)-double bond.

"Alkynyl" refers to a radical of a straight-chain or branched hydrocarbon group having from 2 to 20 carbon atoms, one or more carbon-carbon triple bonds, and optionally one or more double bonds ("$C_{2-20}$ alkynyl"). In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently optionally substituted, i.e., unsubstituted (an "unsubstituted alkynyl") or substituted (a "substituted alkynyl") with one or more substituents. In certain embodiments, the alkynyl group is unsubstituted $C_{2-10}$ alkynyl. In certain embodiments, the alkynyl group is substituted $C_{2-10}$ alkynyl.

Alkyl, alkenyl, and alkynyl groups, which are divalent bridging groups, are further referred to using the suffix -ene, e.g., alkylene, alkenylene, and alkynylene.

An atom, moiety, or group described herein may be unsubstituted or substituted, as valency permits, unless otherwise provided expressly. The term "optionally substituted" refers to substituted or unsubstituted.

A group is optionally substituted unless expressly provided otherwise. The term "optionally substituted" refers to being substituted or unsubstituted. In certain embodiments, alkyl, alkenyl, alkynyl, carbocyclyl, heterocyclyl, aryl, and heteroaryl groups are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present disclosure contemplates any and all such combinations in order to arrive at a stable compound. For purposes of this disclosure, heteroatoms such as nitrogen may have hydrogen substituents and/or any suitable substituent as described herein which satisfy the valencies of the heteroatoms and results in the formation of a stable moiety. In certain embodiments, the substituent is a carbon atom substituent. In certain embodiments, the substituent is a nitrogen atom substituent. In certain embodiments, the substituent is an oxygen atom substituent. In certain embodiments, the substituent is a sulfur atom substituent.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$—C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)(R$^{aa}$)$_2$, —P(=O)(OR$^{cc}$)$_2$, —OP(=O)(R$^{aa}$)$_2$, —OP(=O)(OR$^{cc}$)$_2$, —P(=O)(N(R$^{bb}$)$_2$)$_2$, —OP(=O)(N(R$^{bb}$)$_2$)$_2$, —NR$^{bb}$P(=O)(R$^{aa}$)$_2$, —NR$^{bb}$P(=O)(OR$^{cc}$)$_2$, —NR$^{bb}$P(=O)(N(R$^{bb}$)$_2$)$_2$, —P(R$^{cc}$)$_2$, —P(OR$^{cc}$)$_2$, —P(R$^{cc}$)$_3$$^+$X$^-$, —P(OR$^{cc}$)$_3$$^+$X$^-$, —P(R$^{cc}$)$_4$, —P(OR$^{cc}$)$_4$, —OP(R$^{cc}$)$_2$, —OP(R$^{cc}$)$_3$$^+$X$^-$, —OP(OR$^{cc}$)$_2$, —OP(OR$^{cc}$)$_3$$^+$X$^-$, —OP(R$^{cc}$)$_4$, —OP(OR$^{cc}$)$_4$, —B(R$^{aa}$)$_2$, —B(OR$^{cc}$)$_2$, —BR$^{aa}$(OR$^{cc}$), $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 R$^{dd}$ groups; wherein X$^-$ is a counterion;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)(R$^{aa}$)$_2$, —P(=O)(OR$^{cc}$)$_2$, —P(=O)(N(R$^{cc}$)$_2$)$_2$, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups; wherein $X^-$ is a counterion;

each instance of $R^{cc}$ is, independently, selected from hydrogen, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;

each instance of $R^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)(OR$^{ee}$)$_2$, —P(=O)(R$_{ee}$)$_2$, —OP(=O)(R$^{ee}$)$_2$, —OP(=O)(OR$^{ee}$)$_2$, $C_{1-6}$ alkyl, $C_{1-6}$ perhaloalkyl, $C_{2-6}$ alkenyl, $C_{2-6}$ alkynyl, $C_{3-10}$ carbocyclyl, 3-10 membered heterocyclyl, $C_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 $R^{gg}$ groups, or two geminal $R^{dd}$ substituents can be joined to form =O or =S; wherein $X^-$ is a counterion;

each instance of $R^{ee}$ is, independently, selected from $C_{1-6}$ alkyl, $C_{1-6}$ perhaloalkyl, $C_{2-6}$ alkenyl, $C_{2-6}$ alkynyl, $C_{3-10}$ carbocyclyl, $C_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 $R^{gg}$ groups;

each instance of $R^{ff}$ is, independently, selected from hydrogen, $C_{1-6}$ alkyl, $C_{1-6}$ perhaloalkyl, $C_{2-6}$ alkenyl, $C_{2-6}$ alkynyl, $C_{3-10}$ carbocyclyl, 3-10 membered heterocyclyl, $C_{6-10}$ aryl and 5-10 membered heteroaryl, or two $R^{ff}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3^+$X$^-$, —NH(C$_{1-6}$ alkyl)$_2^+$X$^-$, —NH$_2$(C$_{1-6}$ alkyl)$^+$X$^-$, —NH$_3^+$X$^-$, —N(O$_{1-6}$ alkyl)(C$_{1-6}$ alkyl), —N(OH)(C$_{1-6}$ alkyl), —NH (OH), —SH, —SC$_{1-6}$ alkyl, —SS(C$_{1-6}$ alkyl), —C(=O) (C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N (C$_{1-6}$ alkyl)$_2$, —OC(=O)NH(C$_{1-6}$ alkyl), —NHC(=O) (C$_{1-6}$ alkyl), —N(C$_{1-6}$ alkyl)C(=O)(C$_{1-6}$ alkyl), —NHCO$_2$ (C$_{1-6}$ alkyl), —NHC(=O)N(C$_{1-6}$ alkyl)$_2$, —NHC(=O)NH (C$_{1-6}$ alkyl), —NHC(=O)NH$_2$, —C(=NH)O(C$_{1-6}$ alkyl),—OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH) NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$,—SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$—C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S) SC$_{1-6}$ alkyl, —P(=O)(OC$_{1-6}$ alkyl)$_2$, —P(=O)(C$_{1-6}$ alkyl)$_2$, —OP(=O)(C$_{1-6}$ alkyl)$_2$, —OP(=O)(OC$_{1-6}$ alkyl)$_2$, $C_{1-6}$ alkyl, $C_{1-6}$ perhaloalkyl, $C_{2-6}$ alkenyl, $C_{2-6}$ alkynyl, $C_{3-10}$ carbocyclyl, $C_{6-10}$ aryl, 3-10 membered heterocyclyl, 5-10 membered heteroaryl; or two geminal $R^{gg}$ substituents can be joined to form =O or =S; wherein $X^-$ is a counterion.

each instance of $R^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3^+$X$^-$, —NH(C$_{1-6}$ alkyl)$_2^+$X$^-$, —NH$_2$(C$_{1-6}$ alkyl)$^+$X$^-$, —NH$_3^+$X$^-$, —N(OC$_{1-6}$ alkyl)(C$_{1-6}$ alkyl), —N(OH)(C$_{1-6}$ alkyl), —NH (OH), —SH, —SC$_{1-6}$ alkyl, —SS(C$_{1-6}$ alkyl), —C(=O) (C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N (C$_{1-6}$ alkyl)$_2$, —OC(=O)NH(C$_{1-6}$ alkyl), —NHC(=O) (C$_{1-6}$ alkyl), —N(C$_{1-6}$ alkyl)C(=O)(C$_{1-6}$ alkyl), —NHCO$_2$ (C$_{1-6}$ alkyl), —NHC(=O)N(C$_{1-6}$ alkyl)$_2$, —NHC(=O)NH (C$_{1-6}$ alkyl), —NHC(=O)NH$_2$, —C(=NH)O(C$_{1-6}$ alkyl),—OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH) NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$,—SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$—C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S) SC$_{1-6}$ alkyl, —P(=O)(OC$_{1-6}$ alkyl)$_2$, —P(=O)(C$_{1-6}$ alkyl)$_2$, —OP(=O)(C$_{1-6}$ alkyl)$_2$, —OP(=O)(OC$_{1-6}$ alkyl)$_2$, $C_{1-6}$ alkyl, $C_{1-6}$ perhaloalkyl, $C_{2-6}$ alkenyl, $C_{2-6}$ alkynyl, $C_{3-10}$ carbocyclyl, $C_{6-10}$ aryl, 3-10 membered heterocyclyl, 5-10 membered heteroaryl; or two geminal $R^{gg}$ substituents can be joined to form =O or =S; wherein $X^-$ is a counterion.

A "counterion" or "anionic counterion" is a negatively charged group associated with a positively charged group in order to maintain electronic neutrality. An anionic counterion may be monovalent (i.e., including one formal negative charge). An anionic counterion may also be multivalent (i.e., including more than one formal negative charge), such as divalent or trivalent. Exemplary counterions include halide ions (e.g., F$^-$, Cl$^-$, Br$^-$, I$^-$), NO$_3^-$, ClO$_4^-$, OH$^-$, H$_2$PO$_4^-$, HSO$_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), carboxylate ions (e.g., acetate, propanoate, benzoate, glycerate, lactate, tartrate, glycolate, gluconate, and the like), BF$_4^-$, PF$_4^-$, PF$_6^-$, AsF$_6^-$, SbF$_6^-$, B[3,5-(CF$_3$)$_2$C$_6$H$_3$]$_4^-$, BPh$_4^-$, Al(OC(CF$_3$)$_3$)$_4^-$, and a carborane anion (e.g., CB$_{11}$H$_{12}^-$ or (HCB$_{11}$Me$_5$Br$_6$)$^-$). Exemplary counterions which may be multivalent include CO$_3^{2-}$, HPO$_4^{2-}$, PO$_4^{3-}$, B$_4$O$_7^{2-}$, SO$_4^{2-}$, S$_2$O$_3^{2-}$, carboxylate anions (e.g., tartrate, citrate, fumarate, maleate, malate, malonate, gluconate, succinate, glutarate, adipate, pimelate, suberate, azelate, sebacate, salicylate, phthalates, aspartate, glutamate, and the like), and carboranes.

"Halo" or "halogen" refers to fluorine (fluoro, —F), chlorine (chloro, —Cl), bromine (bromo, —Br), or iodine (iodo, —I).

"Acyl" refers to a moiety selected from the group consisting of —C(=O)R$^{aa}$, —CHO, —CO$_2$R$^{aa}$, —C(=O)N $(R^{bb})_2$, —C(=NR$^{bb}$)R$^{aa}$, —C(=NR$^{bb}$)OR$^{aa}$, —C(=NR$^{bb}$)N(R$^{bb}$)$_2$, —C(=O)NR$^{bb}$SO$_2$R$^{aa}$, —C(=S)N(R$^{bb}$)$_2$, —C(=O)SR$^{aa}$, or —C(=S)SR$^{aa}$, wherein R$^{aa}$ and R$^{bb}$ are as defined herein.

Nitrogen atoms can be substituted or unsubstituted as valency permits, and include primary, secondary, tertiary, and quaternary nitrogen atoms. Exemplary nitrogen atom substituents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)(OR$^{cc}$)$_2$, —P(=O)(R$^{aa}$)$_2$, —P(=O)(N(R$^{cc}$)$_2$)$_2$, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two R$^{cc}$ groups attached to a nitrogen atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups, and wherein R$^{aa}$, R$^{bb}$, R$^{cc}$, and R$^{dd}$ are as defined above.

Exemplary oxygen atom substituents include, but are not limited to, —R$^{aa}$, —C(=O)SR$^{aa}$, —C(=O)R$^{aa}$, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —S(=O)R$^{aa}$, —SO$_2$R$^{aa}$, —Si(R$^{aa}$)$_3$, —P(R$^{cc}$)$_2$, —P(R$^{cc}$)$_3$$^+$X$^-$, —P(OR$^{cc}$)$_2$, —P(OR$^{cc}$)$_3$$^+$X$^-$, —P(=O)(R$^{aa}$)$_2$, —P(=O)(OR$^{cc}$)$_2$, and —P(=O)(N(R$^{bb}$)$_2$)$_2$, wherein X$^-$, R$^{aa}$, R$^{bb}$, and R$^{cc}$ are as defined herein.

The term "salt" refers to ionic compounds that result from the neutralization reaction of an acid and a base. A salt is composed of one or more "cations" (positively charged ions) and one or more "anions" (negatively charged ions) so that the salt is electrically neutral (without a net charge). Salts described herein may include those derived from suitable organic acids as disclosed herein, for example, dicarboxylic acids. Examples of organic and inorganic acids include but not limited to acetic acid, ascorbic acid, aspartic acid, benzoic acid, formic acid, fumaric acid, galic acid, gluconic acid, lactic acid, lauric acid, methansulfonic acid, niconitic acid, oxalic acid, oxalic acid, maleic acid, malonic acid, L-tartaric acid, D-tartaric acid, meso-tartaric acid, malic acid, citric acid, succinic acid, stearic acid, pentetic acid, propinoic acid, p-toluenesulfonic acid, undecanoic acid, valeric acid, ethylenediaminetetraacetic acid, boric acid, hydrochloric acid, hydrobromic acid, chromic acid, nitric acid, phosphoric acid, phosphorous acid, hypophosphorus acid, sulfuric acid, and sulfonic acid.

The term "cycloserine compound" refers to cycloserine (in D- or L-form or a racemic mixture of the DL-form), or pharmaceutically acceptable salts or esters thereof, or functional derivatives thereof. In some embodiments, a cycloserine compound can be nano-crystalline D-cycloserine. In some embodiments, a cycloserine compound can be nano-crystalline L-crystalline. In other embodiments, a cycloserine compound is a racemic mixture of DL-cycloserine in nano-crystalline form. The chemical structure of cycloserine is provided below:

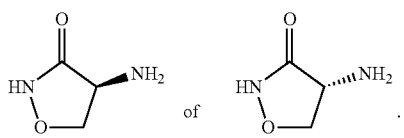

A functional derivative of cycloserine can be a compound having the same core structure of cycloserine with one or more substituents, for example, alkyl, alkenyl, alkynyl, and/or a halogen.

A "subject" to which administration is contemplated refers to a human (i.e., male or female of any age group, e.g., pediatric subject (e.g., infant, child, or adolescent) or adult subject (e.g., young adult, middle-aged adult, or senior adult)) or non-human animal. A "patient" refers to a human subject in need of treatment of a disease.

The terms "administer," "administering," or "administration" refers to implanting, absorbing, ingesting, injecting, inhaling, or otherwise introducing the salt of formula [A][B], wherein [A] is a cation form of a cycloserine compound and [B] is an anion form of a compound of formula (I) described herein, or a composition thereof, in or on a subject.

The terms "treatment," "treat," and "treating" refer to reversing, alleviating, delaying the onset of, or inhibiting the progress of a disease described herein. In some embodiments, treatment may be administered after one or more signs or symptoms of the disease have developed or have been observed. In other embodiments, treatment may be administered in the absence of signs or symptoms of the disease. For example, treatment may be administered to a susceptible subject prior to the onset of symptoms (e.g., in light of a history of symptoms and/or in light of exposure to a pathogen) to delay or prevent disease occurrence. Treatment may also be continued after symptoms have resolved, for example, to delay or prevent recurrence.

The terms "condition," "disease," and "disorder" are used interchangeably.

An "effective amount" of the salt of formula [A][B] described herein refers to an amount sufficient to elicit the desired biological response, i.e., treating the condition. As will be appreciated by those of ordinary skill in this art, the effective amount of the salt of cycloserine and a compound of formula (I) described herein may vary depending on such factors as the desired biological endpoint, the pharmacokinetics of the salt of formula [A][B], the condition being treated, the mode of administration, and the age and health of the subject. In certain embodiments, an effective amount is a therapeutically effective amount. In certain embodiments, an effective amount is a prophylactic effective amount. In certain embodiments, an effective amount is the amount of the salt of formula [A][B] described herein in a single dose. In certain embodiments, an effective amount is the combined amounts of the salt of formula [A][B] described herein in multiple doses.

A "therapeutically effective amount" of the salt of formula [A][B] described herein is an amount sufficient to provide a therapeutic benefit in the treatment of a condition or to delay or minimize one or more symptoms associated with the condition. A therapeutically effective amount of the salt of formula [A][B] means an amount of therapeutic agent, alone or in combination with other therapies, which provides a therapeutic benefit in the treatment of the condition. The term "therapeutically effective amount" can encompass an amount that improves overall therapy, reduces or avoids symptoms, signs, or causes of the condition, and/or enhances the therapeutic efficacy of another therapeutic agent.

A "prophylactically effective amount" of the salt of formula [A][B] described herein is an amount sufficient to prevent a condition, or one or more symptoms associated with the condition or prevent its recurrence. A prophylactically effective amount of the salt of formula [A][B] means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent.

The term "neuropsychiatric disorder," including either neurological diseases or psychiatric disorders or CNS disorders, or refers to a disorder that involves either psychiatric symptoms or syndromes caused by organic brain disorders. The main characteristics of neuropsychiatric symptoms include occurrence of the various psychiatric symptoms, cognitive impairment, neurological symptoms or the possibility of early cerebral development symptoms. For example, the neuropsychiatric disorder can include, but not limited to, schizophrenia, psychotic disorders, Alzheimer's disease, frontotemporal dementia, vascular dementia, dementia with Lewy bodies, senile dementia, mild cognitive impairment, benign forgetfulness, closed head injury, autistic spectrum disorder, Asperger's disorder, fragile X syndrome, attention deficit hyperactivity disorders, attention deficit disorder, obsessive compulsive disorder, tic disorders, childhood learning disorders, premenstrual syndrome, depression, major depressive disorder, anhedonia, suicidal ideation and/or behaviors, bipolar disorder, anxiety disorders, panic disorder, post-traumatic stress disorder, chronic mild and unpredictable stress, eating disorders, addiction disorders, personality disorders, Parkinson's disorder, Huntington's disorder, multiple sclerosis, amyotrophic lateral sclerosis, ataxia, Friedreich's ataxia, Tourette's syndrome, nocturnal enuresis, non-epileptic seizures, blepharospasm, Duchenne muscular dystrophy, stroke, chronic pain, neuropathic pain including hyperalgesia and allodynia, diabetic polyneuropathy, and chronic pain syndromes.

The terms "health food" or "health food product" refers to any kind of liquid and solid/semi-solid materials that are used for nourishing humans and animals, for improving basic behavioral functioning, hyperactivity, anxiety, depression, sensorimotor gating, pain threshold, memory and/or cognitive functioning, body weight, or for facilitating treatment of any of the target diseases noted herein. The term "nutraceutical composition" refers to compositions containing components from food sources and conferring extra health benefits in addition to the basic nutritional value found in foods.

The terms "medical food" or "medical food product" refers to a food product formulated to be consumed or administered enterally, including a food product that is usually used under the supervision of a physician for the specific dietary management of a target disease, such as those described herein. A "medical food product" composition may refer to a composition that is specially formulated and processed (as opposed to a naturally occurring foodstuff used in a natural state) for a patient in need of the treatment (e.g., human patients who suffer from illness or who requires use of the product as a major active agent for alleviating a disease or condition via specific dietary management).

DETAILED DESCRIPTION

Figure 1:
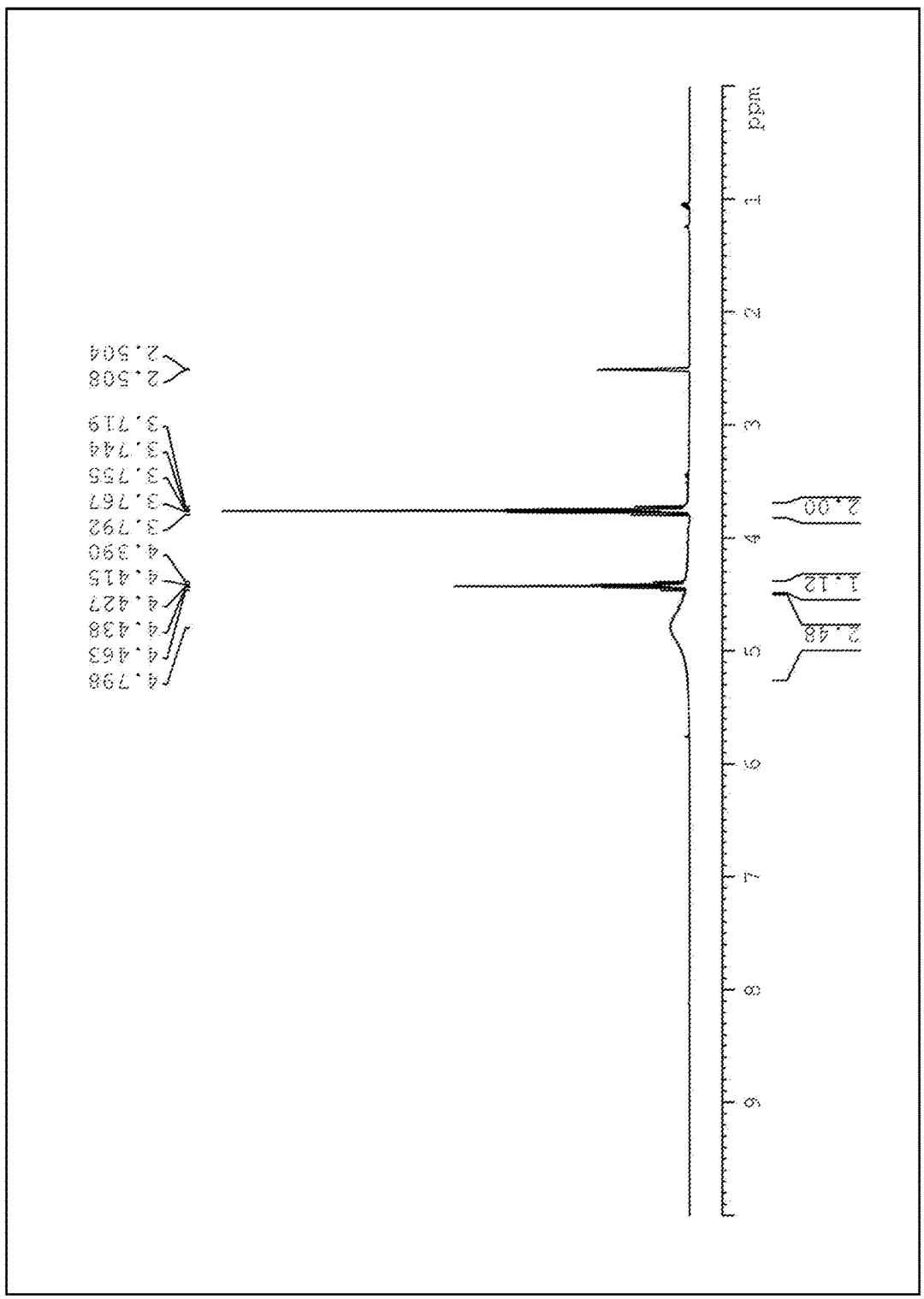
FIG. 1 shows a $^1$H-NMR spectrum of D-cycloserine from Strides Shasun Ltd.
Figure 2:
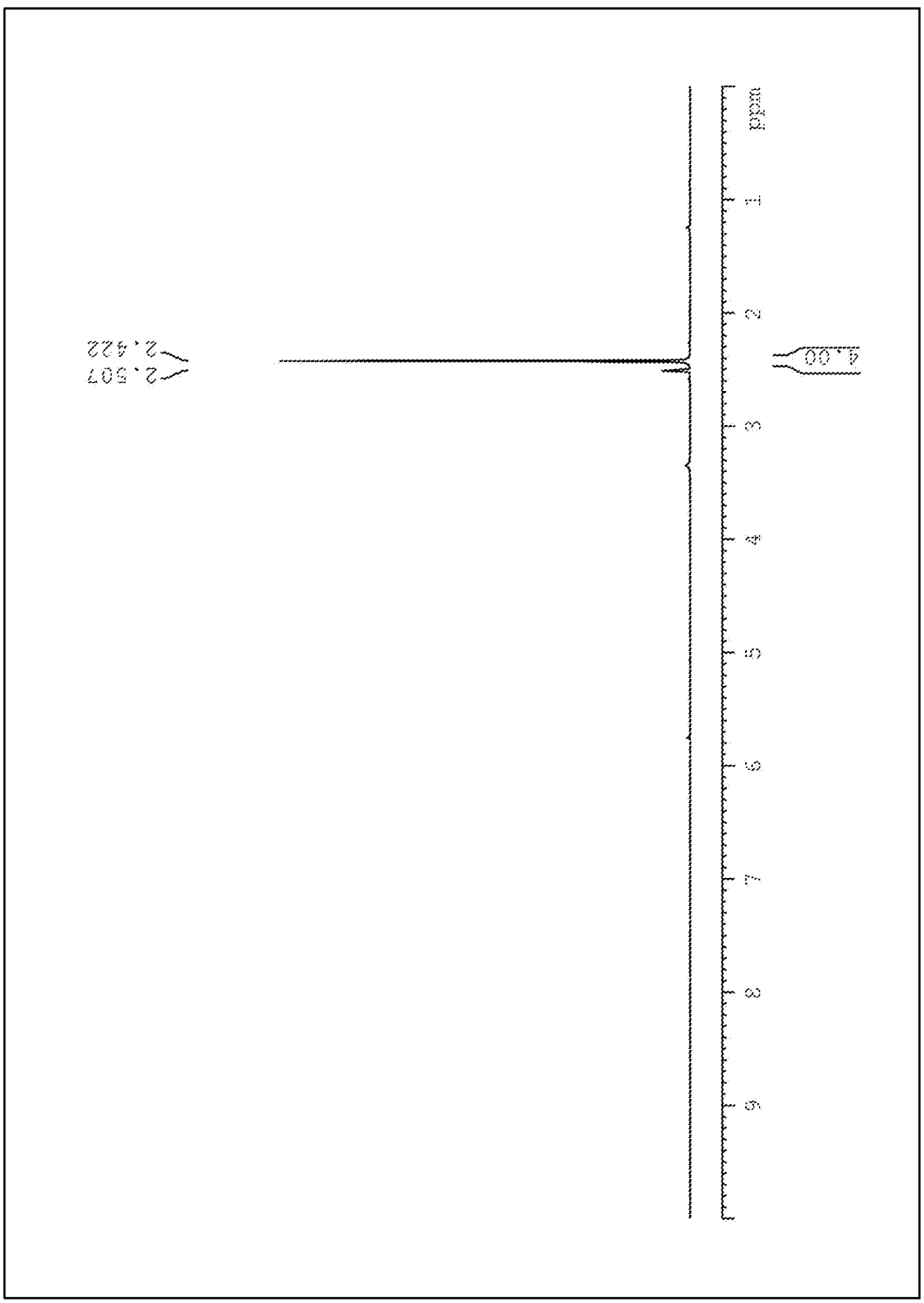
FIG. 2 shows a $^1$H-NMR spectrum of succinic acid.
Figure 3:
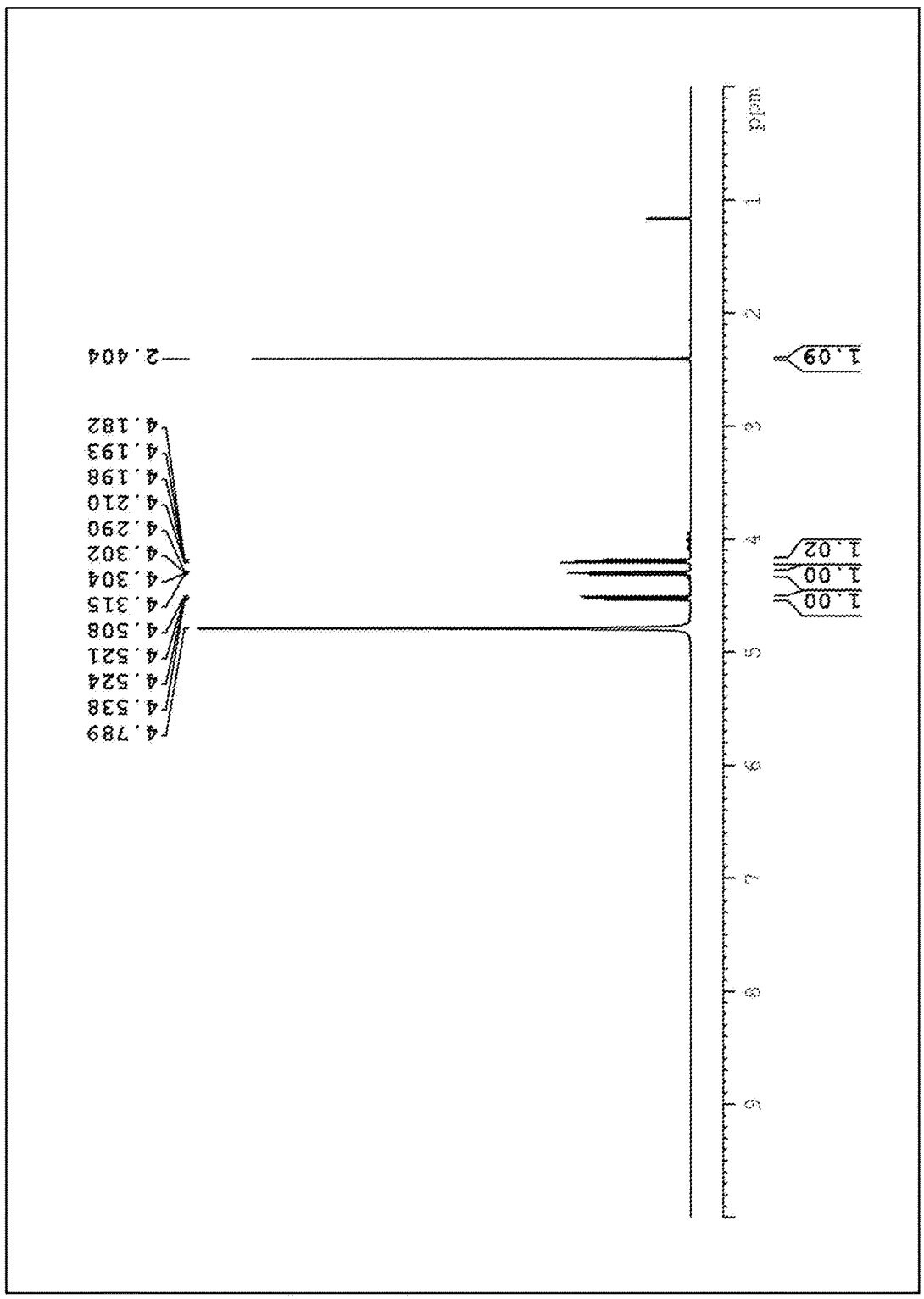
FIG. 3 shows a $^1$H-NMR spectrum of D-cycloserine succinate salt form.
Figure 4:
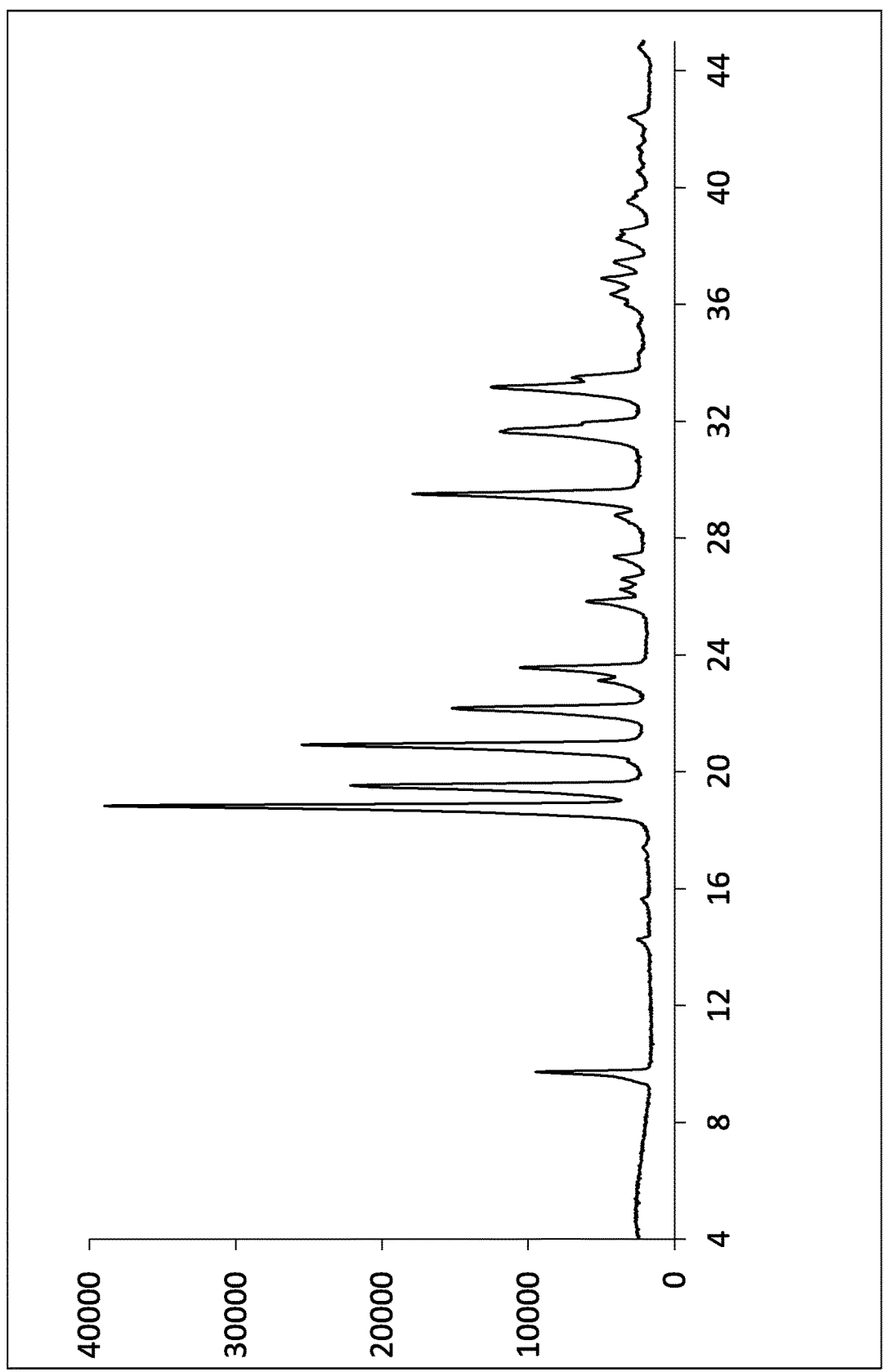
FIG. 4 shows an X-ray powder diffraction (XRPD) spectrum of D-cycloserine from Strides Shasun Ltd.
Figure 5:
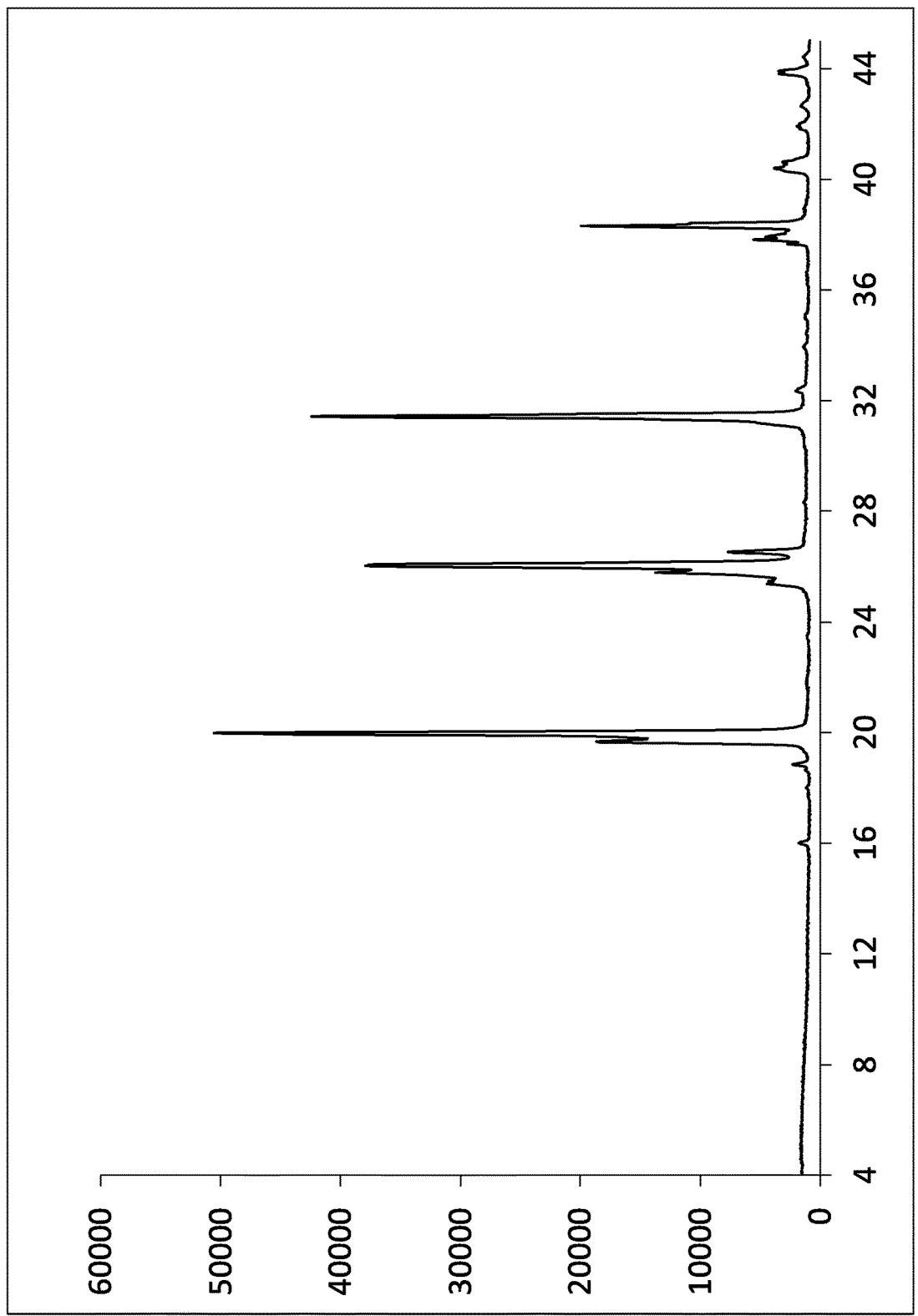
FIG. 5 shows an XRPD spectrum of succinic acid.
Figure 6:
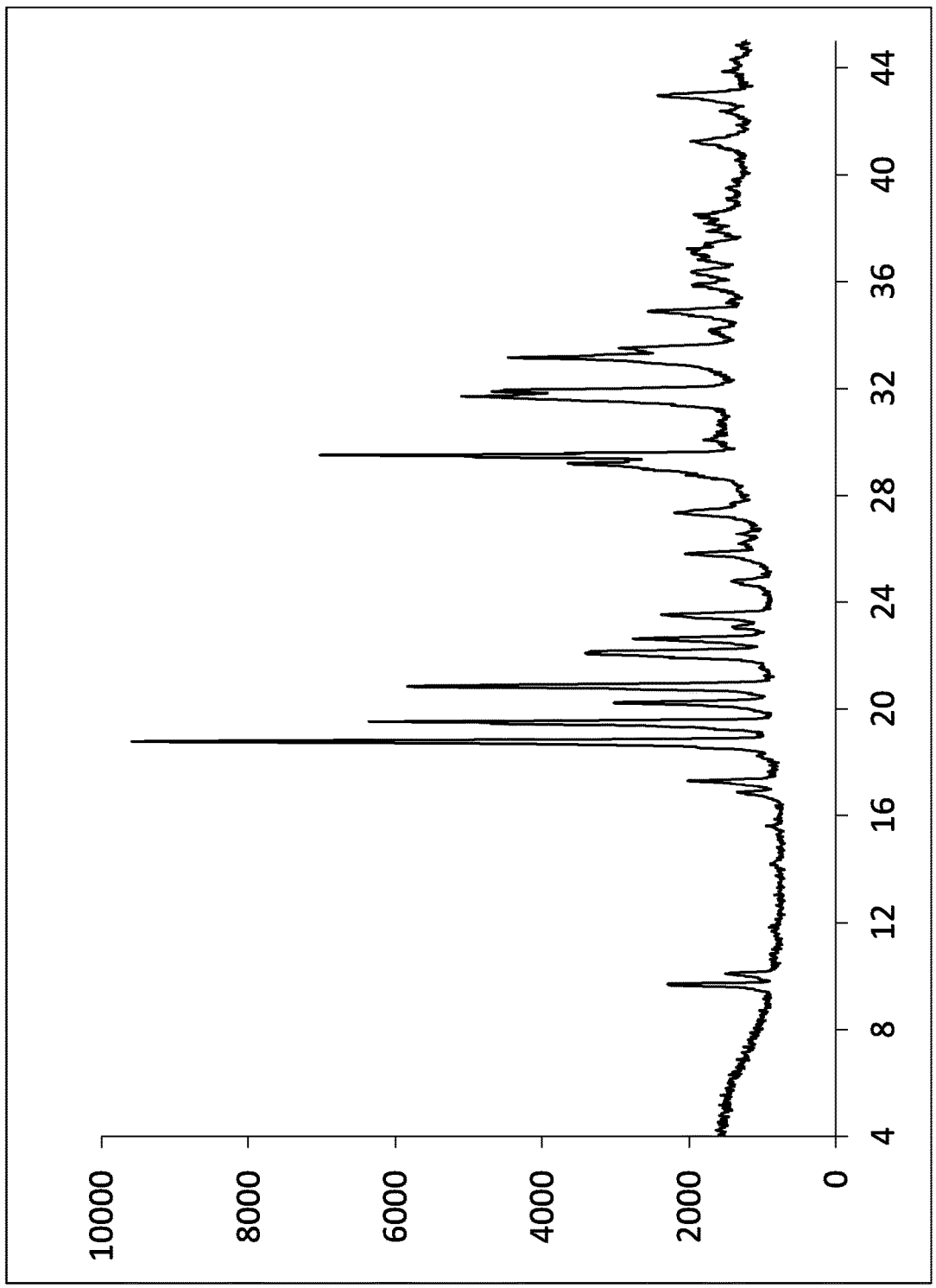
FIG. 6 shows an XRPD spectrum of D-cycloserine succinate (4:1) salt form, confirming salt formation.
Figure 7:
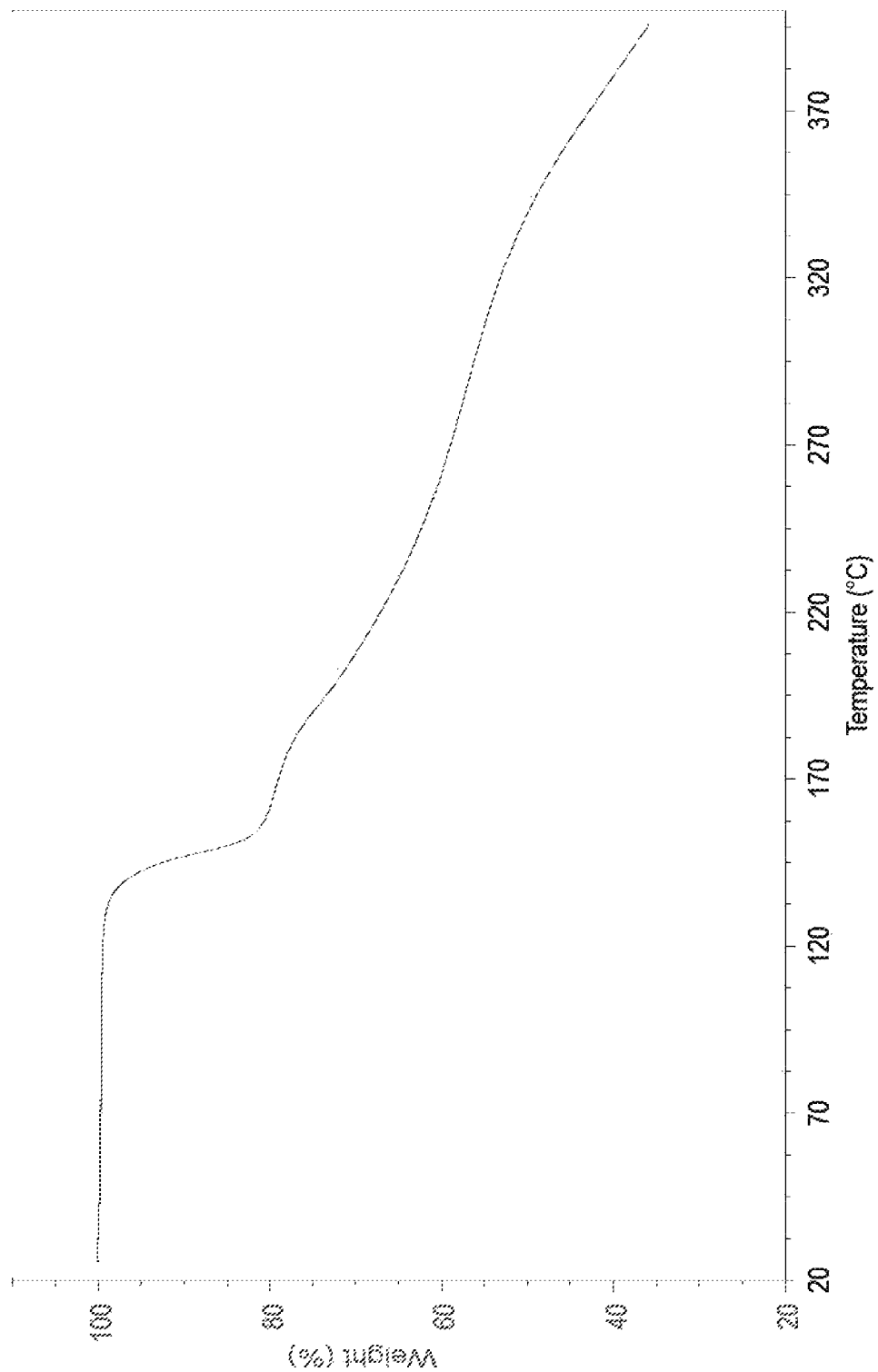
FIG. 7 shows a thermal gravimetric analysis (TGA) profile of D-cycloserine.
Figure 8:
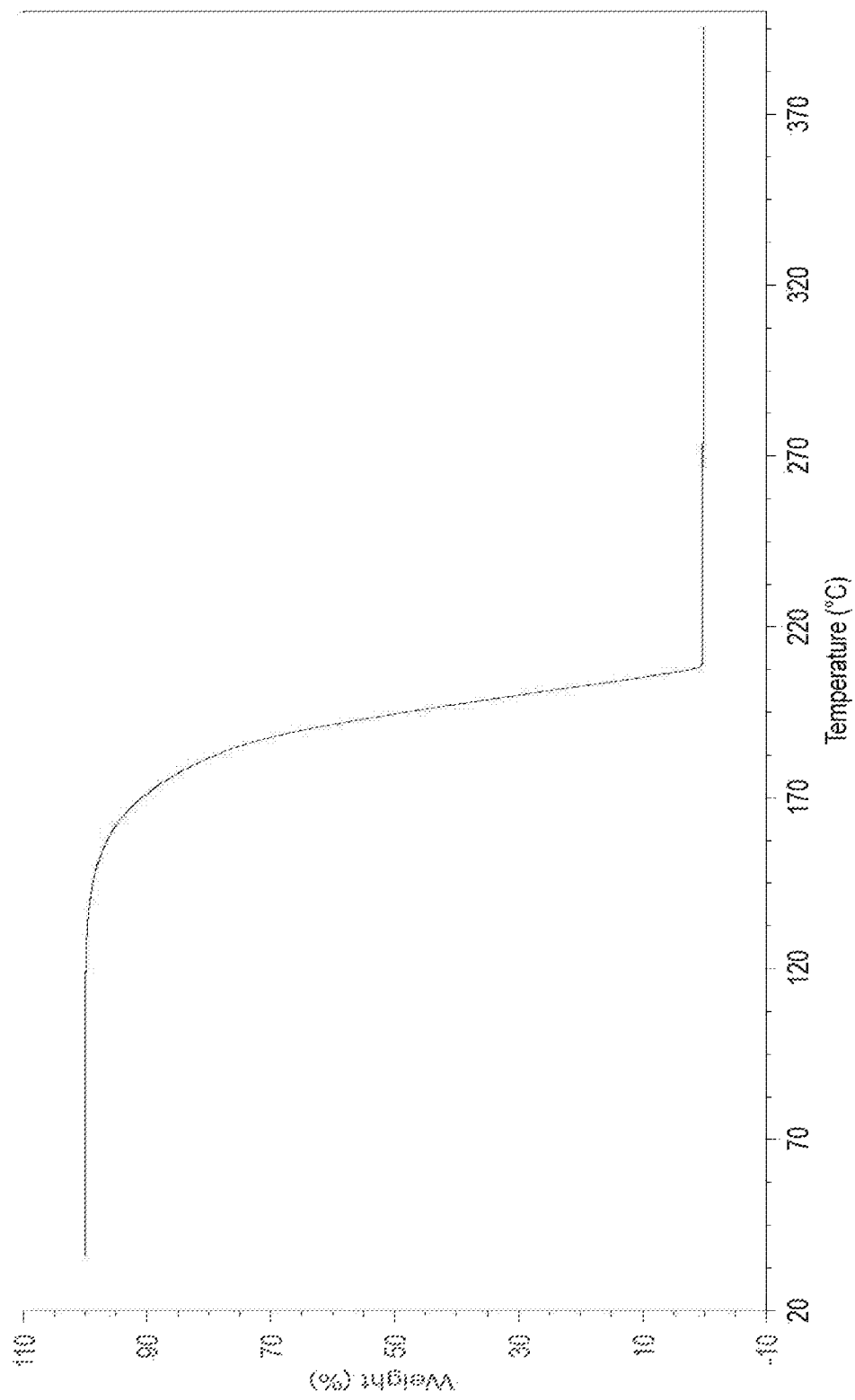
FIG. 8 shows a TGA profile of succinic acid.
Figure 9:
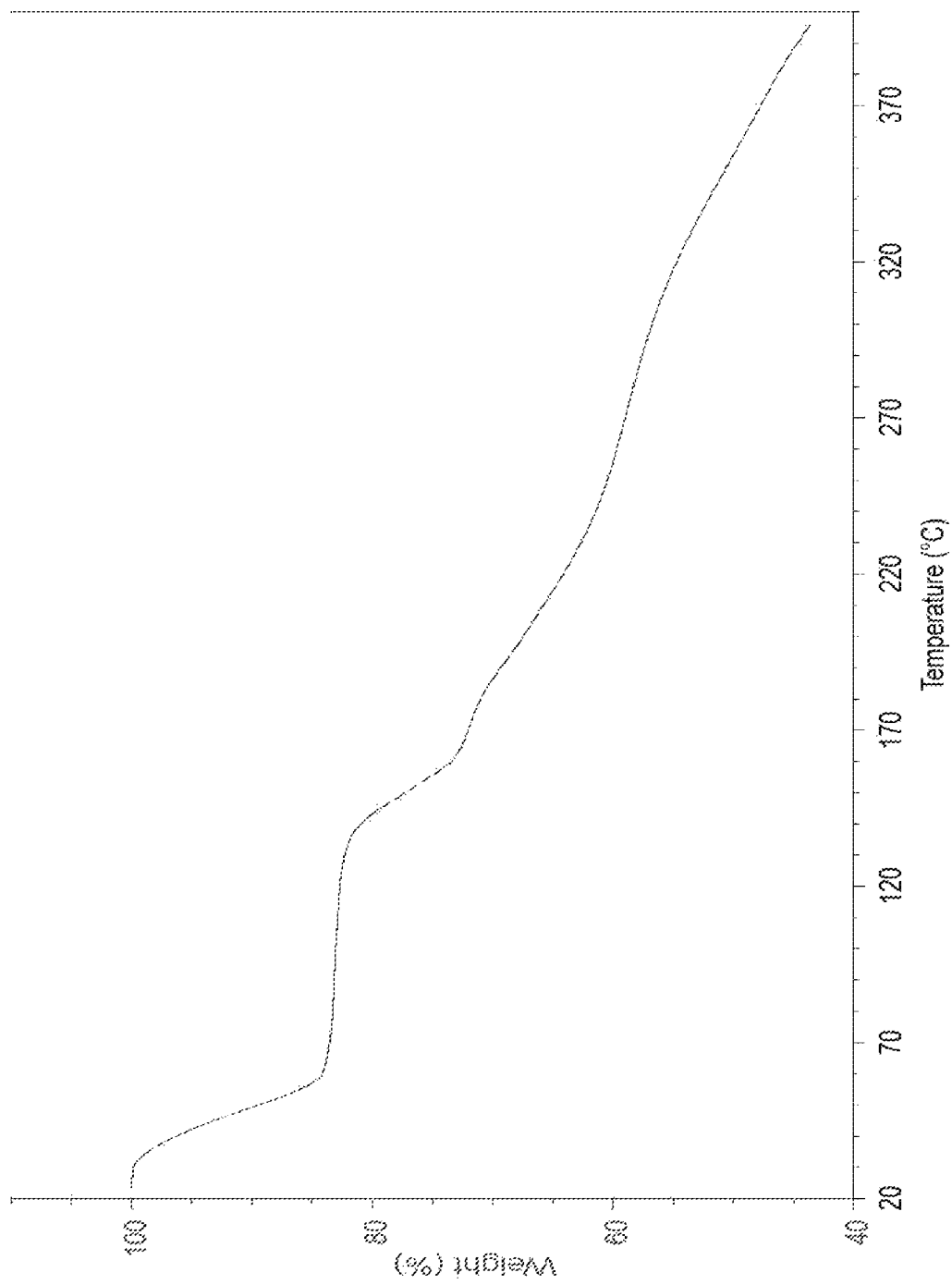
FIG. 9 shows a TGA profile confirming D-cycloserine succinate (4:1) salt form, which is distinct from D-cycloserine and succinic acid.
Figure 10:
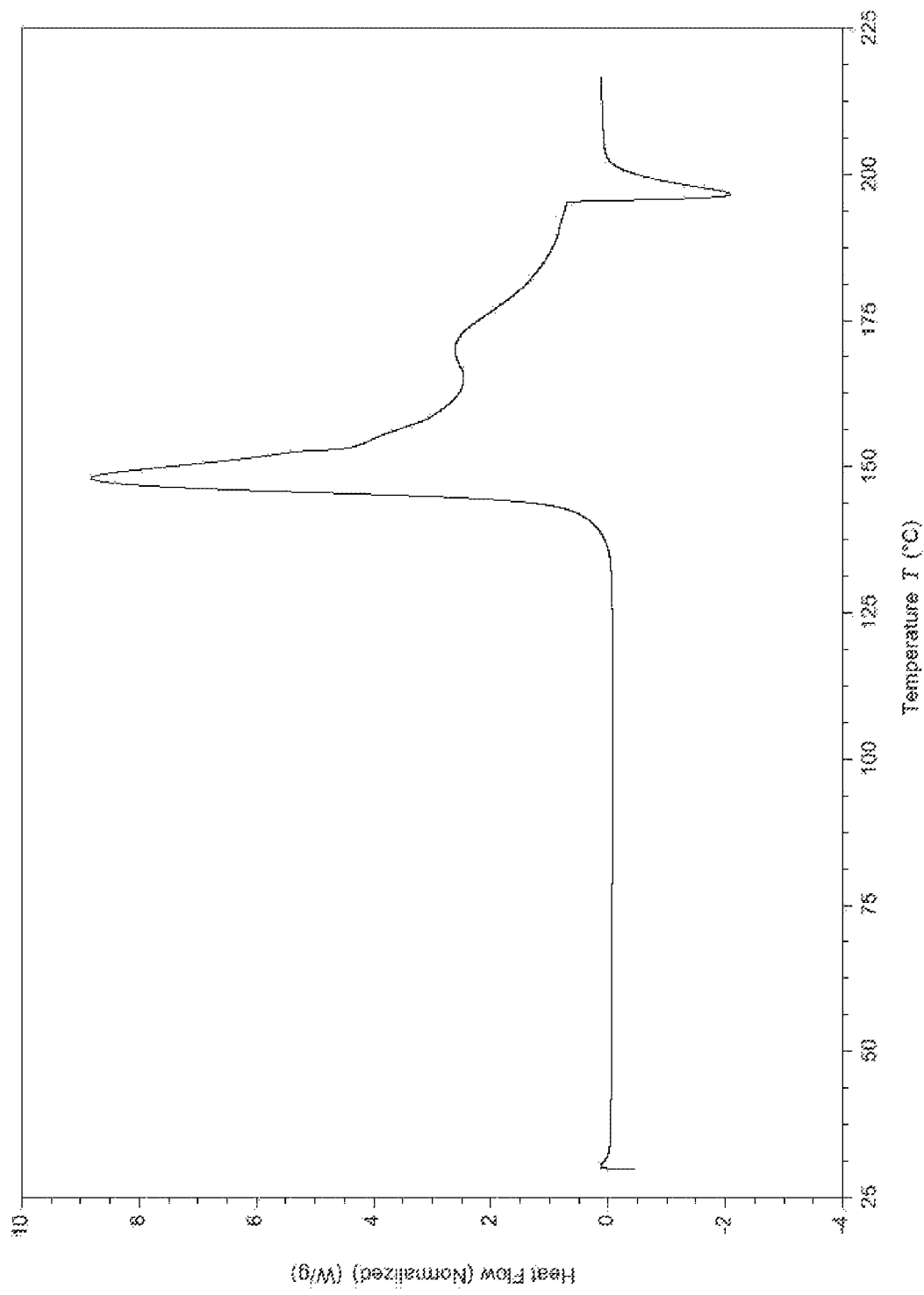
FIG. 10 shows a Differential Scanning Calorimetry (DSC) profile of D-cycloserine from Strides Shasun Ltd.
Figure 11:
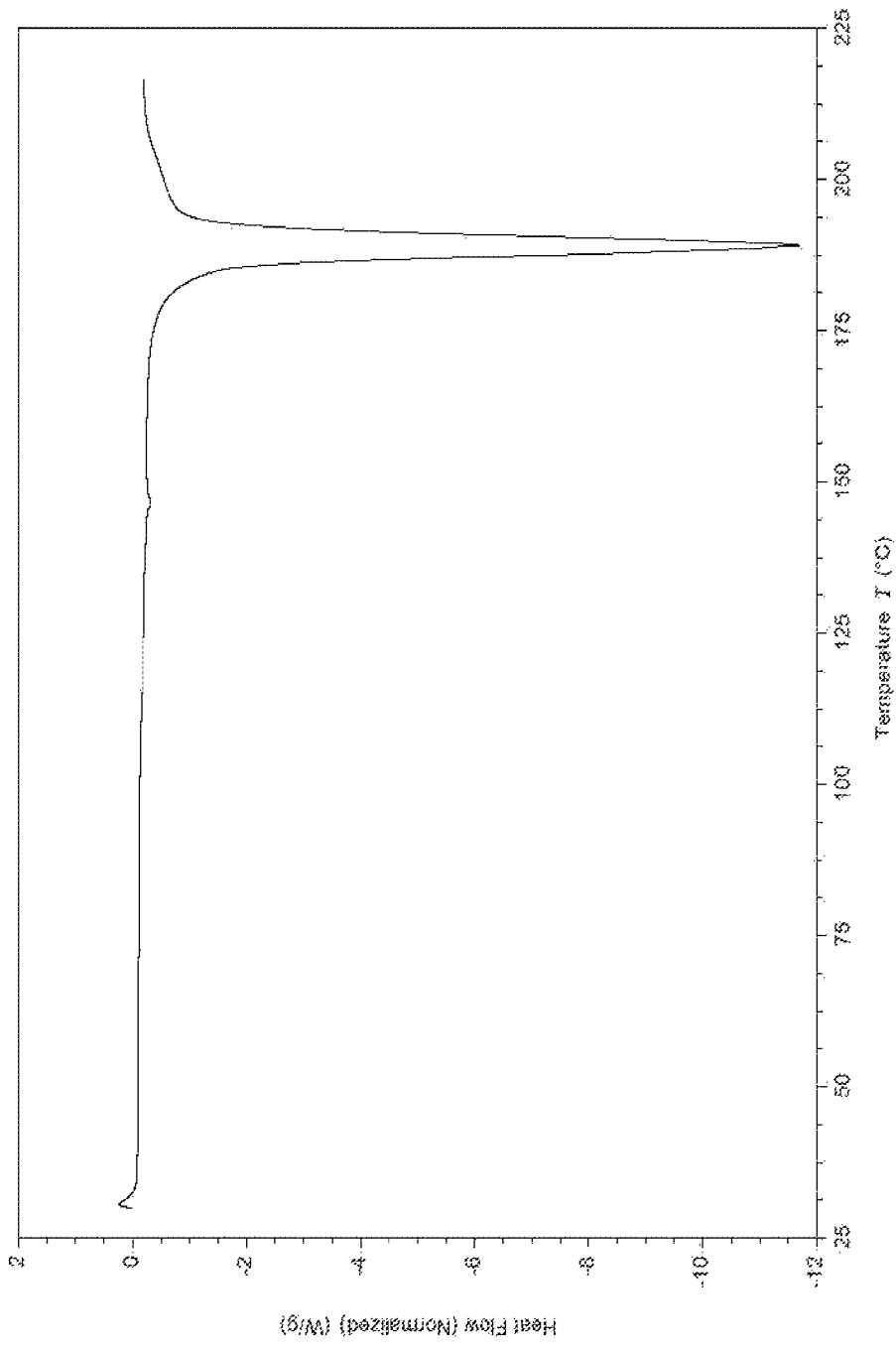
FIG. 11 shows a DSC profile of succinic acid.
Figure 12:
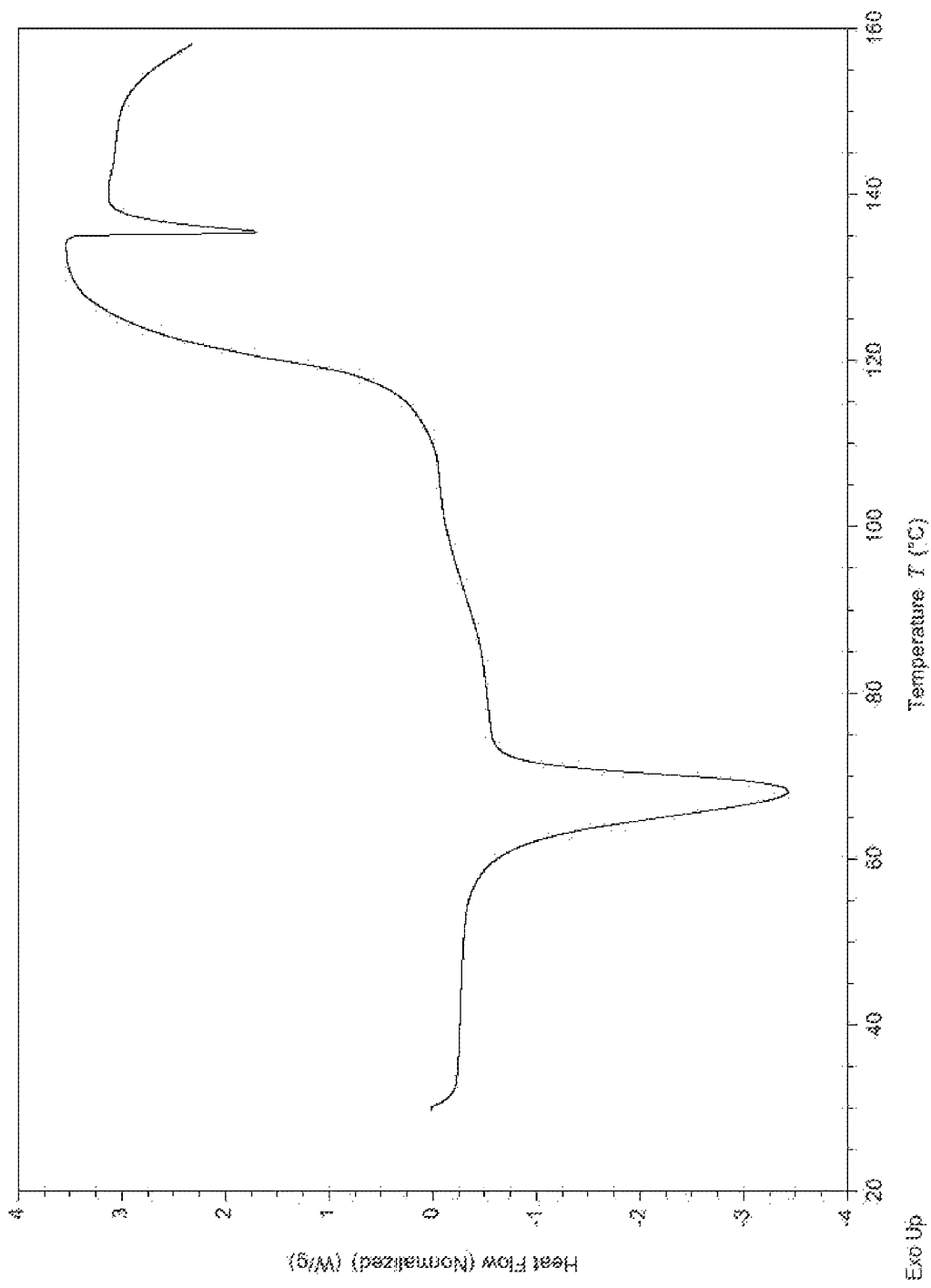
FIG. 12 shows a DSC profile confirming D-cycloserine succinate (4:1) salt form.
Figure 13:
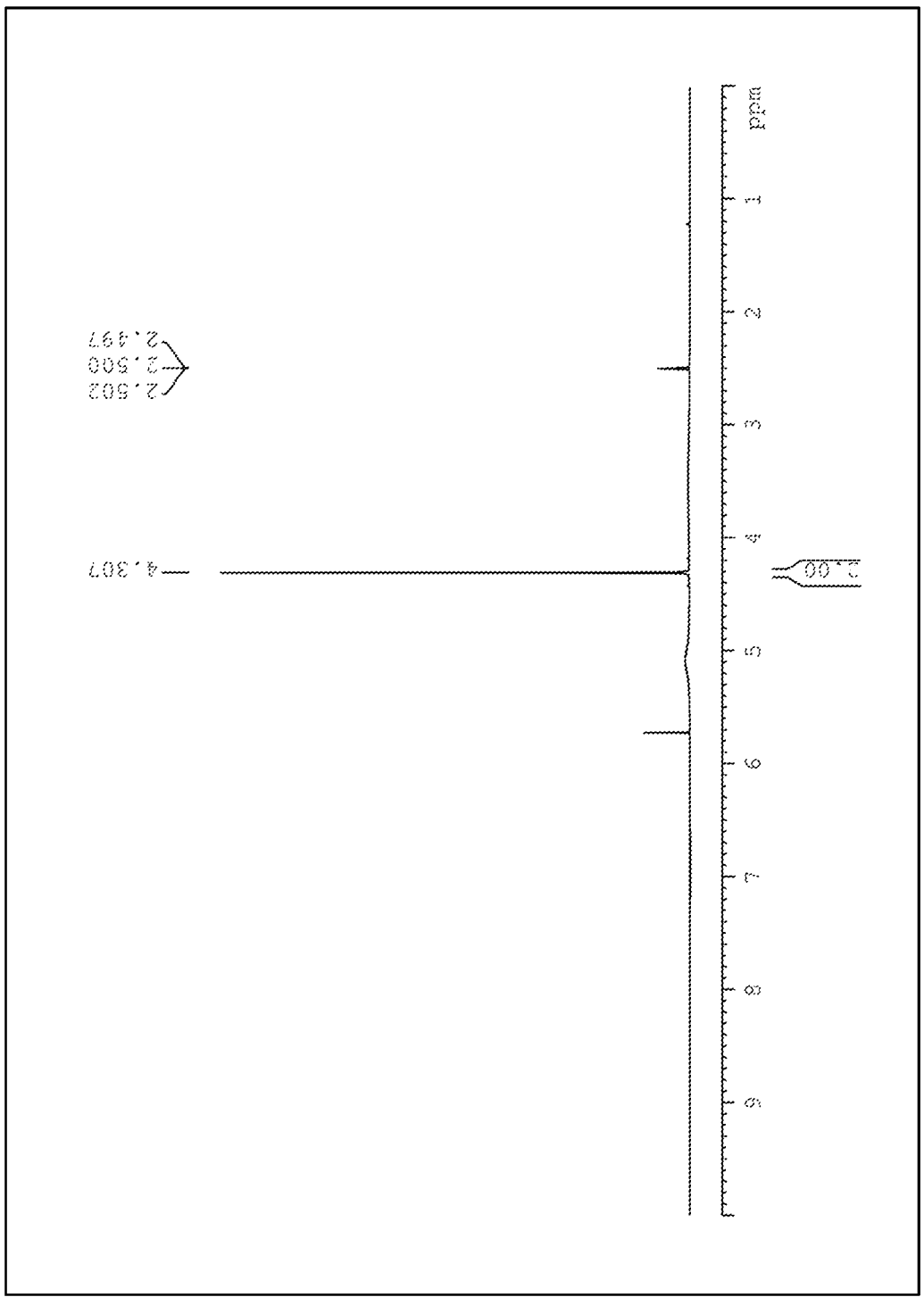
FIG. 13 shows a $^1$H-NMR spectrum of L-tartaric acid.
Figure 14:
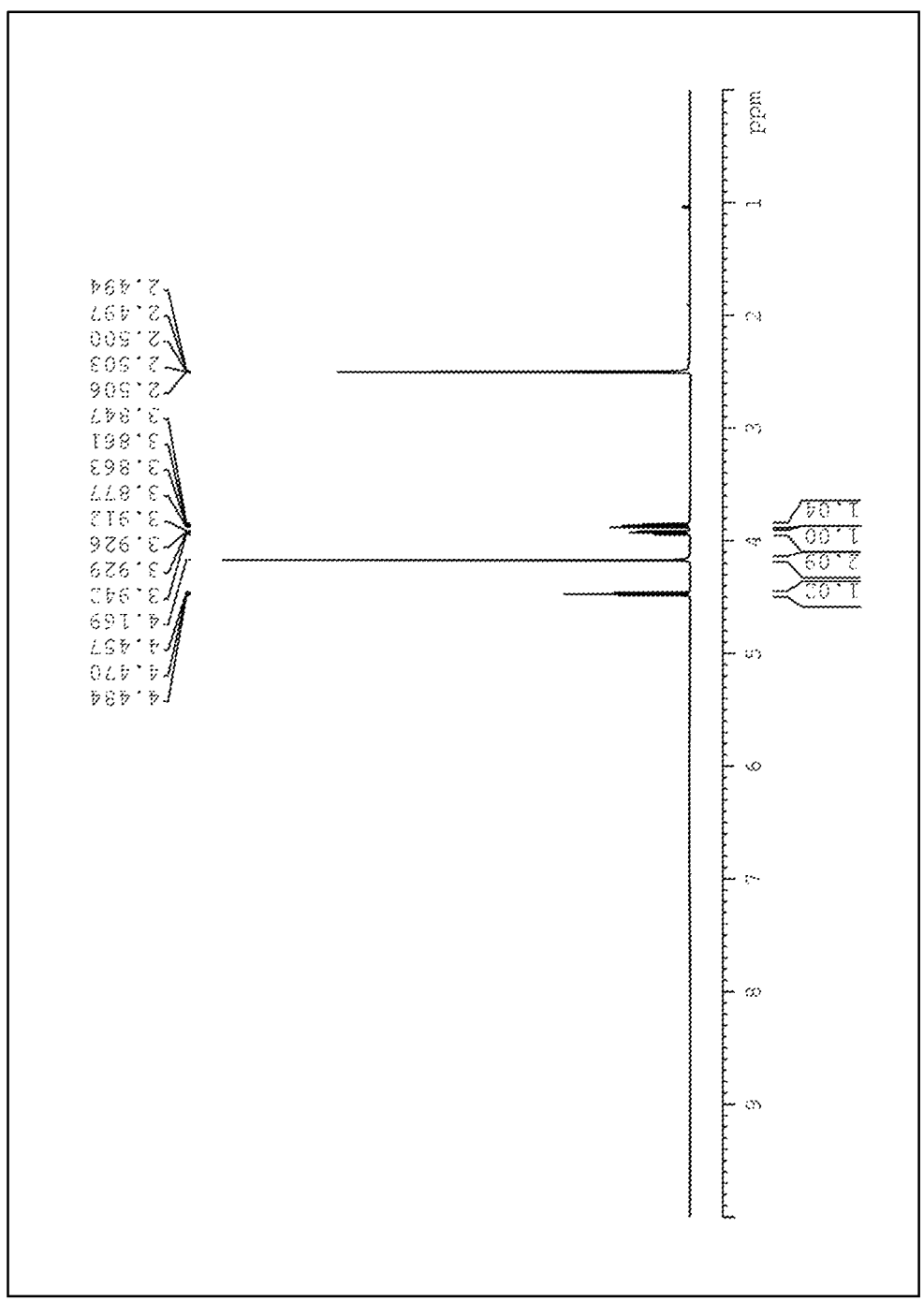
FIG. 14 shows a $^1$H-NMR spectrum confirming D-cycloserine L-tartarate (1:1) salt form.
Figure 15:
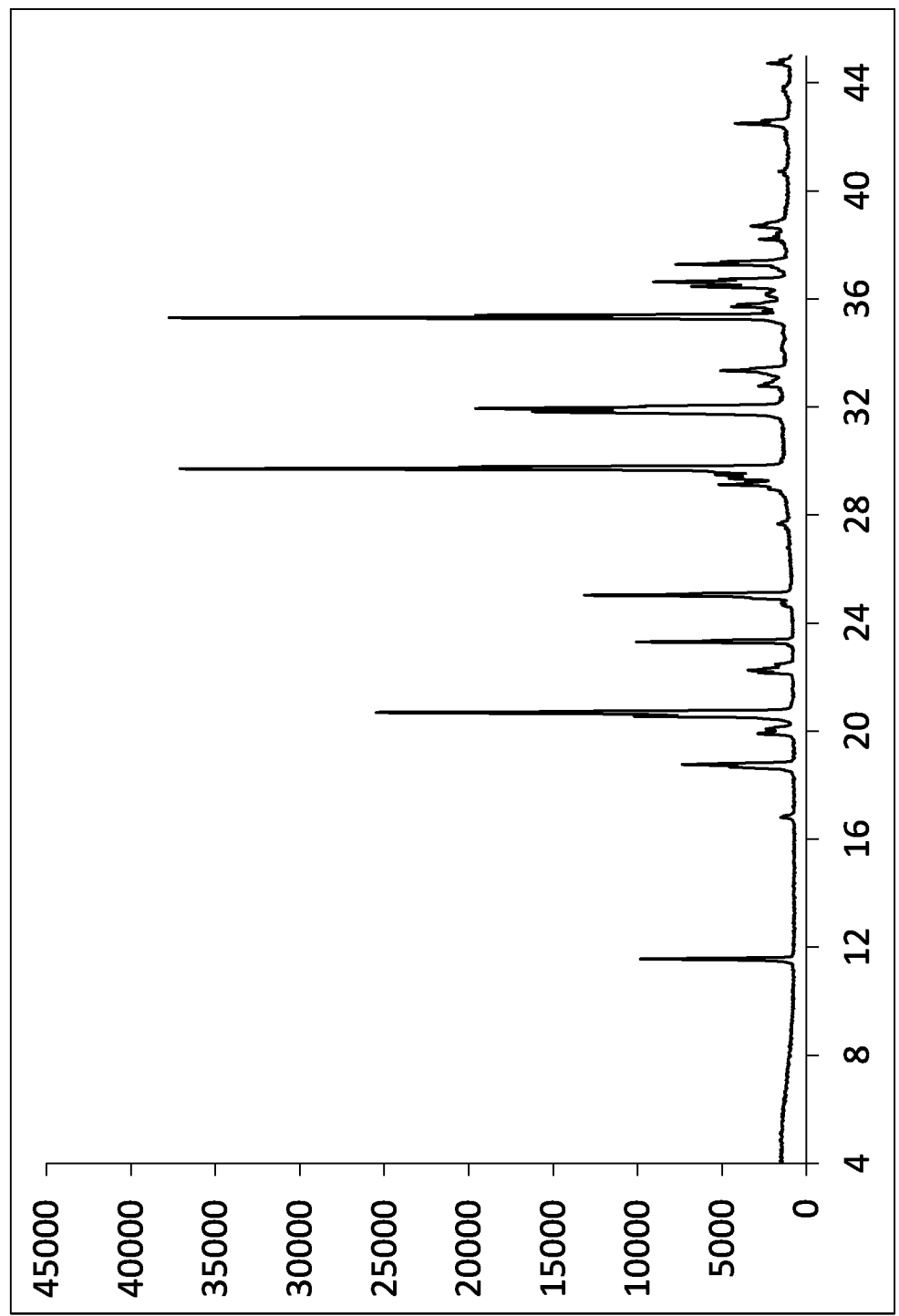
FIG. 15 shows an XRPD spectrum of L-tartaric acid.
Figure 16:
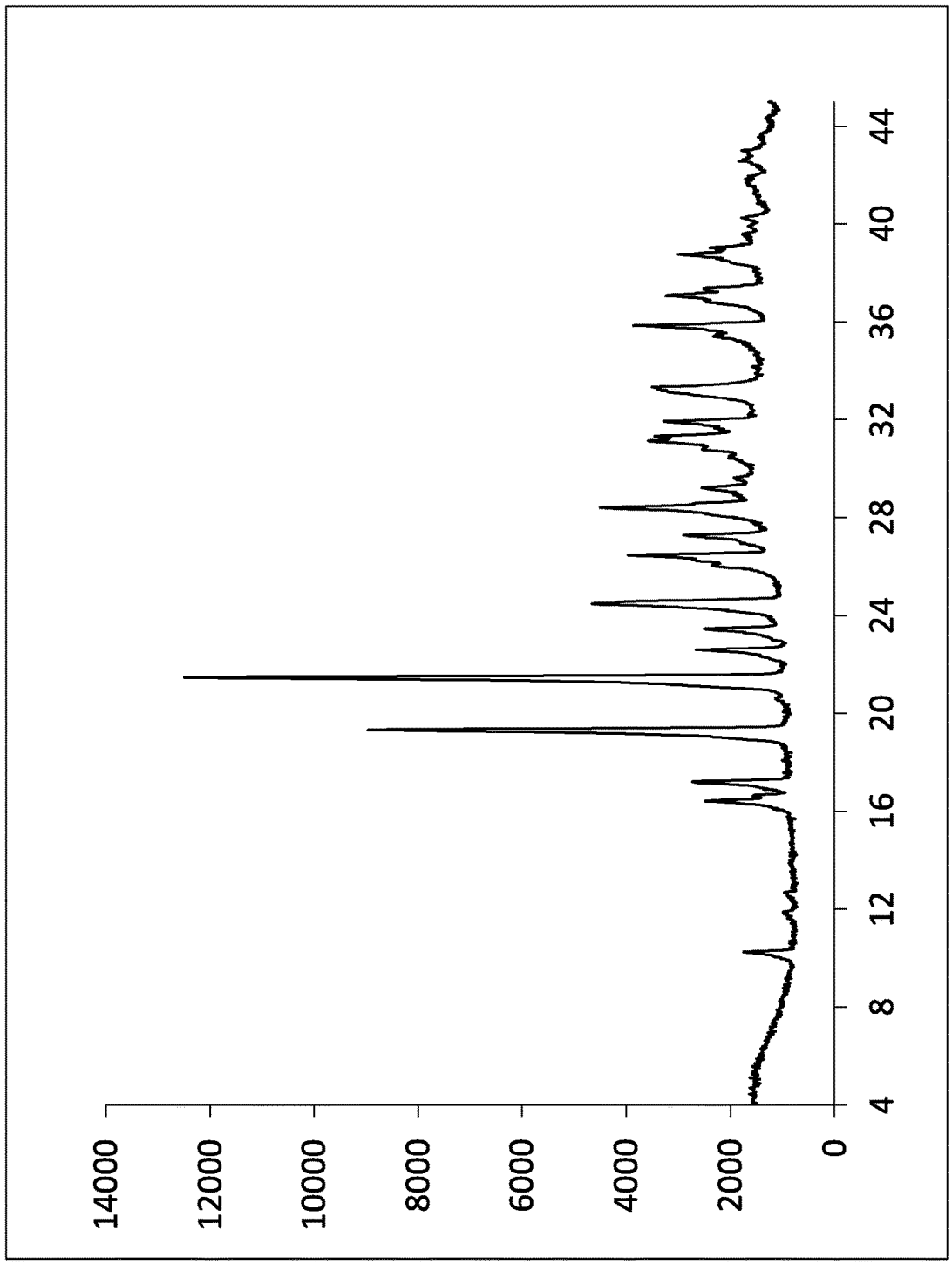
FIG. 16 shows an XRPD spectrum confirming D-cycloserine L-tartarate (1:1) salt form.
Figure 17:
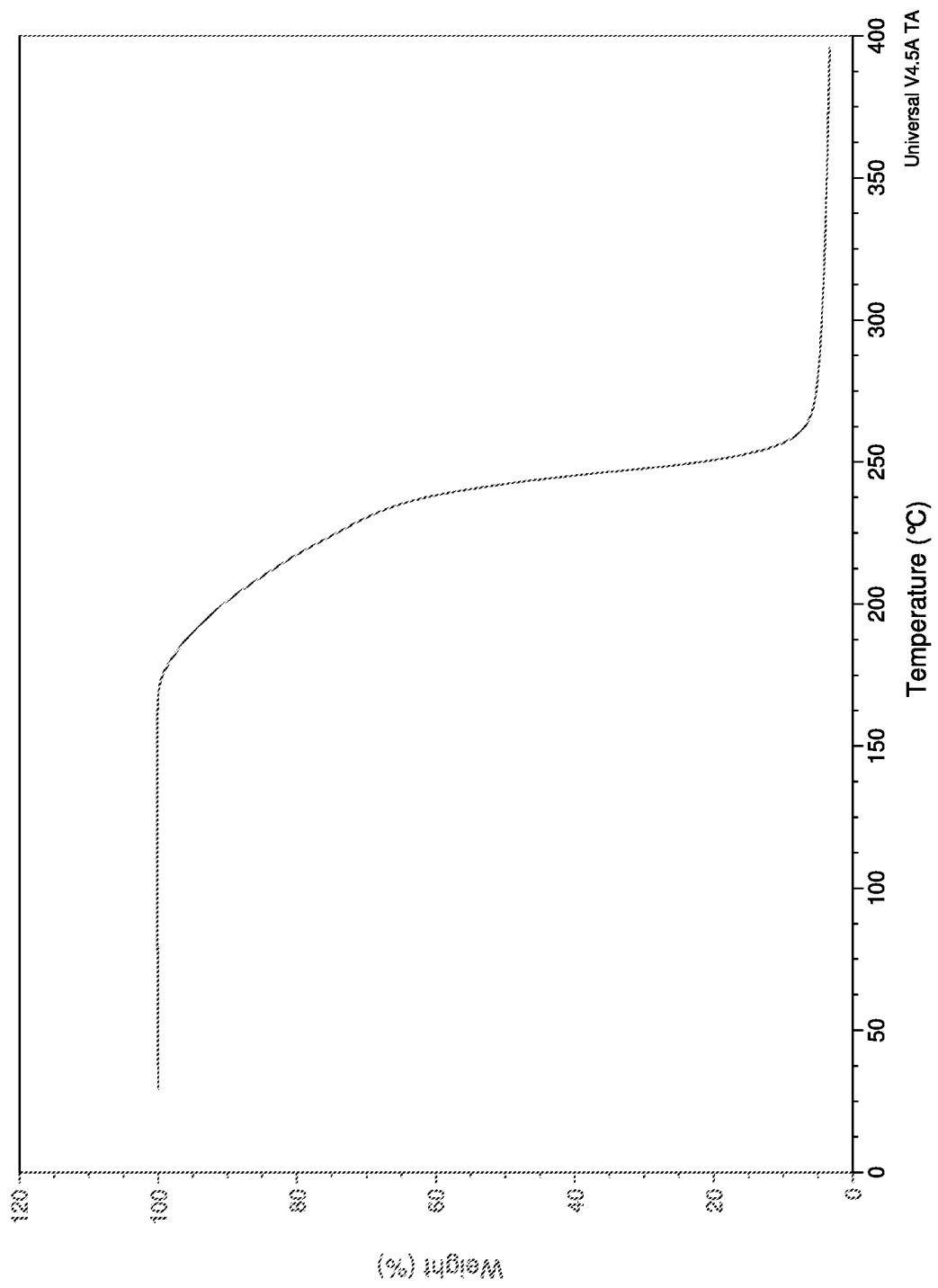
FIG. 17 shows a TGA profile of L-tartaric acid.
Figure 18:
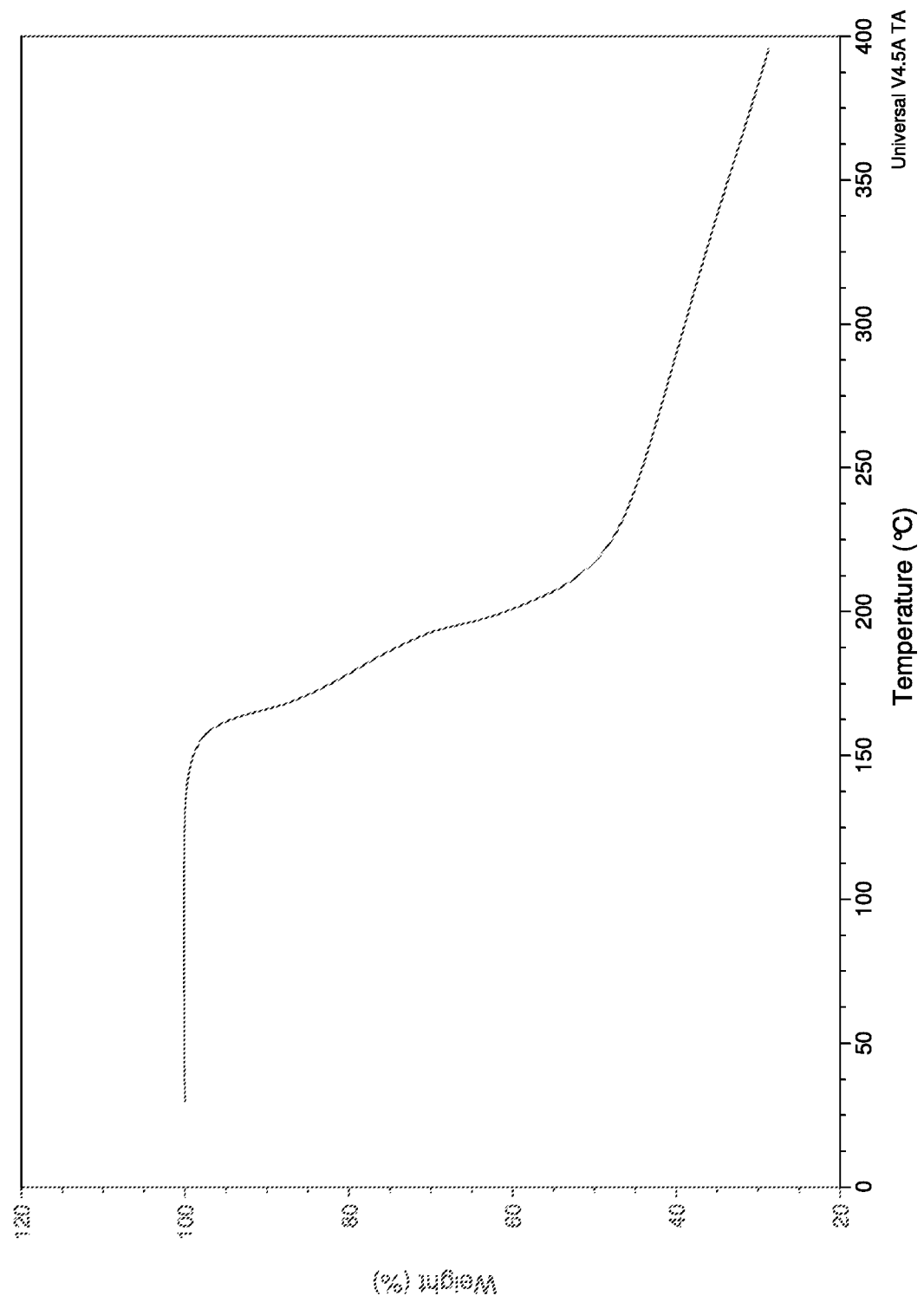
FIG. 18 shows a TGA profile confirming D-cycloserine L-tartarate (1:1) salt form.
Figure 19:
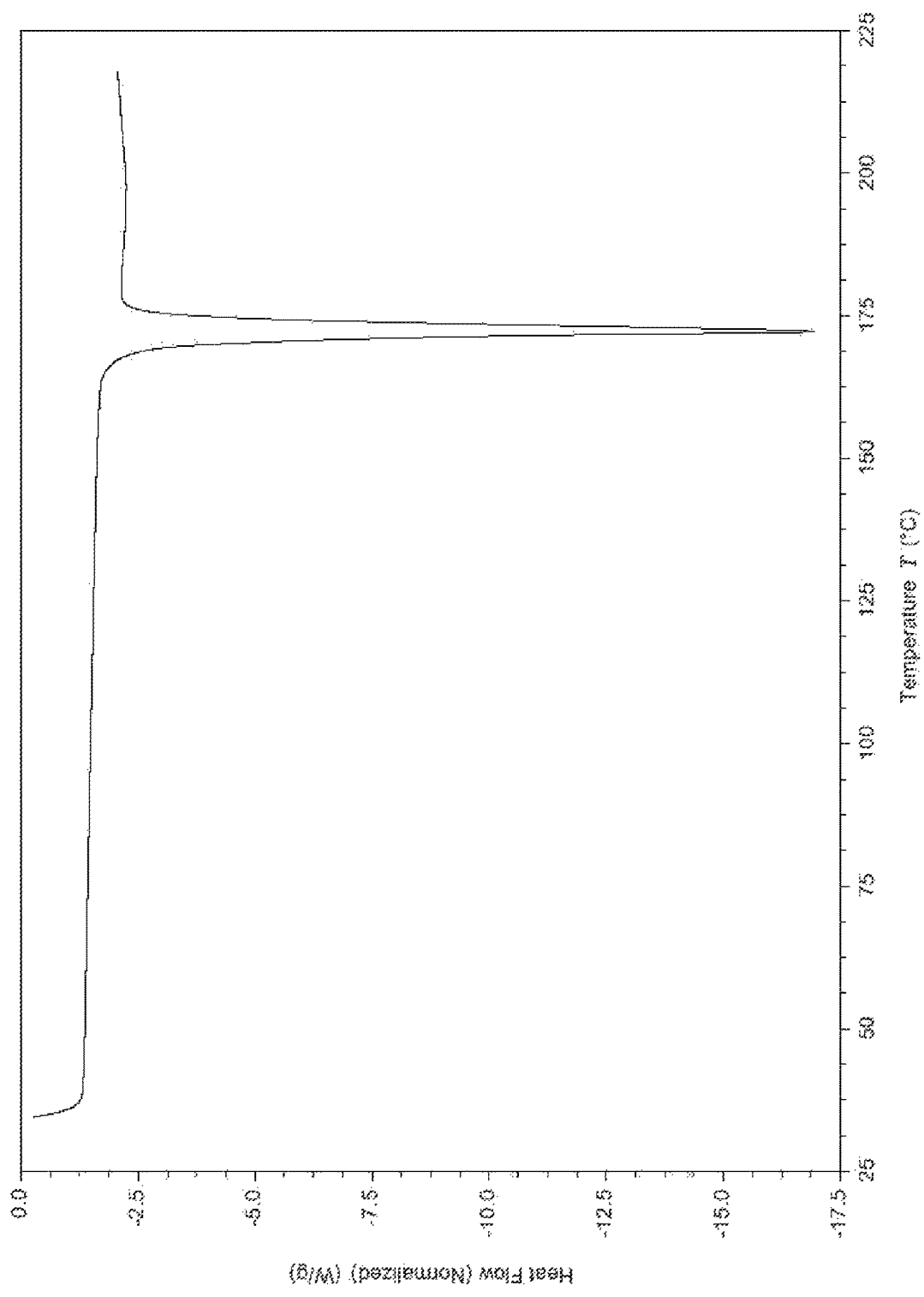
FIG. 19 shows a DSC profile of L-tartaric acid.
Figure 20:
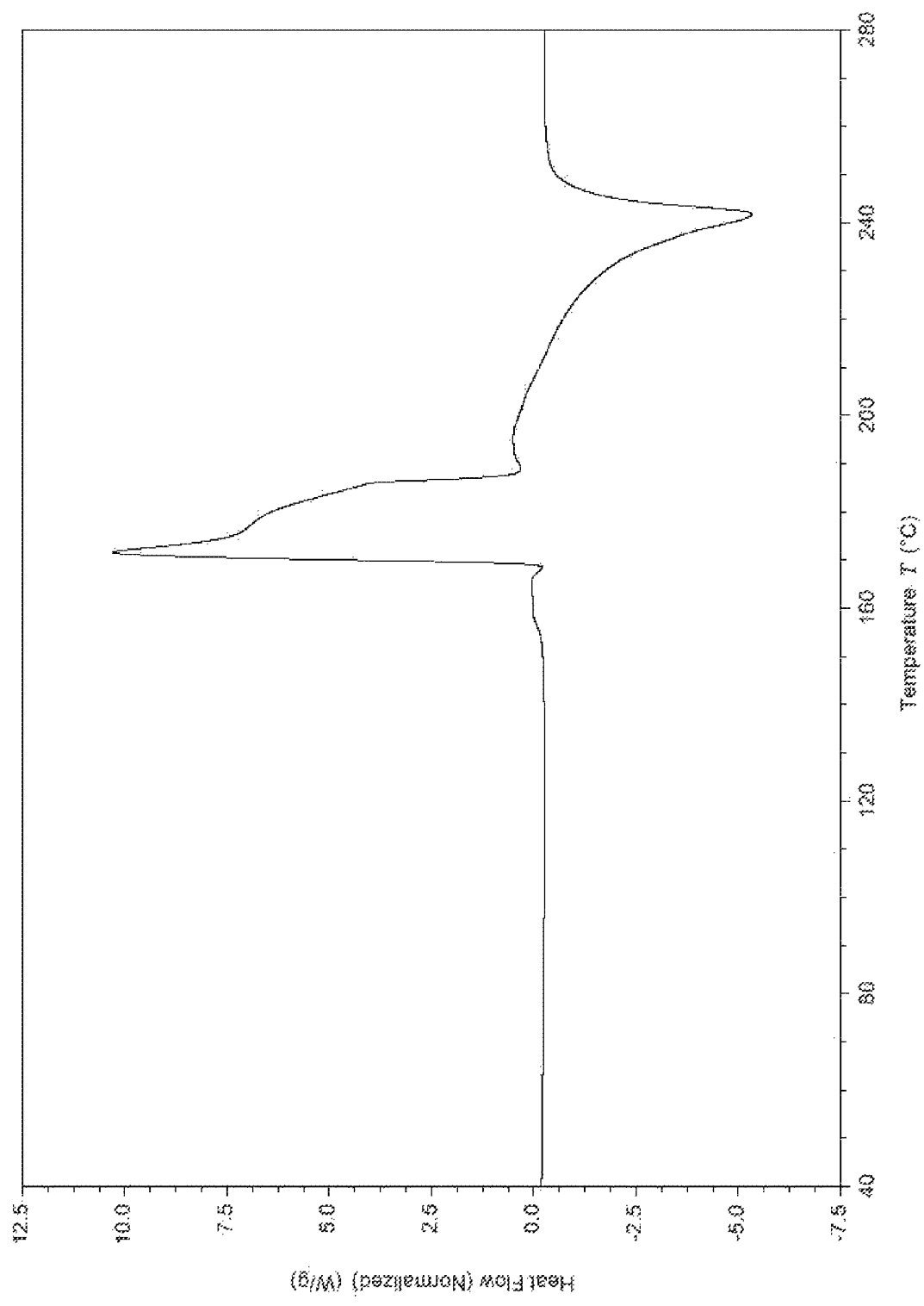
FIG. 20 shows a DSC profile confirming D-cycloserine L-tartarate (1:1) salt form.
Figure 21:
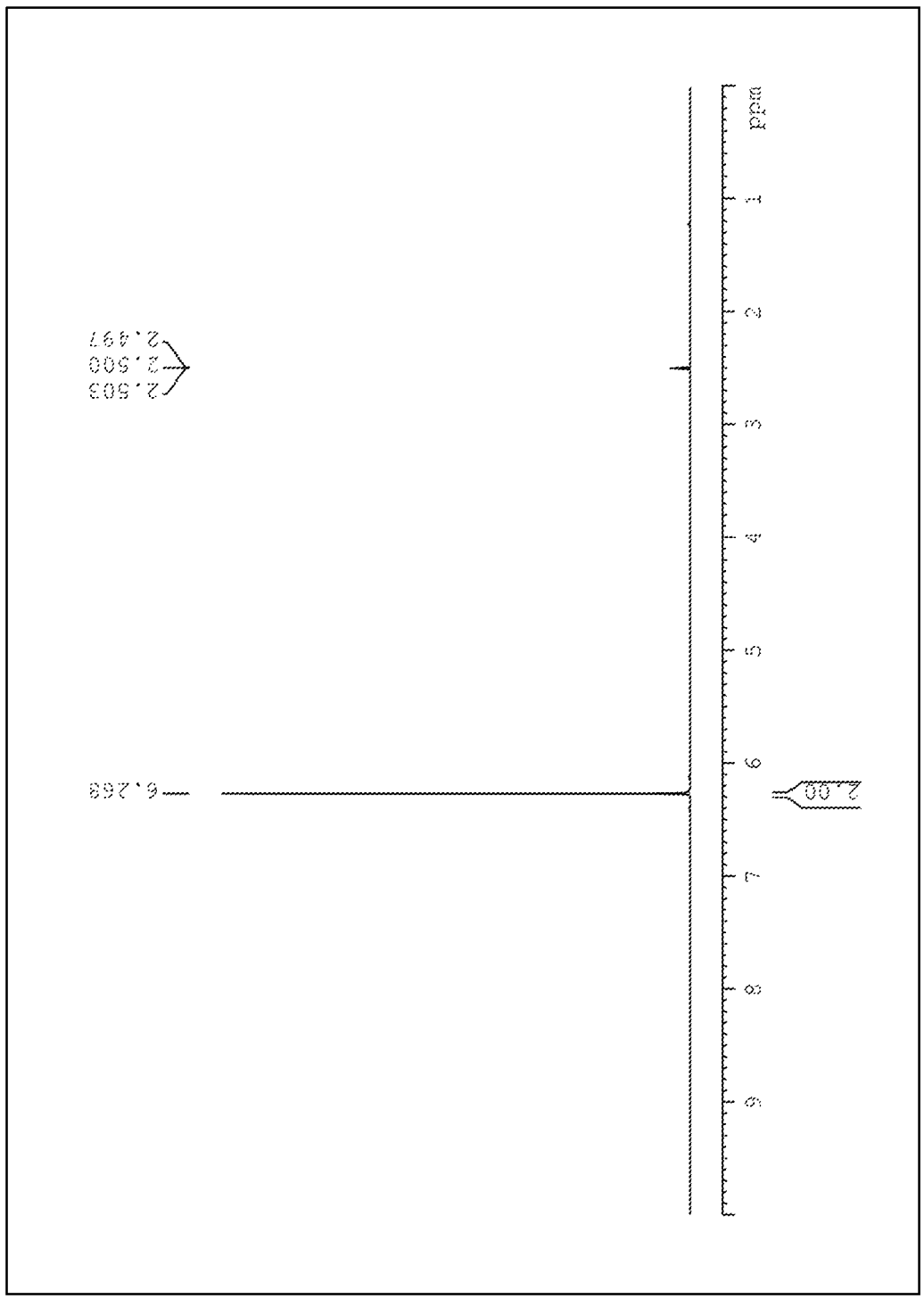
FIG. 21 shows a $^1$H-NMR spectrum of maleic acid.
Figure 22:
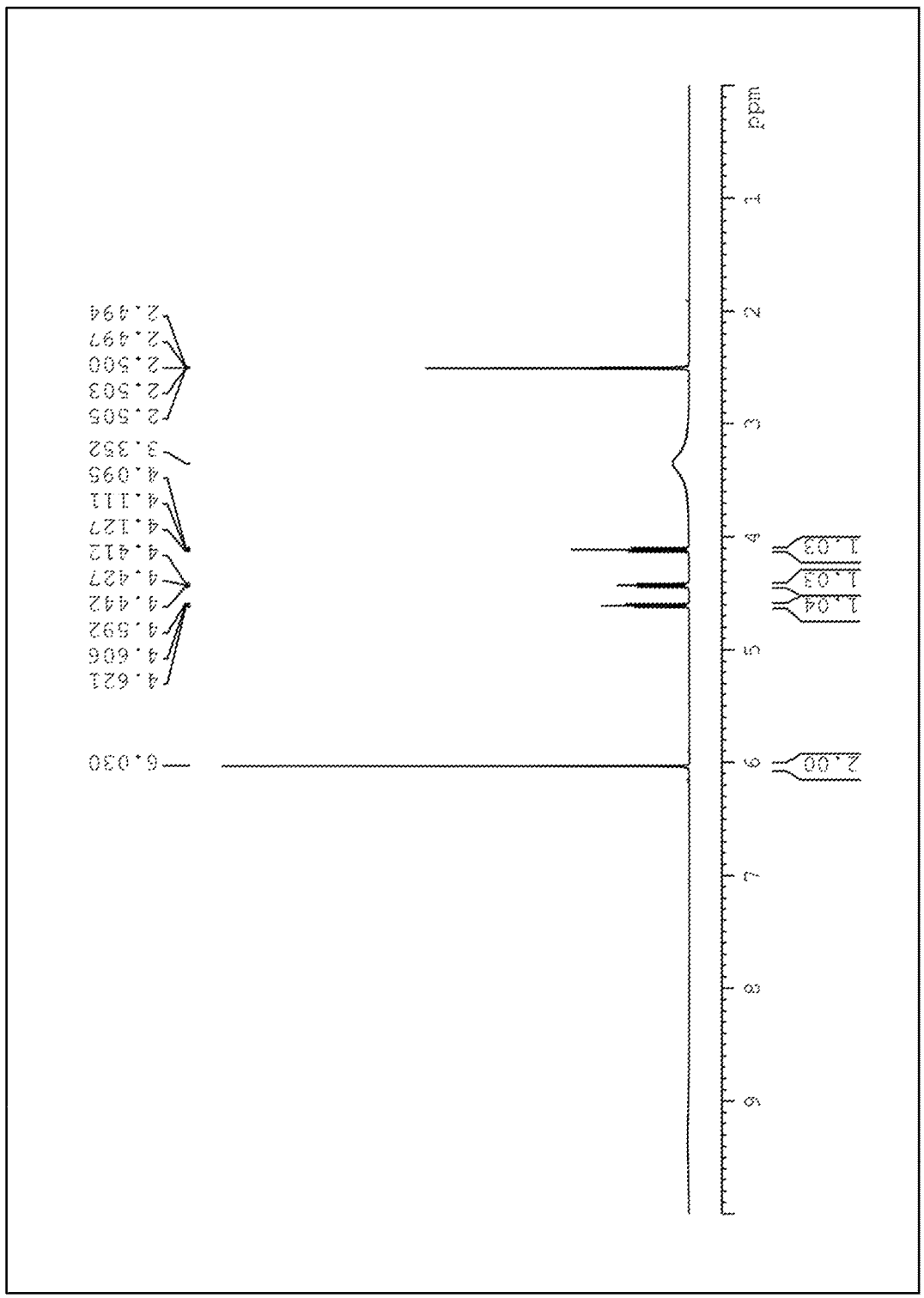
FIG. 22 shows a $^1$H-NMR spectrum confirming D-cycloserine maleate (1:1) salt form.
Figure 23:
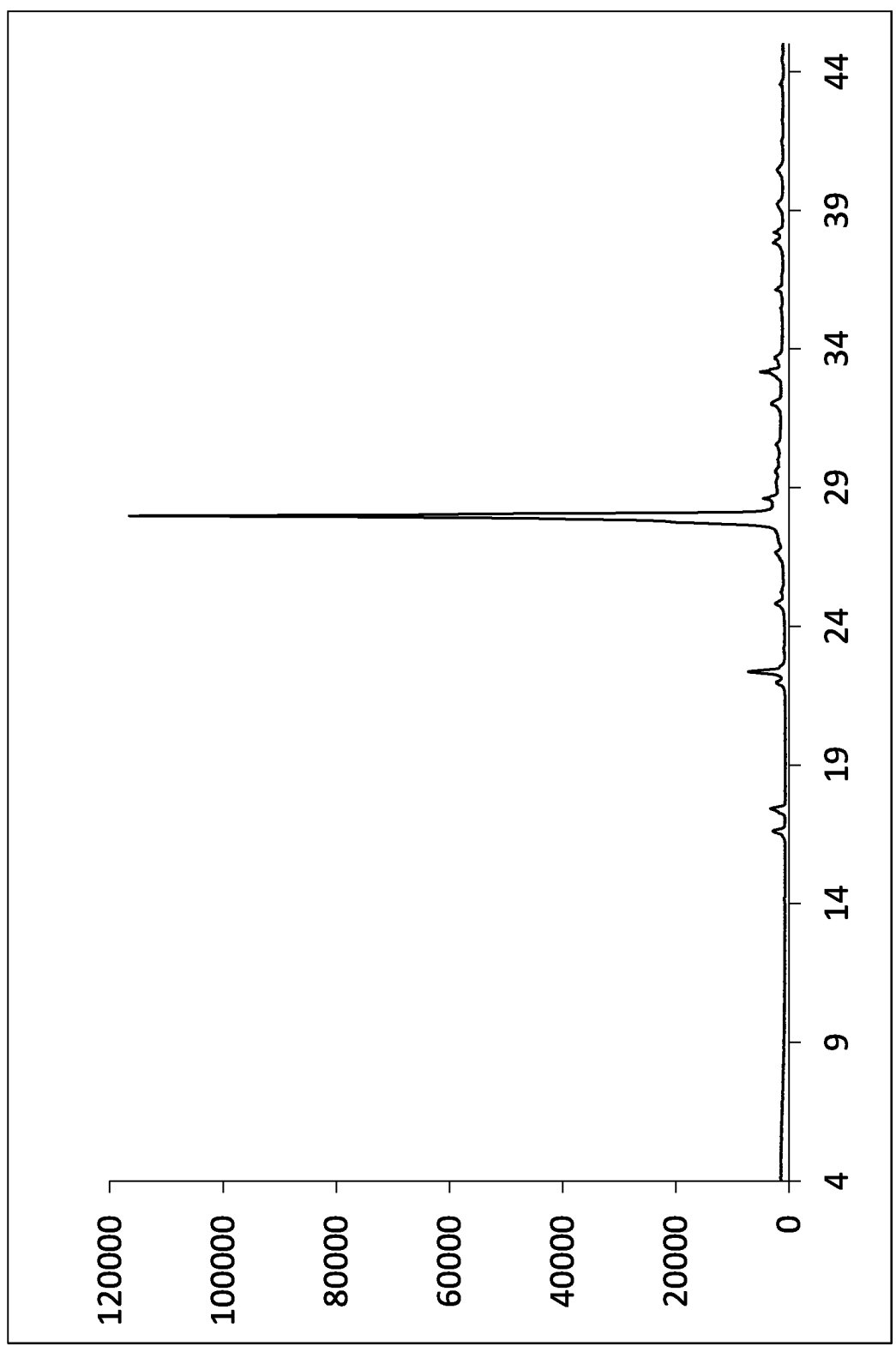
FIG. 23 shows an XRPD spectrum of maleic acid.
Figure 24:
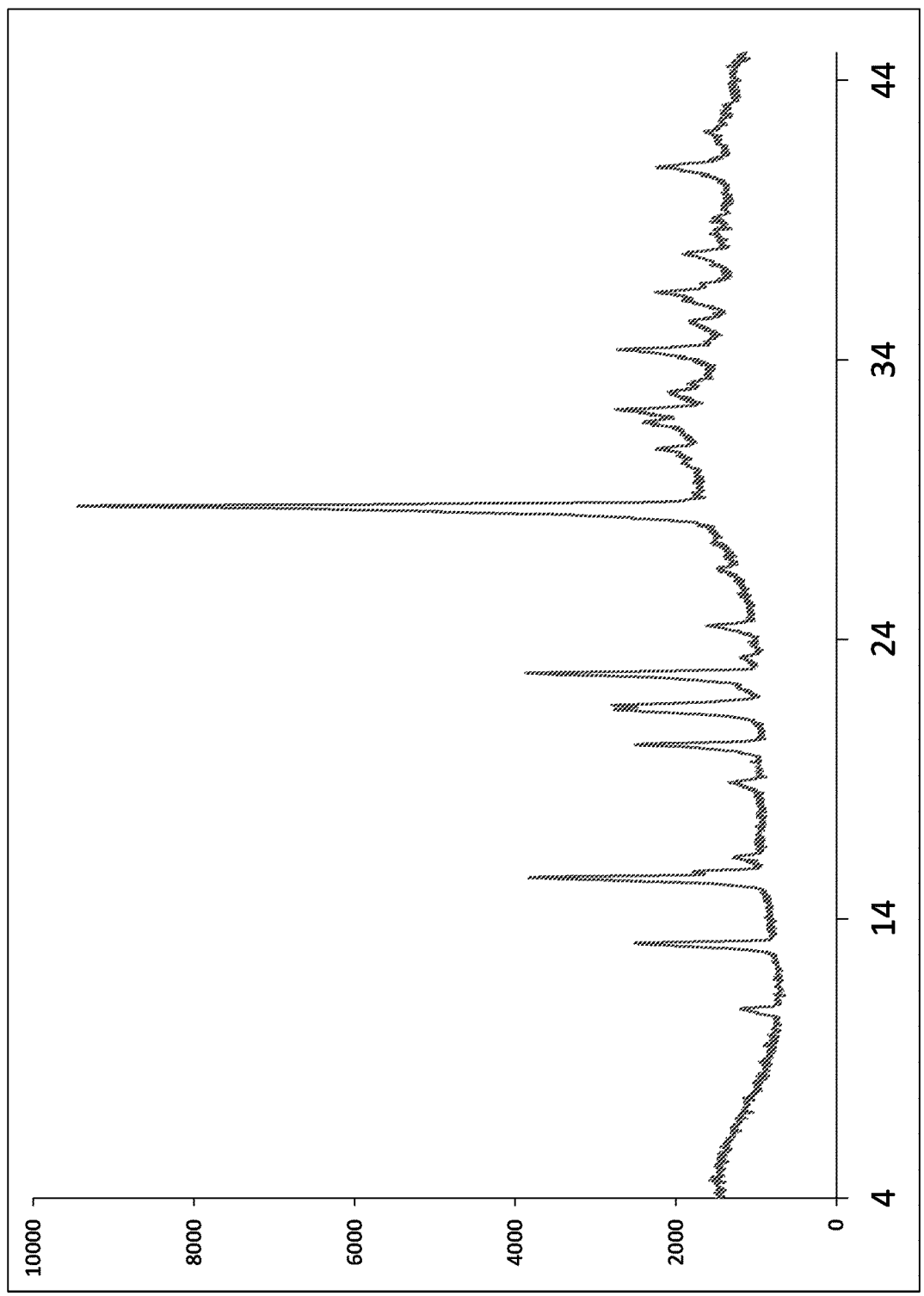
FIG. 24 shows an XRPD spectrum confirming D-cycloserine maleate (1:1) salt form.
Figure 25:
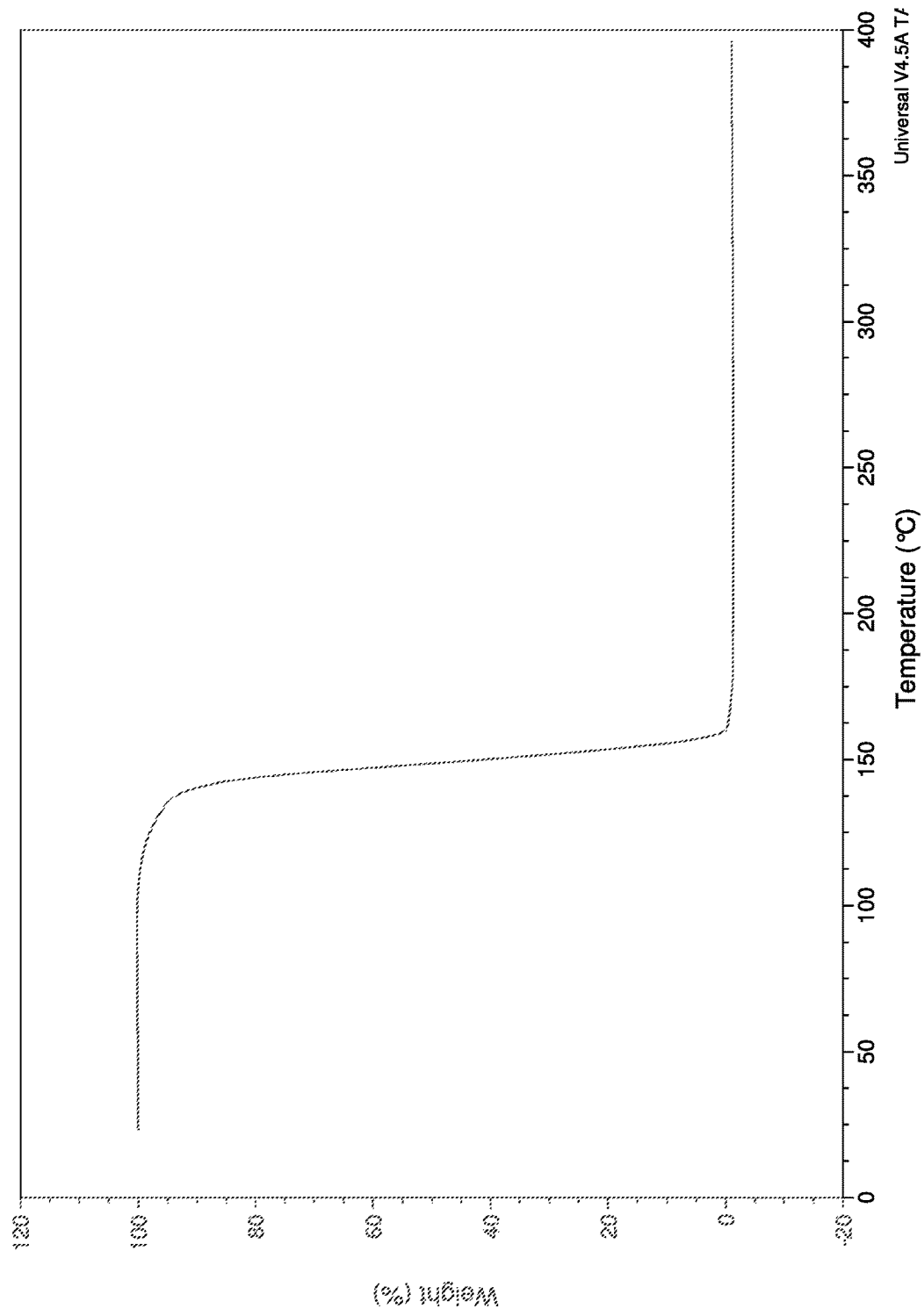
FIG. 25 shows a TGA profile of maleic acid.
Figure 26:
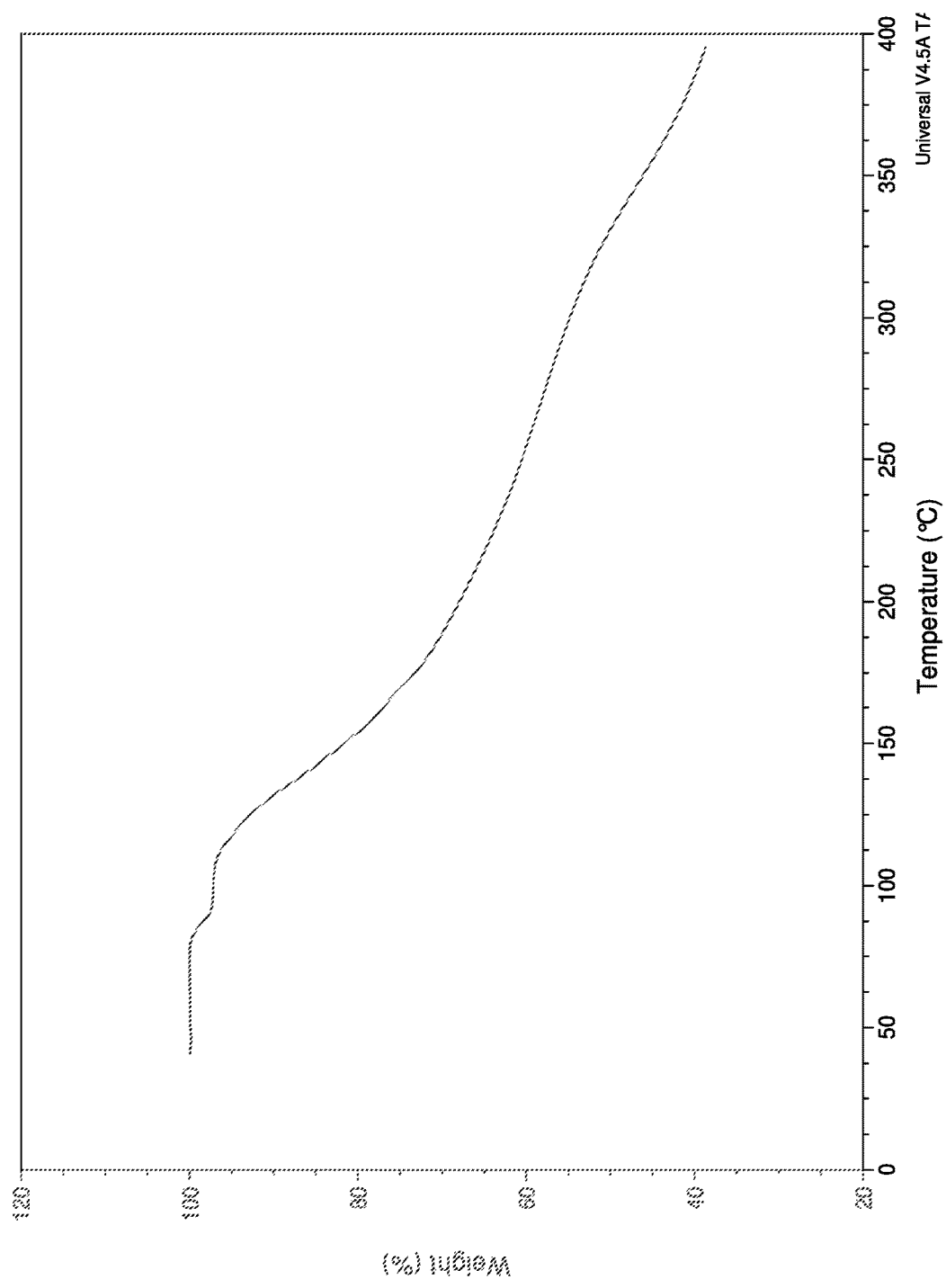
FIG. 26 shows a TGA profile confirming D-cycloserine maleate (1:1) salt form.
Figure 27:
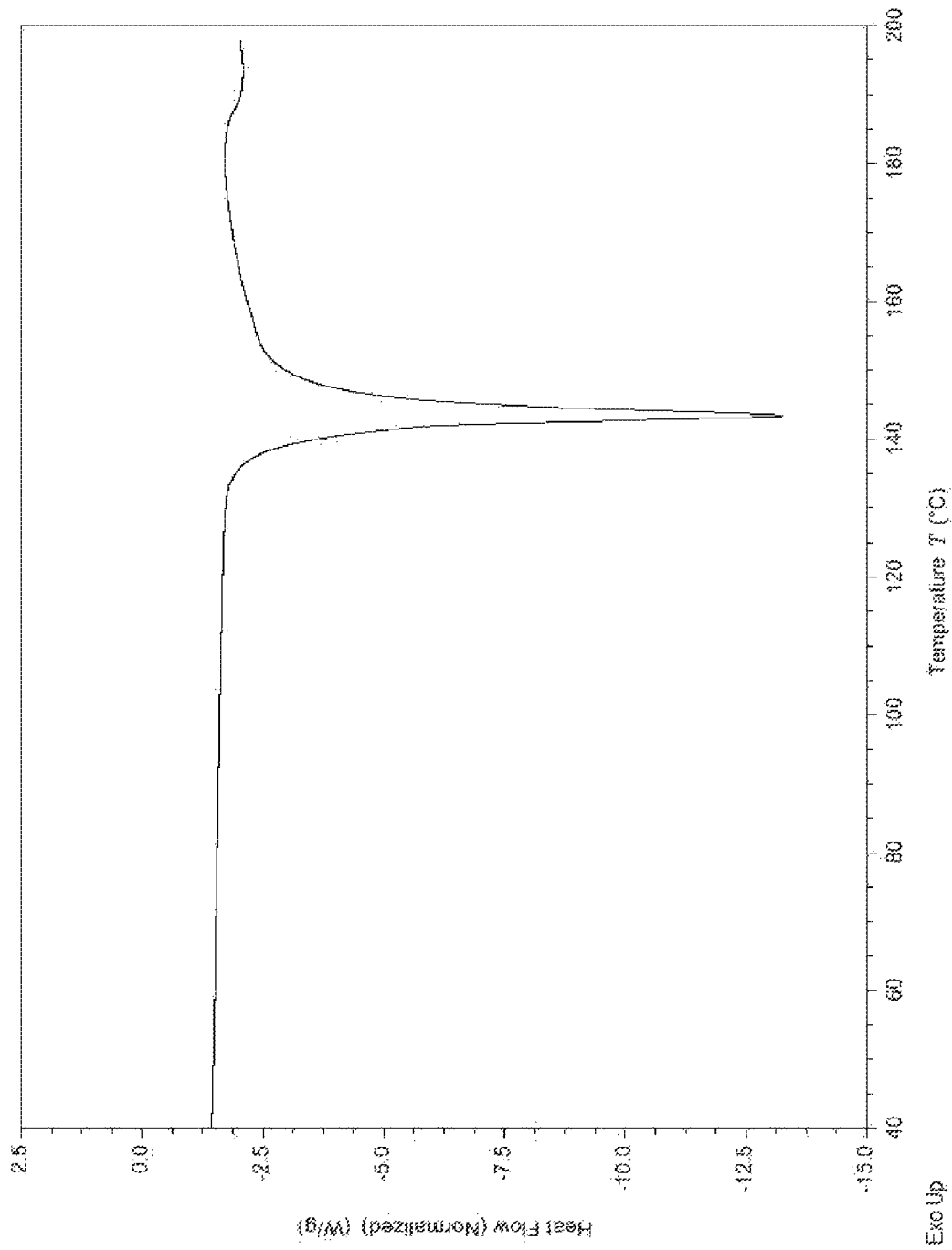
FIG. 27 shows a DSC profile of maleic acid.
Figure 28:
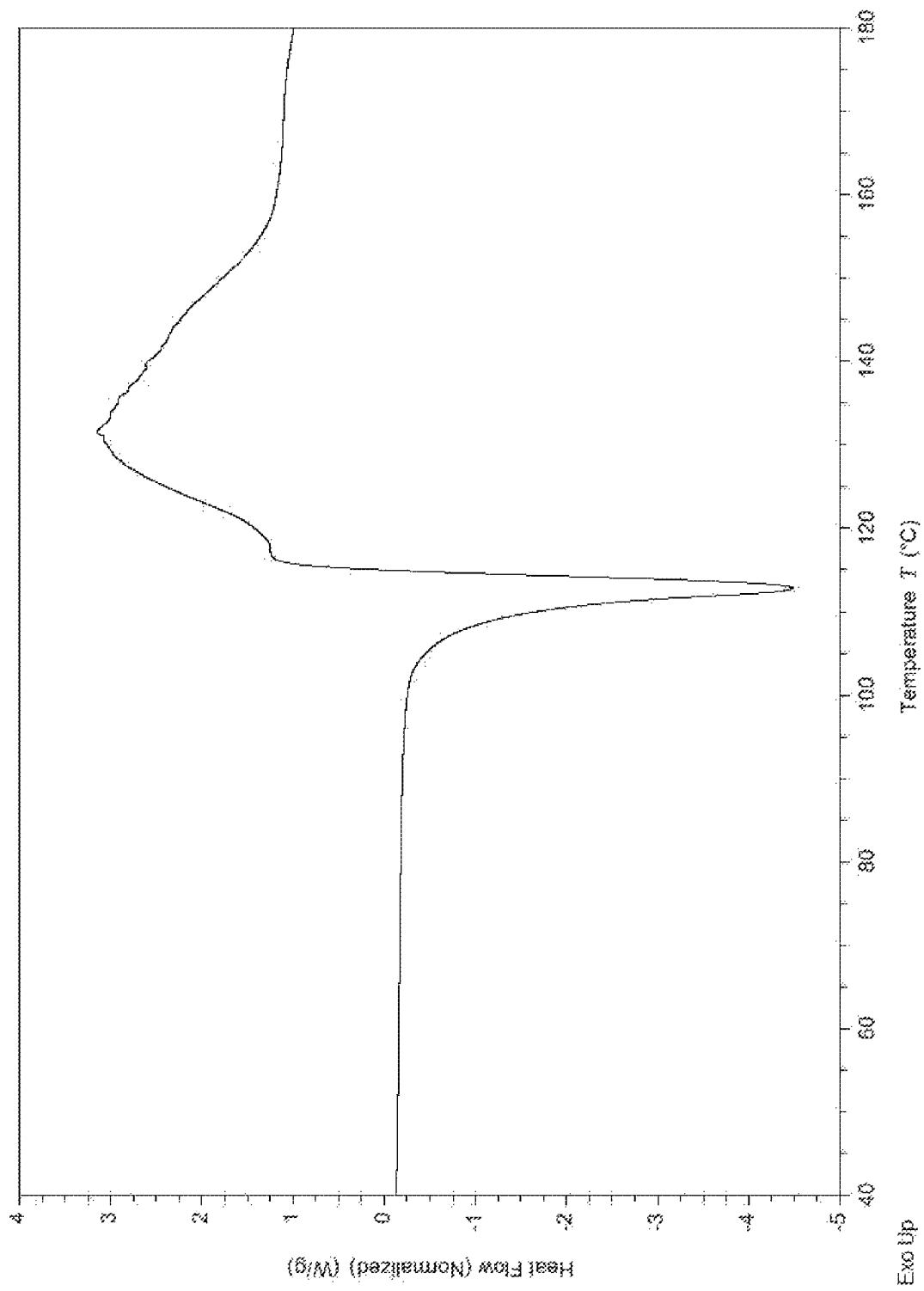
FIG. 28 shows a DSC profile confirming D-cycloserine maleate (1:1) salt form.
Figure 29:
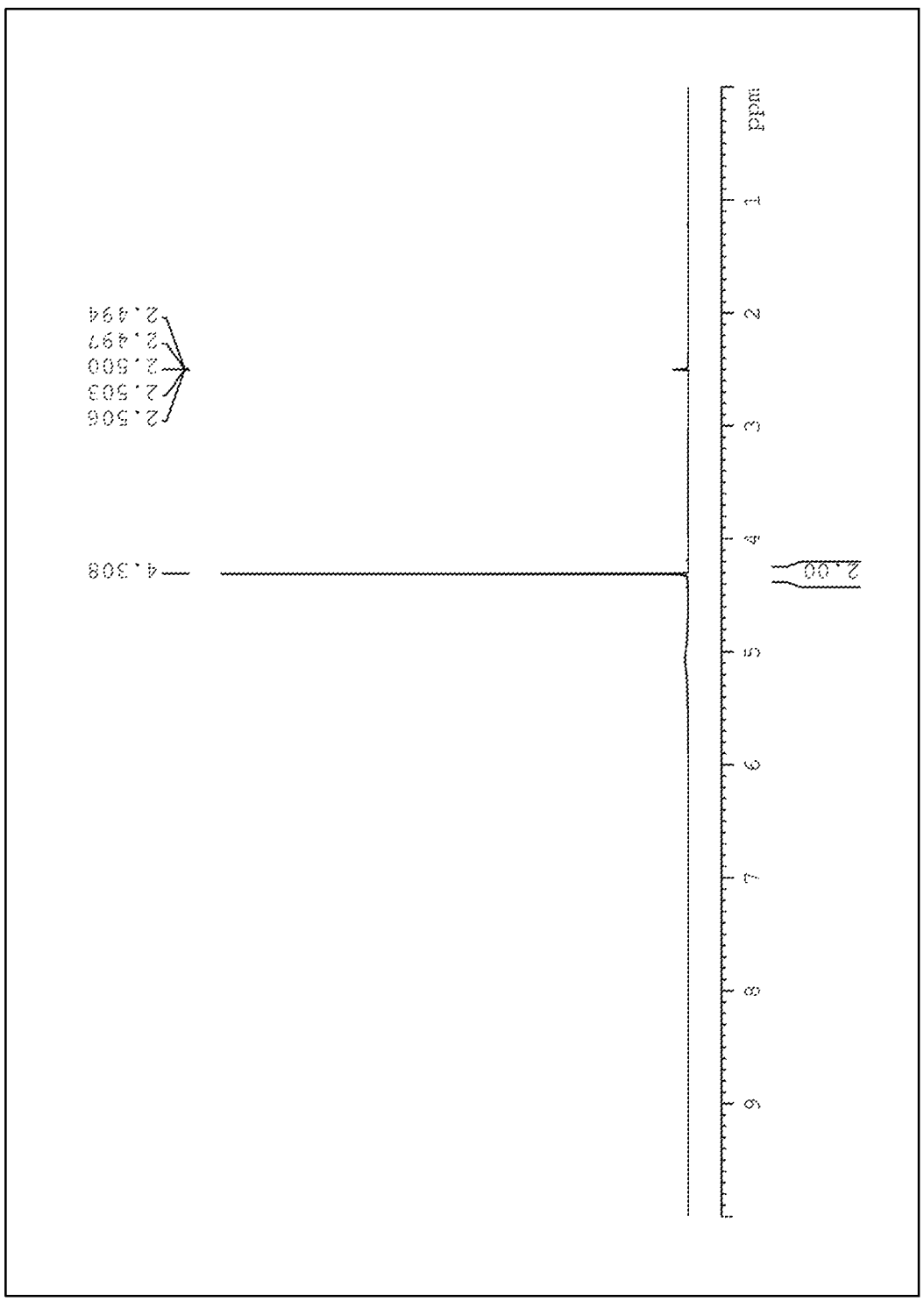
FIG. 29 shows a $^1$H-NMR spectrum of D-tartaric acid.
Figure 30:
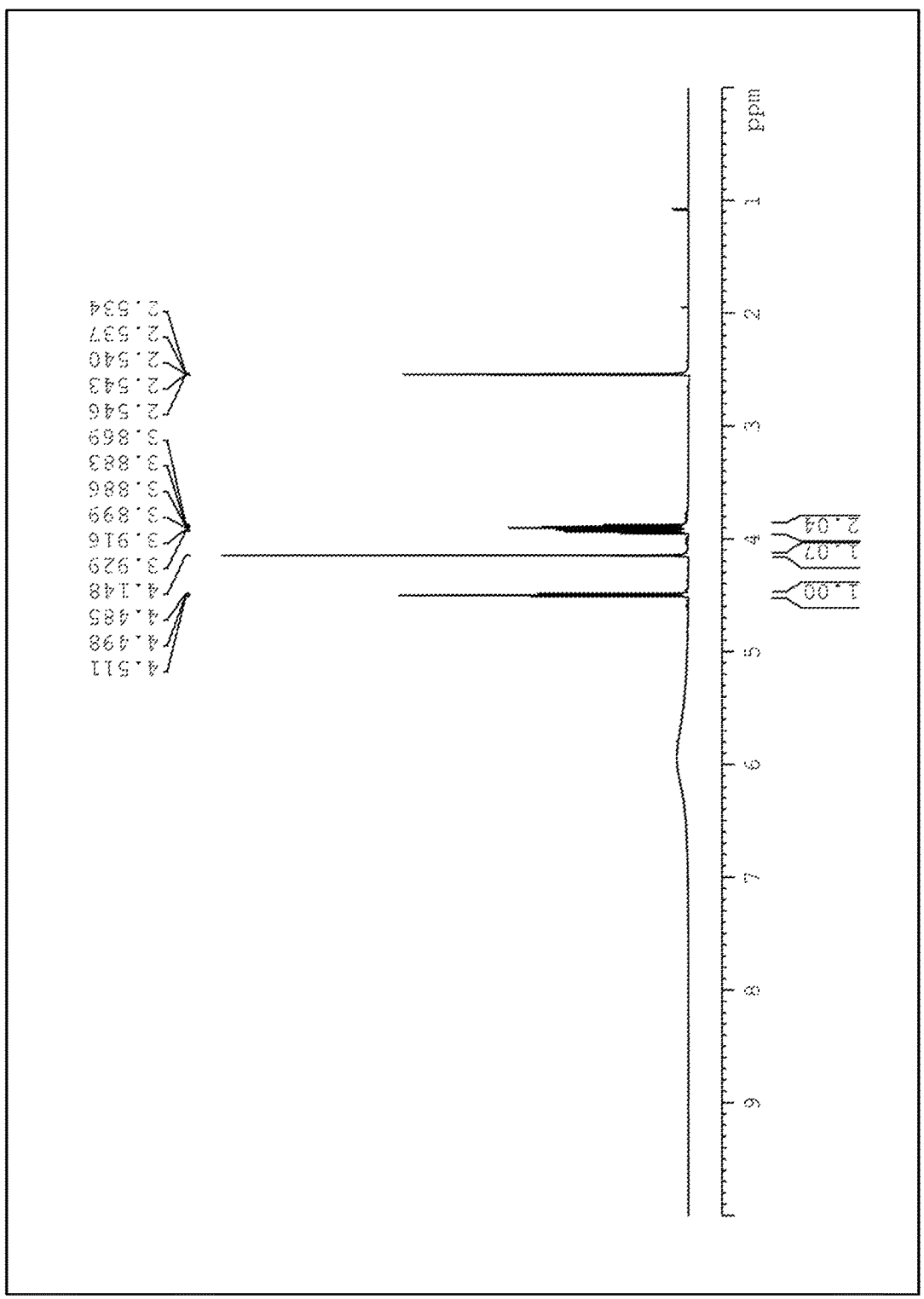
FIG. 30 shows a $^1$H-NMR spectrum confirming D-cycloserine D-tartarate (2:1) salt form.
Figure 31:
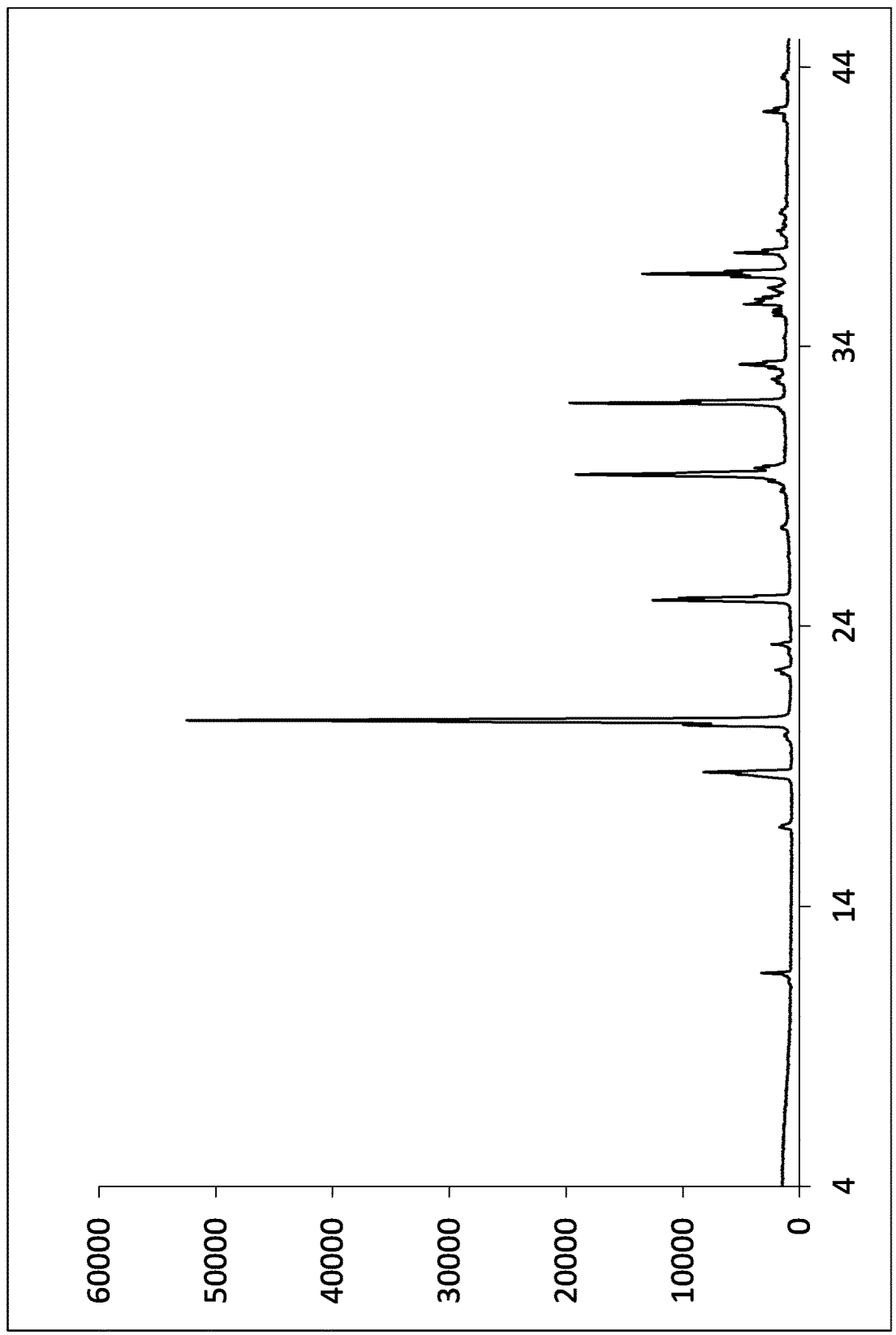
FIG. 31 shows a XRPD spectrum of D-tartaric acid.
Figure 32:
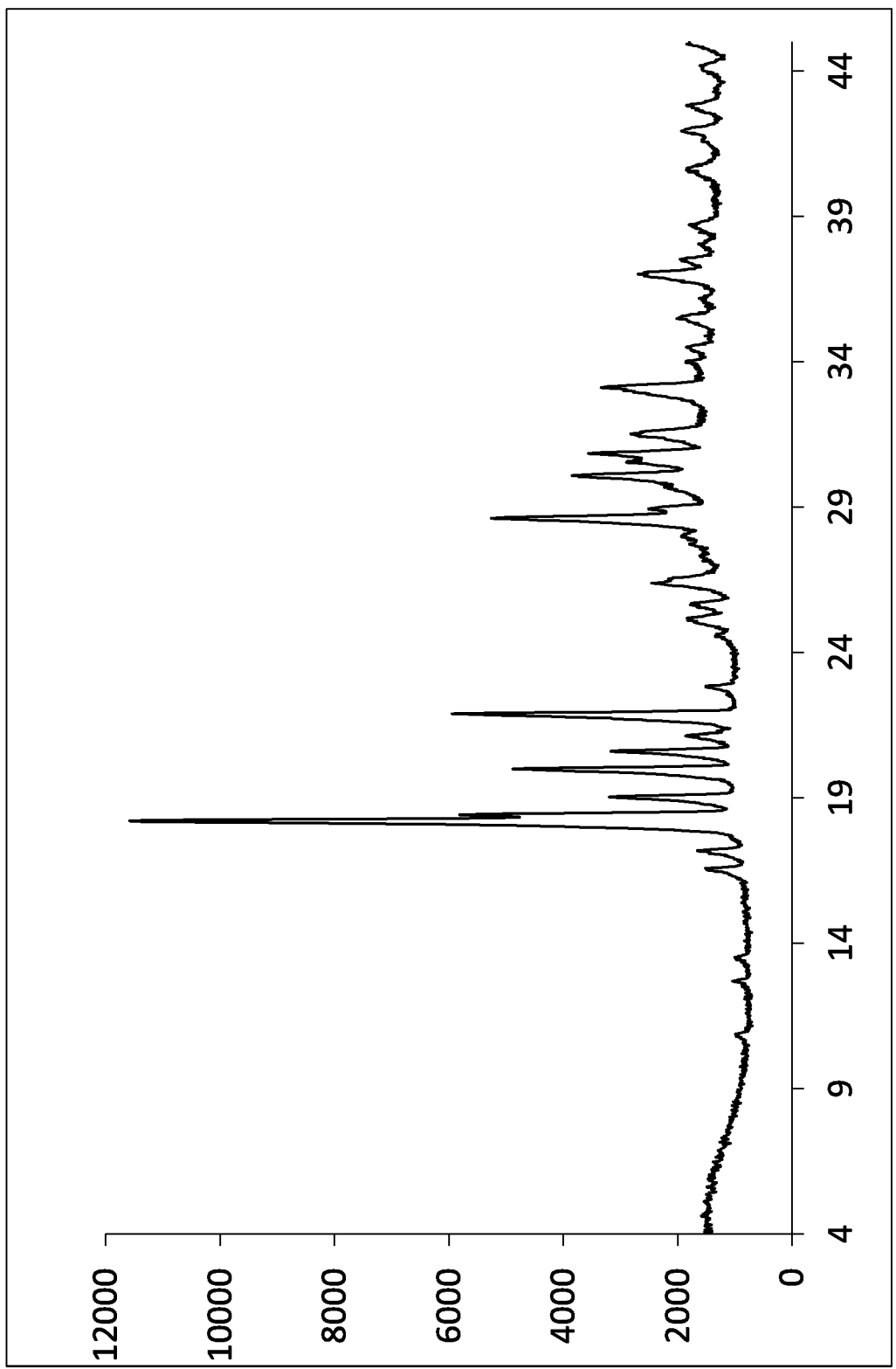
FIG. 32 shows a XRPD spectrum confirming D-cycloserine D-tartarate (2:1) salt form.
Figure 33:
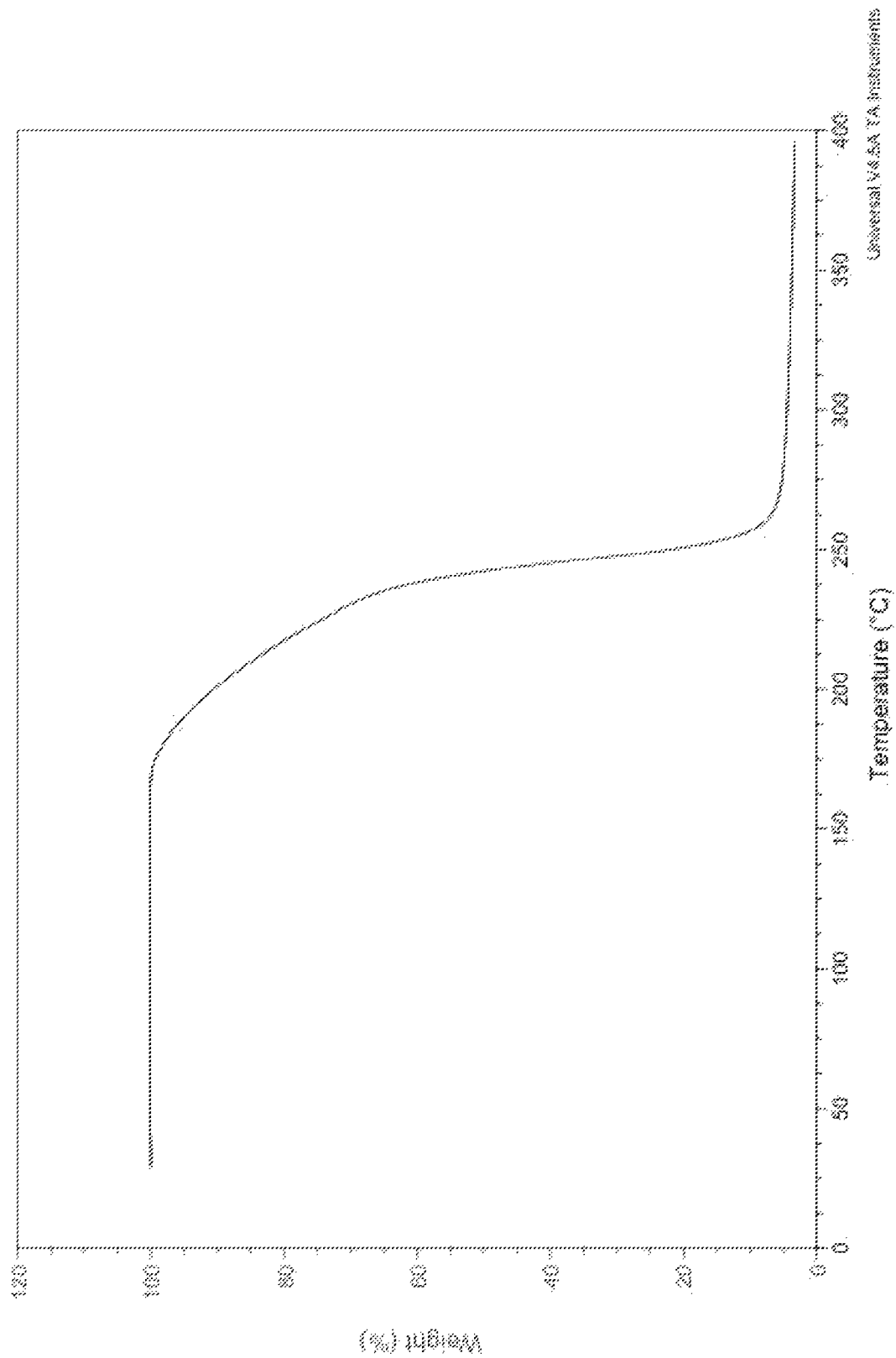
FIG. 33 shows a TGA profile of D-tartaric acid.
Figure 34:
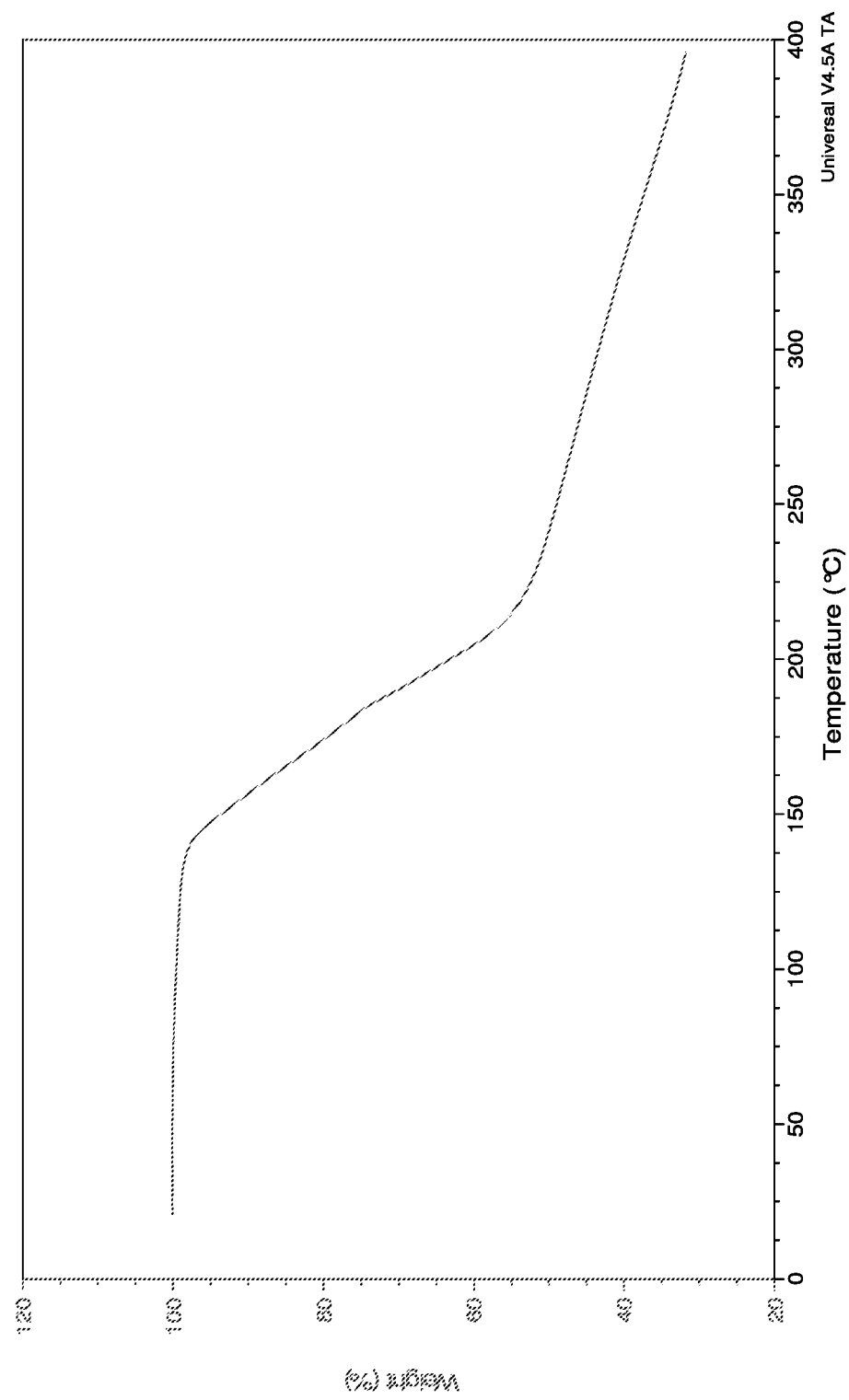
FIG. 34 shows a TGA profile confirming D-cycloserine D-tartarate (2:1) salt form.
Figure 35:
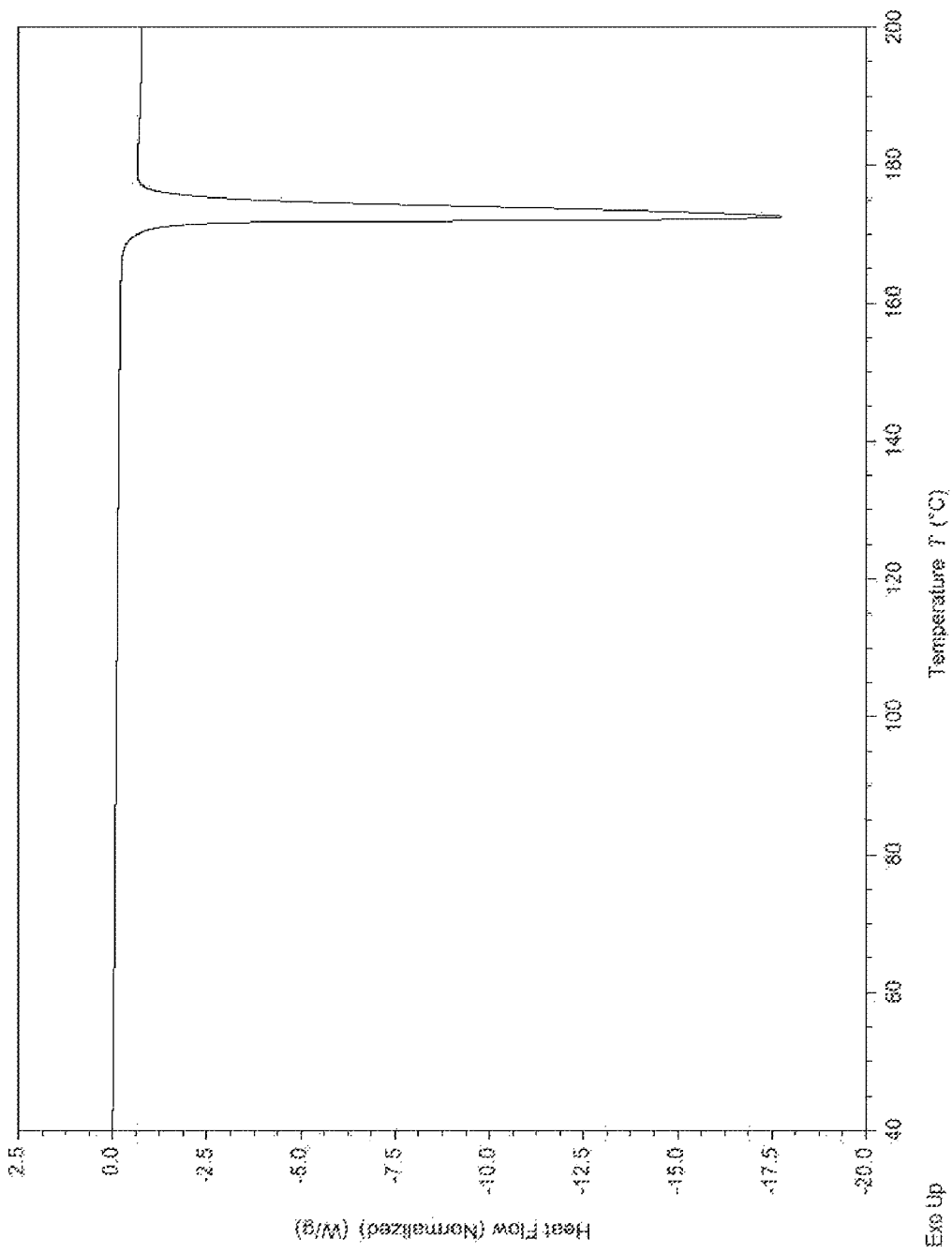
FIG. 35 shows a DSC profile of D-tartaric acid.
Figure 36:
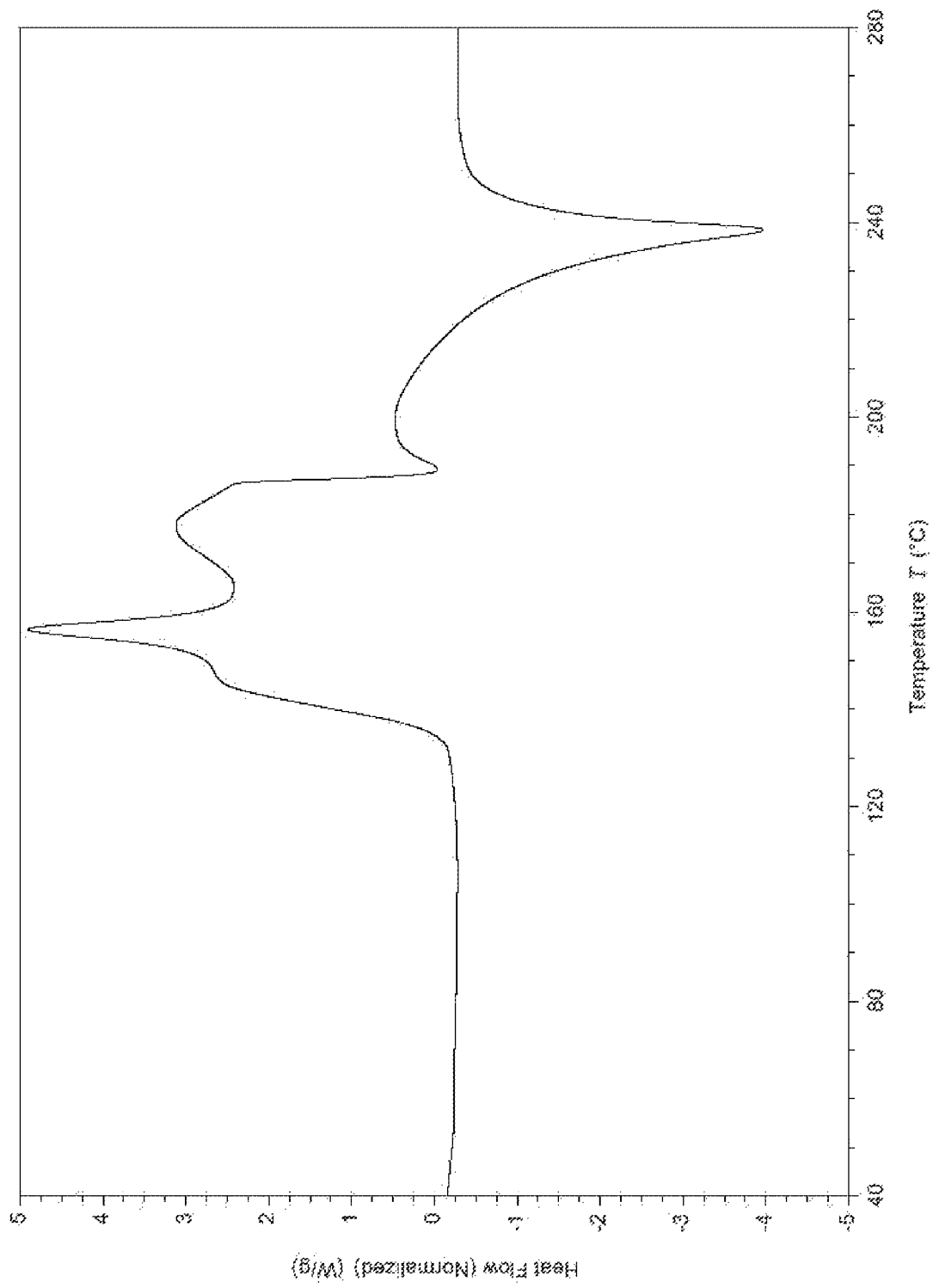
FIG. 36 shows a DSC profile confirming D-cycloserine D-tartarate (2:1) salt form.

This disclosure provides a salt of formula [A][B], in which [A] is a cation form of a cycloserine compound, and in which [B] is an anion form of a compound of formula (I) described herein. This salt or composition thereof can be used for treating a neuropsychiatric disorder or bacterial infection in a subject.

Salts of a Cation Form of a Cycloserine Compound and an Anion Form of a Compound of Formula (I)

One aspect of the present invention provides a salt of formula [A][B]. [A] is a cation form of a cycloserine compound and [B] is an anion form of a compound of formula (I):

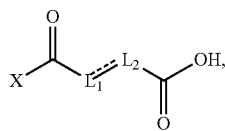

(I)

wherein X is —NH$_2$ or —OH;

each of L$_1$ and L$_2$, independently, is C$_{1-6}$ alkylene, C$_{2-6}$ alkenylene, or C$_{2-6}$ alkynylene, or one of L$_1$ and L$_2$ is N, O, or S, and the other one is C$_{1-6}$ alkylene, C$_{2-6}$ alkenylene, or C$_{2-6}$ alkynylene, as valency permits;

==== is either a single or double bond; and the ratio of [A] and [B] in the salt ranges from 10:1 to 1:10.

In some embodiments, X is —NH$_2$. In some embodiments, X is —OH.

In some embodiments, each of L$_1$ and L$_2$, independently, is C$_{1-6}$ alkylene, C$_{2-6}$ alkenylene, or C$_{2-6}$ alkynylene, or one of L$_1$ and L$_2$ is N, O, or S, and the other one is C$_{1-6}$ alkylene, C$_{2-6}$ alkenylene, or C$_{2-6}$ alkynylene, as valency permits. In some embodiments, each of L$_1$ and L$_2$, independently, is C$_{1-6}$ alkylene, C$_{2-6}$ alkenylene, or C$_{2-6}$ alkynylene, wherein each of C$_{1-6}$ alkylene, C$_{2-6}$ alkenylene, or C$_{2-6}$ alkynylene. In some embodiments, each of L$_1$ and L$_2$, independently, is C$_{1-6}$ alkylene, C$_{2-6}$ alkenylene, or C$_{2-6}$ alkynylene. In some embodiments, one of L$_1$ and L$_2$ is N, O, or S, and the other one is C$_{1-6}$ alkylene, C$_{2-6}$ alkenylene, or C$_{2-6}$ alkynylene, as valency permits. In some embodiments, at least one of L$_1$ and L$_2$ is C$_{1-6}$ alkylene, C$_{2-6}$ alkenylene, or C$_{2-6}$ alkynylene. As disclosed herein, C$_{1-6}$ alkylene, C$_{2-6}$ alkenylene, or C$_{2-6}$ alkynylene can be either unsubstituted or optionally substituted with halogen, —CN, —NO$_2$, —OH, —O(C$_{1-6}$ alkyl), —NH$_2$, or —N$_3$.

In some embodiments, at least one of L$_1$ and L$_2$ is C$_{1-6}$ alkylene, which may be substituted or unsubstituted C$_{1-6}$ alkylene. In some embodiments, at least one of L$_1$ and L$_2$ is methylene, which may be substituted or unsubstituted methylene. In some embodiments, at least one of L$_1$ and L$_2$ is methylene. As used herein, methylene can be either unsubstituted or optionally substituted with halogen, —CN, —NO$_2$, —OH, —O(C$_{1-6}$ alkyl), or —NH$_2$. In some embodiments, at least one of L$_1$ and L$_2$ is methylene. In some embodiments, each of L$_1$ and L$_2$ is methylene substituted with halogen, —CN, —NO$_2$, —OH, —O(C$_{1-6}$ alkyl), or —NH$_2$. In some embodiments, each of L$_1$ and L$_2$ is methylene substituted with —OH. In some embodiments, at least one of L$_1$ and L$_2$ is unsubstituted methylene. In some embodiments, both L$_1$ and L$_2$ are methylene, which both may be substituted methylene or both may be unsubstituted methylene. In some embodiments, at least one of L$_1$ and L$_2$ is C$_{2-6}$ alkenylene, which may be substituted or unsubstituted C$_{2-6}$ alkenylene. In some embodiments, at least one of L$_1$ and L$_2$ is C$_{2-6}$ alkynylene, which may be substituted or unsubstituted C$_{2-6}$ alkynylene.

In some embodiments, X is —OH; and ==== is a single bond. In some embodiments, X is —OH; ==== is a single bond; and each of L$_1$ and L$_2$ is methylene substituted with —OH. In some embodiments, X is —OH; ==== is a double bond; and each of L$_1$ and L$_2$ is optionally substituted methylene.

In some embodiments, at least one of L$_1$ and L$_2$ is N, O, or S, and the other one is C$_{1-6}$ alkylene, C$_{2-6}$ alkenylene, or C$_{2-6}$ alkynylene, as valency permits. In some embodiments, at least one of L$_1$ and L$_2$ is N and the other one is C$_{1-6}$ alkylene, C$_{2-6}$ alkenylene, or C$_{2-6}$ alkynylene, as valency permits. In some embodiments, at least one of L$_1$ and L$_2$ is substituted N and the other one is C$_{1-6}$ alkylene, C$_{2-6}$ alkenylene, or C$_{2-6}$ alkynylene, as valency permits. In some embodiments, at least one of L$_1$ and L$_2$ is O and the other one is C$_{1-6}$ alkylene, C$_{2-6}$ alkenylene, or C$_{2-6}$ alkynylene, as valency permits. In some embodiments, at least one of L$_1$ and L$_2$ is S and the other one is C$_{1-6}$ alkylene, C$_{2-6}$ alkenylene, or C$_{2-6}$ alkynylene, as valency permits.

In some embodiments, ==== is a single bond. In some embodiments, ==== is a double bond.

In some embodiments, the ratio of [A] and [B] in the salt ranges from 10:1 to 1:10, 9:1 to 1:9, 8:1 to 1:8, 7:1 to 1:7, 6:1 to 1:6, 5:1 to 1:5, 4:1 to 1:4, 3:1 to 1:3, 2:1 to 1:2, or 2:1 to 1:1, wherein [A] is a cation form of a cycloserine compound and [B] is an anion form of a compound of formula (I):

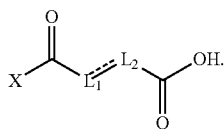
(I)

In some embodiments, the ratio of [A] and [B] in the salt ranges from 10:1 to 1:10. In some embodiments, the ratio of [A] and [B] in the salt ranges from 9:1 to 1:9. In some embodiments, the ratio of [A] and [B] in the salt ranges from 8:1 to 1:8. In some embodiments, the ratio of [A] and [B] in the salt ranges from 7:1 to 1:7. In some embodiments, the ratio of [A] and [B] in the salt ranges from 6:1 to 1:6. In some embodiments, the ratio of [A] and [B] in the salt ranges from 5:1 to 1:5. In some embodiments, the ratio of [A] and [B] in the salt ranges from 4:1 to 1:4. In some embodiments, the ratio of [A] and [B] in the salt ranges from 3:1 to 1:3. In some embodiments, the ratio of [A] and [B] in the salt ranges from 2:1 to 1:2. In some embodiments, the ratio of [A] and [B] in the salt ranges from 2:1 to 1:1. In some embodiments, the ratio of [A] and [B] in the salt is 7:1, 6:1, 5:1, 4:1, 3:1, 2:1, or 1:1.

In some embodiments, the cycloserine compound is of formula:

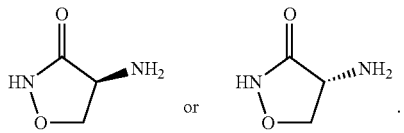 [SMILES: N[C@H]1CONC1=O ; N[C@@H]1CONC1=O]

In some embodiments, the cycloserine compound is:

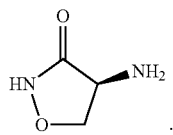

In some embodiments, the cycloserine compound is:

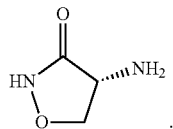

In some embodiments, the compound of formula (I) is of formula:

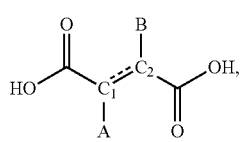
(Ia)

wherein each of A and B, independently, is —NH$_2$, —OH, or H; and
C$_1$═══C$_2$ is C$_1$-C$_2$ or C$_2$═C$_1$.

In some embodiments, at least one of A and B is —NH$_2$. In some embodiments, at least one of A and B is —OH. In some embodiments, A and B are both —OH. In some embodiments, the compound of formula (I) is succinic acid, D-tartaric acid, L-tartaric acid, meso-tartaric acid, fumaric acid, maleic acid, or malic acid.

In some embodiments, the compound of formula (Ia) is of formula:

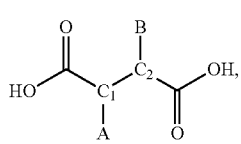
(Ib)

wherein each of A and B, independently, is —OH or —H. In some embodiments, at least one of A and B is —OH. In some embodiments, A and B are both —OH.

In some embodiments, the compound of formula (Ib) is:

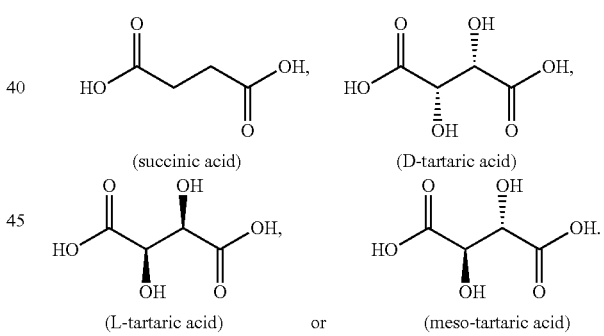

(succinic acid)     (D-tartaric acid)

(L-tartaric acid)   or   (meso-tartaric acid)

In some embodiments, the compound of formula (Ib) is selected from the group consisting of: succinic acid, D-tartaric acid, and L-tartaric acid. In some embodiments, the compound of formula (Ib) is selected from the group consisting of: succinic acid, D-tartaric acid, L-tartaric acid, and meso-tartaric acid, and the ratio between [A] and [B] ranges from 5:1 to 1:1. In some embodiments, the compound of formula (Ib) is

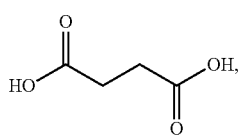

and the ratio between [A] and [B] is 4:1. In some embodiments, the compound of formula (Ib) is

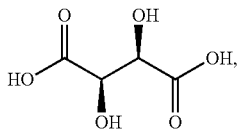

and the ratio between [A] and [B] is 2:1. In some embodiments, the compound of formula (Ib) is

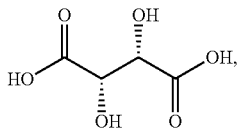

and the ratio between [A] and [B] is 1:1.

In some embodiments, the compound of formula (Ia) is a compound of formula (Ic):

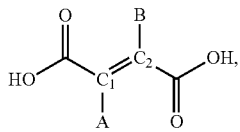

wherein each of A and B, independently, is —OH or —H. In some embodiments, at least one of A and B is —OH. In some embodiments, A and B are both —OH.

In some embodiments, the compound of formula (Ic) is selected from

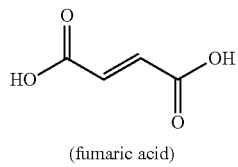
(fumaric acid)

j or

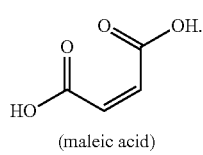
(maleic acid)

In some embodiments, the compound of formula (Ic) is fumaric acid. In some embodiments, the compound of formula (Ic) is maleic acid. In some embodiments, the compound of formula (Ic) is

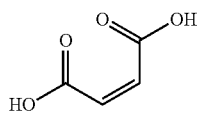

and the ratio between [A] and [B] described herein is 1:1.

Compositions

Another aspect of the present disclosure provides a composition comprising a salt of formula [A][B] as described herein and a carrier.

In some embodiments, the composition is a pharmaceutical composition, a nutraceutical composition, a health food, or a medical food.

In certain embodiments, the composition is a health food. In some embodiments, the compositions described herein can be a health food or a health food product, which can be any kinds of liquid and solid/semi-solid materials that are used for nourishing humans and animals, for improving basic behavioral functioning, hyperactivity, anxiety, depression, sensorimotor gating, pain threshold, memory and/or cognitive functioning, or for facilitating treatment of any of the target diseases noted herein (e.g., a neuropsychiatric disorder and/or a bacterial infectious disease (e.g., tuberculosis) including those described herein). The health food product may be a food product (e.g., tea-based beverages, juice, soft drinks, coffee, milk, jelly, cookies, cereals, chocolates, snack bars, herbal extracts, dairy products (e.g., ice cream, and yogurt)), a food/dietary supplement, or a nutraceutical formulation.

The health food product described herein, may comprise one or more edible carriers, which confer one or more of the benefits to the product as described herein. Examples of edible carriers include starch, cyclodextrin, maltodextrin, methylcellulose, carbon methoxy cellulose, xanthan gum, and aqueous solutions thereof. Other examples include solvents, dispersion media, coatings, surfactants, antioxidants, preservatives (e.g., antibacterial agents, antifungal agents), isotonic agents, absorption delaying agents, stabilizers, gels, binders, excipients, disintegration agents, lubricants, sweetening agents, flavoring agents, dyes, such like materials and combinations thereof, as would be known to one of ordinary skill in the art. In some examples, the health food products described herein may further include neuroprotective foods, such as fish oil, flax seed oil, and/or benzoate.

In some examples, the health food product is a nutraceutical composition, which refers to compositions containing components from food sources and conferring extra health benefits in addition to the basic nutritional value found in foods. A nutraceutical composition as described herein comprises any of the salts of formula [A][B], as described herein and additional ingredients and supplements that promote good health and/or enhance stability and bioactivity of the salt of formula [A][B].

The actions of nutraceutical compositions may be fast or/and short-term or may help achieve long-term health objectives as those described herein, e.g., improving basic behavioral functioning, hyperactivity, anxiety, depression, sensorimotor gating, pain threshold, memory and/or cognitive functioning in, e.g., human subjects who have or are at risk for a neuropsychiatric disorder. The nutraceutical compositions may be contained in an edible material, for example, as a dietary supplement or a pharmaceutical formulation. As a dietary supplement, additional nutrients, such as vitamins, minerals or amino acids may be included. The composition can also be a drink or a food product, e.g., tea, soft drink, juice, milk, coffee, cookie, cereal, chocolate, and snack bar. If desired, the composition can be sweetened by adding a sweetener such as sorbitol, maltitol, hydrogenated glucose syrup and hydrogenated starch hydrolyzate, high fructose corn syrup, cane sugar, beet sugar, pectin, or sucralose.

The nutraceutical composition disclosed herein can be in the form of a solution. For example, the nutraceutical formulation can be provided in a medium, such as a buffer, a solvent, a diluent, an inert carrier, an oil, or a creme. In some examples, the formulation is present in an aqueous solution that optionally contains a non-aqueous co-solvent, such as an alcohol. The nutraceutical composition can also be in the form of powder, paste, jelly, capsule, or tablet. Lactose and corn starch are commonly used as diluents for capsules and as carriers for tablets. Lubricating agents, such as magnesium stearate, are typically added to form tablets.

The health food products may be formulated for a suitable administration route, for example, oral administration. For oral administration, the composition can take the form of, for example, tablets or capsules, prepared by conventional means with acceptable excipients such as binding agents (for example, pregelatinised maize starch, polyvinylpyrrolidone or hydroxypropyl methylcellulose); fillers (for example, lactose, microcrystalline cellulose or calcium hydrogen phosphate); lubricants (for example, magnesium stearate, talc or silica); disintegrants (for example, potato starch or sodium starch glycolate); or wetting agents (for example, sodium lauryl sulphate). The tablets can be coated by methods well known in the art. Also included are bars and other chewable formulations.

In some examples, the health food product can be in a liquid form and the one or more edible carriers can be a solvent or dispersion medium comprising but not limited to, ethanol, polyol (e.g., glycerol, propylene glycol, liquid polyethylene glycol), lipids (e.g., triglycerides, vegetable oils, liposomes) or combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof. In many cases, it will be advisable to include an isotonic agent, such as, for example, sugars, sodium chloride or combinations thereof.

Liquid preparations for oral administration can take the form of, for example, solutions, syrups or suspensions, or they can be presented as a dry product for constitution with water or other suitable vehicle before use. In one embodiment, the liquid preparations can be formulated for administration with fruit juice. Such liquid preparations can be prepared by conventional means with pharmaceutically acceptable additives such as suspending agents (for example, sorbitol syrup, cellulose derivatives or hydrogenated edible fats); emulsifying agents (for example, lecithin or acacia); non-aqueous vehicles (for example, almond oil, oily esters, ethyl alcohol or fractionated vegetable oils); and preservatives (for example, methyl or propyl-p-hydroxybenzoates, benzoate or sorbate).

In certain embodiments, the composition is a medical food. A medical food product is a food product formulated to be consumed or administered enterally. Such a food product is usually used under the supervision of a physician for the specific dietary management of a target disease, such as those described herein. In some instances, such a medical food composition is specially formulated and processed (as opposed to a naturally occurring foodstuff used in a natural state) for a patient in need of the treatment (e.g., human patients who suffer from illness or who requires use of the product as a major active agent for alleviating a disease or condition via specific dietary management). In some examples, a medical food composition described herein is not one of those that would be simply recommended by a physician as part of an overall diet to manage the symptoms or reduce the risk of a disease or condition.

Any of the medical food compositions described herein, comprising the salt of formula [A][B] described herein and at least one carrier (e.g., those described herein), can be in the form of a liquid solution; powder, bar, wafer, a suspension in an appropriate liquid or in a suitable emulsion, as detailed below. The at least one carrier, which can be either naturally-occurring or synthetic (non-naturally occurring), would confer one or more benefits to the salt of formula [A][B] in the composition, for example, stability, bioavailability, and/or bioactivity. Any of the carriers described herein may be used for making the medical food composition. In some embodiments, the medical food composition may further comprise one or more additional ingredients selected from the group including, but not limited to natural flavors, artificial flavors, major trace and ultra-trace minerals, minerals, vitamins, oats, nuts, spices, milk, egg, salt, flour, lecithin, xanthan gum and/or sweetening agents. The medical food composition may be placed in a suitable container, which may further comprise at least an additional therapeutic agent such as those described herein.

In some embodiments, the composition is a pharmaceutical composition comprising the salt of formula [A][B] described herein and at least one pharmaceutically acceptable excipient and/or carrier.

In certain embodiments, the salt of formula [A][B] described herein is provided in an effective amount in the pharmaceutical composition. In certain embodiments, the effective amount is a therapeutically effective amount (e.g., amount effective for treating and/or reducing the risk for a neuropsychiatric disorder and/or bacterial infectious disease (e.g., tuberculosis) in a subject in need thereof).

Pharmaceutical compositions described herein can be prepared by any method known in the art of pharmacology. In general, such preparatory methods include bringing the salt of formula [A][B] described herein (i.e., the "active ingredient") into association with a carrier or excipient, and/or one or more other accessory ingredients, and then, if necessary and/or desirable, shaping, and/or packaging the product into a desired single- or multi-dose unit.

Pharmaceutical compositions can be prepared, packaged, and/or sold in bulk, as a single unit dose, and/or as a plurality of single unit doses. A "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage, such as one-half or one-third of such a dosage.

Relative amounts of the active ingredient, the pharmaceutically acceptable excipient, and/or any additional ingredients in a pharmaceutical composition described herein will vary, depending upon the identity, size, and/or condition of the subject treated and further depending upon the route by which the composition is to be administered. The composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents and/or pH adjusters, lubricating agents, carriers, enhancers, sustained released reagents, and/or anti-sedimentation agents and/or oils. Excipients such as cocoa butter and suppository waxes, coloring agents, coating agents, sweetening, flavoring, and perfuming agents may also be present in the composition.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates described herein are mixed with solubilizing agents such as Cremophor®, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension, or emulsion in a nontoxic parenterally acceptable diluent or solvent, for example, as a solution in 1,3-butanediol. Among the acceptable vehicles and solvents that can be employed are water, Ringer's solution, U.S.P., and isotonic sodium chloride solution. In addition, sterile, fixed oils are conventionally employed as a solvent or suspending medium. For this purpose, any bland fixed oil can be employed including synthetic mono- or di-glycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form may be accomplished by dissolving or suspending the drug in an oil vehicle.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may include a buffering agent. In the case of capsules, the active ingredient can be encapsulated into capsule shells without any excipient or carrier.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings, release controlling coatings, and other coatings well known in the art of pharmacology. They may optionally comprise opacifying agents and can be of a composition that they release the active ingredient(s) only, or preferentially, in a certain part of the digestive tract, optionally, in a delayed manner. Examples of encapsulating compositions which can be used include polymeric substances and waxes. Solid compositions of a similar type can be employed as fillers in soft and hard-filled gelatin capsules using such excipients as lactose or milk sugar as well as high molecular weight polyethylene glycols and the like.

The active ingredient can be in a micro-encapsulated form with one or more excipients as noted above. The solid dosage forms of tablets, dragees, capsules, pills, and granules can be prepared with coatings and shells such as enteric coatings, release controlling coatings, and other coatings well known in the pharmaceutical formulating art. In such solid dosage forms the active ingredient can be admixed with at least one inert diluent such as sucrose, lactose, or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the digestive tract, optionally, in a delayed manner. Examples of encapsulating agents which can be used include, but not limited to, polymeric substances and waxes.

All commercially available enteric materials can be applied to the composition of the invention. In some embodiments of the composition, the enteric material is selected from polymethacrylate-based coating material, phthalate-based coating material, cellulose ester-based coating material, shellac, sodium alginate or a mixture thereof.

In some embodiments of the composition, the polymethacrylate-based coating material is selected from poly(methacrylic acid-co-ethyl acrylate) in a ratio of 1:1 (i.e. Eudragit L 100-55, Eudragit L 30 D-55, Eastacryl 30 D series, Kollicoat MAE 30 DP, Kollicoat MAE 100 P, Acryl-EZE 93 series and Acryl-EZE MP series), poly(methacylic acid-co-methyl methacrylate) in a ratio of 1:1 (i.e. Eudragit L 100, Eudragit L 12,5, Eudragit L 12,5 P, and Opadry 94 series), poly(methacylic acid-co-methyl methacrylate) in a ratio of 1:2 (i.e. Eudragit S 100, Eudragit S 12,5, Eudragit S 12,5 P, and Opadry 95 series), and poly(methyl acrylate-co-methyl methacrylate-co-methacrylic acid in a ratio of 7:3:1 (i.e. Eudragit FS 30 D).

In some embodiments of the composition, the phthalate-based coating material is selected from polyvinyl acetate phthalate (i.e. Opadry 91 series, and Sureteric series), hydroxypropyl methylcellulose phthalate (i.e. HPmcp-HP Grades series), diethyl phthalate, and cellulose acetate phthalate (i.e. Eastman™ C-A-P).

In some embodiments of the composition, the cellulose ester-based coating material are selected from cellulose acetate trimellitate, cellulose acetate succinate, and hydroxypropyl methylcellulose acetate succinate (i.e. AQOAT AS series, and ENTERACT™ HPMCAS).

In some embodiments of the composition, the enteric materials comprise 90.5%-98.49% of poly(methacrylic acid-co-ethyl acrylate) in a ratio of 1:1, 0.5%-2% of sodium lauryl sulfate, 0.01%-2.5% of triethyl citrate, 0.5%-2.5% of colloidal silicon dioxide, and 0.5%-2.5% of talc.

In some embodiments of the composition, the composition further comprises 10 to 50 mg of an isolation layer material selected from hydroxypropyl methylcellulose-based coating materials. Specifically, the average molecular weight of the hydroxypropyl methylcellulose is 50000 to 125000 and the solid content is 8%. Other commercially available isolation layer materials can be applied to the composition of the invention.

In certain embodiments, the one or more isolation materials are provided in 10 to 50 mg, 15 to 45 mg, 20 to 35 mg, or 25 to 30 mg.

In some embodiments of the composition, the isolation layer materials comprise 95.5%-99.49% hydroxypropyl methylcellulose, 0.5%-2.5% talc, and 0.01%-2% of triacetin.

In some embodiments of the composition, the composition further comprises one or more pharmaceutically acceptable excipients selected from fillers, binders, disintegrating agents, and/or lubricants.

In some embodiments of the composition, the fillers are selected from starches, lactose, sucrose, glucose, mannitol, calcium phosphate dibasic anhydrous, microcrystalline cellulose, and mixtures thereof. In some embodiments of the composition, microcrystalline cellulose is microcrystalline cellulose having a moisture content of, for example, 3-10%, or 3-5% (e.g. microcrystalline cellulose pH 102).

In some embodiments of the composition, the binders are selected from carboxymethylcellulose, hydroxypropyl cellulose, alginates, gelatin, polyvinylpyrrolidinone, acacia, and mixtures thereof.

In some embodiments of the composition, the disintegrating agents are selected from agar, calcium carbonate, potato or tapioca starch, alginic acid, certain silicates, sodium starch glycolate (SSG), croscarmellose, crospovidone, sodium carbonate, and mixtures thereof.

In some embodiments of the composition, the lubricants are selected from magnesium stearate, colloidal silicon dioxide, talc, calcium stearate, solid polyethylene glycols, sodium lauryl sulfate, and mixtures thereof.

In some embodiments of the composition, the pharmaceutically acceptable excipients comprise 50-500 mg of fillers, 10-100 mg of binders, 10-200 mg of disintegrating agents, 5-100 mg of lubricants. In some embodiments of the composition, the amount of the fillers is 50-500 mg, 200-450 mg, 250-400 mg, 300-380 mg, or 330-350 mg. In some embodiments of the composition, the amount of the binders is 10-100 mg, 20-90 mg, 25-80 mg, 30-70 mg, 35-60 mg, or 40-50 mg. In some embodiments of the composition, the amount of the disintegrating agents is 10-200 mg, 15-180 mg, 20-160 mg, 25-140 mg, 30-120 mg, 40-100 mg, or 60-80 mg. In some embodiments of the composition, the amount of the lubricants is 5-100 mg, 7.5-90 mg, 10-80 mg, 20-70 mg, 30-60 mg, or 40-50 mg.

In some embodiments of the composition, the pharmaceutical acceptable excipients are microcrystalline cellulose pH 102, hydroxypropyl cellulose, croscarmellose sodium and magnesium stearate.

In some embodiments, the pharmaceutical composition for topical administration disclosed herein is spread on an impermeable support to obtain a patch. Particularly, the impermeable support is a support for a matrix system (e.g., matrix-dispersion system and drug in-adhesive), a reservoir patch system or a microreservoir system.

In some embodiments, the at least one pharmaceutically acceptable excipient and/or carrier contained in the pharmaceutical composition for oral administration is a capsule. All commercially available capsules can be applied to the pharmaceutical composition of the invention, including hard and soft gelatin capsules, HPMC capsules, and the like. The ingredients of commercially available capsules are also comprised in the capsule formulation of the invention, including, but not limited to, hydroxypropyl methylcellulose (HPMC), gelatin, methyl paraben (i.e., methyl-4-hydroxybenzoate), propyl paraben (i.e., propyl-4-hydroxybenzoate), sodium lauryl sulphate, Brilliant Blue FCF, new coccin, titanium dioxide, Sunset Yellow FCF, tartrazine, water, or combination thereof.

In some embodiments, the capsule formulation of the present invention further comprises an enteric coating on the surface of the capsule. All commercially available enteric coating can be applied on the surface of the capsule for the capsule formulation of the present invention. Preferably, the enteric coating is composed of a material selected from copolymers of methacrylic acid and ethyl acrylate; more preferably, the copolymer of methacrylic acid and ethyl acrylate is Kollicoat® MAE 30 DP (BASF), in which the ratio of methacrylic acid and ethyl acrylate is 1:1 and the solid content is 30%.

For the coating purpose, the material of the enteric coating is resolved in an organic solvent. Preferably, the organic solvent is propylene glycol.

Although the descriptions of pharmaceutical compositions provided herein are mainly directed to pharmaceutical compositions which are suitable for administration to humans, such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

The composition described herein is typically formulated in dosage unit form for ease of administration and uniformity of dosage. It will be understood, however, that the total daily usage of the compositions described herein will be decided by a physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex, and diet of the subject; the time of administration, route of administration, and rate of excretion of the specific active ingredient employed; the duration of the treatment; drugs used in combination or coincidental with the specific active ingredient employed; and like factors well known in the medical arts.

Also encompassed by the disclosure are kits (e.g., pharmaceutical packs). The kits provided may comprise a pharmaceutical composition described herein and a container (e.g., a vial, ampule, bottle, syringe, and/or dispenser package, or other suitable container).

In certain embodiments, a kit described herein includes a container comprising a composition described herein. In certain embodiments, a kit described herein is useful in treating and/or reducing the risk for a neuropsychiatric disorder and/or a bacterial infectious disease (e.g., tuberculosis) in a subject in need thereof.

In certain embodiments, a kit described herein further includes instructions for using the composition described herein included in the kit. A kit described herein may also include information as required by a regulatory agency such as the U.S. Food and Drug Administration (FDA). In certain embodiments, the information included in the kits is prescribing information. In certain embodiments, the kits and instructions provide for treating and/or reducing the risk for a neuropsychiatric disorder and/or a bacterial infectious disease (e.g., tuberculosis). A kit described herein may include one or more additional pharmaceutical agents described herein as a separate composition.

Method of Treatment

Another aspect of the present invention is to provide a method comprising administering said subject an effective amount of the salt of formula [A][B] described herein, or a composition thereof, described herein.

In some embodiments, the neuropsychiatric disorder is selected from the group consisting of schizophrenia, psychotic disorders, Alzheimer's disease, frontotemporal dementia, vascular dementia, dementia with Lewy bodies, senile dementia, mild cognitive impairment, benign forgetfulness, closed head injury, autistic spectrum disorder, Asperger's disorder, fragile X syndrome, attention deficit hyperactivity disorders, attention deficit disorder, obsessive compulsive disorder, tic disorders, childhood learning disorders, premenstrual syndrome, depression, major depressive disorder, anhedonia, suicidal ideation and/or behaviors, bipolar disorder, anxiety disorders, panic disorder, post-traumatic stress disorder, chronic mild and unpredictable stress, eating disorders, addiction disorders, personality disorders, Parkinson's disorder, Huntington's disorder, multiple sclerosis, amyotrophic lateral sclerosis, Tourette's syndrome, nocturnal enuresis, non-epileptic seizures, blepharospasm, Duchenne muscular dystrophy, stroke, chronic pain, neuropathic pain including hyperalgesia and allodynia, diabetic polyneuropathy, and chronic pain syndromes.

The salt of formula [A][B] disclosed herein or any one of the compositions thereof described herein are useful in treating and/or preventing a neuropsychiatric disorder. In certain embodiments, the neuropsychiatric disorder is schizophrenia. In certain embodiments, the neuropsychiatric disorder is a psychotic disorder. In certain embodiments, the neuropsychiatric disorder is Alzheimer's disease. In certain embodiments, the neuropsychiatric disorder is frontotemporal dementia. In certain embodiments, the neuropsychiatric disorder is vascular dementia. In certain embodiments, the neuropsychiatric disorder is dementia with Lewy bodies. In certain embodiments, the neuropsychiatric disorder is senile dementia. In certain embodiments, the neuropsychiatric disorder is mild cognitive impairment. In certain embodiments, the neuropsychiatric disorder is benign forgetfulness. In certain embodiments, the neuropsychiatric disorder is closed head injury. In certain embodiments, the neuropsychiatric disorder is autistic spectrum disorder including Asperger's disorder. In certain embodiments, the neuropsychiatric disorder is fragile X syndrome. In certain embodiments, the neuropsychiatric disorder is an attention deficit hyperactivity disorder. In certain embodiments, the neuropsychiatric disorder is attention deficit disorder. In certain embodiments, the neuropsychiatric disorder is an obsessive compulsive disorder. In certain embodiments, the neuropsychiatric disorder is a tic disorder. In certain embodiments, the neuropsychiatric disorder is a childhood learning disorder. In certain embodiments, the neuropsychiatric disorder is premenstrual syndrome. In certain embodiments, the neuropsychiatric disorder is depression, including dysthymia and bereavement. In certain embodiments, the neuropsychiatric disorder is major depressive disorder. In certain embodiments, the neuropsychiatric disorder is anhedonia. In certain embodiments, the neuropsychiatric disorder is suicidal ideation and/or behavior. In certain embodiments, the neuropsychiatric disorder is bipolar disorder including bipolar I and II disorders. In certain embodiments, the neuropsychiatric disorder is an anxiety disorder including panic and phobic disorders. In certain embodiments, the neuropsychiatric disorder is panic disorder. In certain embodiments, the neuropsychiatric disorder is post-traumatic stress disorder. In certain embodiments, the neuropsychiatric disorder is chronic mild and unpredictable stress. In certain embodiments, the neuropsychiatric disorder is an eating disorder including bulimia and anorexia. In certain embodiments, the neuropsychiatric disorder is an addiction disorder including substance dependence or abuse. In certain embodiments, the neuropsychiatric disorder is a personality disorder. In certain embodiments, the neuropsychiatric disorder is Parkinson's disorder. In certain embodiments, the neuropsychiatric disorder is Huntington's disorder. In certain embodiments, the neuropsychiatric disorder is multiple sclerosis. In certain embodiments, the neuropsychiatric disorder is amyotrophic lateral sclerosis. In certain embodiments, the neuropsychiatric disorder is Tourette's syndrome. In certain embodiments, the neuropsychiatric disorder is nocturnal enuresis. In certain embodiments, the neuropsychiatric disorder is non-epileptic seizures. In certain embodiments, the neuropsychiatric disorder is blepharospasm. In certain embodiments, the neuropsychiatric disorder is Duchenne muscular dystrophy. In certain embodiments, the neuropsychiatric disorder is stroke. In certain embodiments, the neuropsychiatric disorder is chronic pain. In certain embodiments, the neuropsychiatric disorder is neuropathic pain, including hyperalgesia and allodynia. In certain embodiments, the neuropsychiatric disorder is diabetic polyneuropathy. In certain embodiments, the neuropsychiatric disorder is chronic pain syndromes.

In certain embodiments, the method described herein further includes administering to the subject an additional pharmaceutical agent. In certain embodiments, the method described herein further includes contacting the biological sample with an additional pharmaceutical agent. In certain embodiments, the method described herein further includes contacting the tissue with an additional pharmaceutical agent. In certain embodiments, the method described herein further includes contacting the cell with an additional pharmaceutical agent. In certain embodiments, the composition described herein is a composition for co-use with one or more additional pharmaceutical agents for treating the neuropsychiatric disorder. In certain embodiments, the composition described herein and the one or more additional pharmaceutical agents are administered to the subject concurrently or sequentially.

The salt of formula [A][B] disclosed herein or any one of the compositions thereof provided herein can be administered by any route, including enteral (e.g., oral), parenteral, intravenous, intramuscular, intra-arterial, intramedullary, intrathecal, subcutaneous, intraventricular, transdermal, interdermal, subcutaneous, intradermal, rectal, intravaginal, intraperitoneal, topical (as by powders, ointments, creams, and/or drops). Specifically, contemplated routes are oral administration, intravenous administration (e.g., systemic intravenous injection), regional administration via blood and/or lymph supply, and/or direct administration to an affected site. In general, the most appropriate route of administration will depend upon a variety of factors including the nature of the agent (e.g., its stability in the environment of the gastrointestinal tract), and/or the condition of the subject (e.g., whether the subject is able to tolerate oral administration).

The exact amount of the salt of formula [A][B] described herein required to achieve an effective amount will vary from subject to subject, depending, for example, on species, age, and general condition of a subject, severity of the side effects or disorder, identity of the particular the salt of formula [A][B] described herein, mode of administration, and the like. An effective amount may be included in a single dose (e.g., single oral dose) or multiple doses (e.g., multiple oral doses). In certain embodiments, when multiple doses are administered to a subject or applied to a biological sample, tissue, or cell, any two doses of the multiple doses include different or substantially the same amounts of the salt of formula [A][B] described herein. In certain embodiments, when multiple doses are administered to a subject or applied to a biological sample, tissue, or cell, the frequency of administering the multiple doses to the subject or applying the multiple doses to the tissue or cell is three doses a day, two doses a day, one dose a day, one dose every other day, one dose every third day, one dose every week, one dose every other week, one dose monthly or one dose every other month. In certain embodiments, the frequency of administering the multiple doses to the subject or applying the multiple doses to the tissue or cell is one dose per day. In certain embodiments, the frequency of administering the multiple doses to the subject or applying the multiple doses to the tissue or cell is two doses per day. In certain embodiments, when multiple doses are administered to a subject or applied to a biological sample, tissue, or cell, the duration between the first dose and last dose of the multiple doses is one day, two days, four days, one week, two weeks, three weeks, one month, two months, three months, four months, six months, nine months, one year, two years, three years, four years, five years, seven years, ten years, fifteen years, twenty years, or the lifetime of the subject, biological sample, tissue, or cell. In certain embodiments, the duration between the first dose and last dose of the multiple doses is three months, six months, or one year. In certain embodiments, the duration between the first dose and last dose of the multiple doses is the lifetime of the subject, biological sample, tissue, or cell. In certain embodiments, a dose (e.g., a single dose, or any dose of multiple doses) described herein includes independently between 1 mg and 3 mg, between 3 mg and 10 mg, between 10 mg and 30 mg, between 30 mg and 100 mg, between 100 mg and 300 mg, between 300 mg and 1,000 mg, or between 1 g and 10 g, inclusive, of the salt of formula [A][B] described herein. In certain embodiments, a dose described herein includes independently between 100 mg and 1500 mg, inclusive, of the salt of c formula [A][B] described herein. In certain embodiments, a dose described herein includes independently between 300 mg and 1000 mg, inclusive, of the salt of formula [A][B] described herein.

Dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

The salt of formula [A][B] disclosed herein or any one of the compositions thereof, as described herein, can be administered in combination with one or more additional pharmaceutical agents (e.g., therapeutically and/or prophylactically active agents) useful in treating and/or reducing the risk for a neuropsychiatric disorder and/or bacterial infectious disease (e.g., tuberculosis). The salt of formula [A][B] disclosed herein or any one of the compositions thereof can be administered in combination with additional pharmaceutical agents that improve their activity (e.g., activity (e.g., potency and/or efficacy) in treating and/or reducing the risk for a neuropsychiatric disorder and/or bacterial infectious disease (e.g., tuberculosis) in a subject in need thereof), improve bioavailability, improve safety, reduce drug resistance, reduce and/or modify metabolism, inhibit excretion, and/or modify distribution in a subject, biological sample, tissue, or cell. It will also be appreciated that the therapy employed may achieve a desired effect for the same disorder, and/or it may achieve different effects. In certain embodiments, a pharmaceutical composition described herein including the salt of formula [A][B] described herein and an additional pharmaceutical agent shows a synergistic effect that is absent in a pharmaceutical composition including the salt of formula [A][B] described herein and the additional pharmaceutical agent, but not both.

The salt of formula [A][B] disclosed herein or any one of the compositions thereof can be administered concurrently with, prior to, or subsequent to one or more additional pharmaceutical agents, which may be useful as, e.g., combination therapies in treating and/or reducing the risk for a neuropsychiatric disorder and/or bacterial infectious disease (e.g., tuberculosis) in a subject. Pharmaceutical agents include therapeutically active agents. Pharmaceutical agents also include prophylactically active agents. Pharmaceutical agents include small organic molecules such as drug compounds (e.g., compounds approved for human or veterinary use by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, antibodies, small molecules linked to proteins such as antibodies, glycoproteins, steroids, nucleic acids, DNAs, RNAs, nucleotides, nucleosides, oligonucleotides, antisense oligonucleotides, lipids, hormones, vitamins, and cells. In certain embodiments, the additional pharmaceutical agent is a pharmaceutical agent useful in treating and/or reducing the risk for a neuropsychiatric disorder and/or bacterial infectious disease (e.g., tuberculosis) in a subject. In certain embodiments, the additional pharmaceutical agent is a pharmaceutical agent approved by a regulatory agency (e.g., the US FDA) for treating and/or reducing the risk for a neuropsychiatric disorder and/or bacterial infectious disease (e.g., tuberculosis) in a subject. Each additional pharmaceutical agent may be administered at a dose and/or on a time schedule determined for that pharmaceutical agent. The additional pharmaceutical agents may also be administered together with each other and/or with the salt of formula [A][B] disclosed herein or any one of the compositions thereof described herein in a single dose or administered separately in different doses. The particular combination to employ in a regimen will take into account compatibility of the salt of formula [A][B] described herein with the additional pharmaceutical agent(s) and/or the desired therapeutic and/or prophylactic effect to be achieved. In general, it is expected that the additional pharmaceutical agent(s) in combination be utilized at levels that do not exceed the levels at which they are utilized individually. In some embodiments, the levels utilized in combination will be lower than those utilized individually.

In certain embodiments, the additional pharmaceutical agent is selected from agents for treating and/or reducing the risk for a neuropsychiatric disorder and/or bacterial infectious disease (e.g., tuberculosis), or combinations thereof. In certain embodiments, the salt of formula [A][B] disclosed herein or any one of the pharmaceutical composition thereof described herein can be administered in combination with a therapy for treating and/or reducing the risk for a neuropsychiatric disorder and/or bacterial infectious disease (e.g., tuberculosis).

In certain embodiments, the additional pharmaceutical agent is an agent for treating and/or reducing the risk for a neuropsychiatric disorder selected from an antipsychotic, an antidepressant, a psychostimulant, a mood stabilizer, an anxiolytic, an agent for treating attention deficit hyperactivity disorder (ADHD) or an agent for treating Alzheimer's disease (AD). In certain embodiments, the additional pharmaceutical agent includes, but not limited to, an antipsychotic, an antidepressant, a mood stabilizer, an anxiolytic, a psychostimulant and an agent treating tuberculosis.

Exemplary antipsychotic drugs include, but are not limited to, butyrophenone (e.g., haloperidol (HALDOL™), phenothiazine (e.g., chlorpromazine (THORAZINE™), fluphenazine (PROLIXIN™), perphenazine (TRILAFON™), prochlorperazine (COMPAZINE™), thioridazine (MELLARIL™), trifluoperazine (STELAZINE™), mesoridazine, promazine, triflupromazine (VESPRIN™), levomepromazine (NOZINAN™), promethazine (PHENERGAN™), thioxanthene (e.g., chlorprothixene, flupenthixol (DEPIXOL™, FLUANXOL™)), thiothixene (NAVANE™), zuclopenthixol (CLOPIXOL™, ACUPHASE™), clozapine (CLOZARIL™), olanzapine (ZYPREXA™), risperidone (RISPERDAL™, RISPERDAL CONSTA™), quetiapine (SEROQUEL™), ziprasidone (GEODON™), amisulpride (SOLIAN™), asenapine, paliperidone (INVEGA®), aripiprazole (ABILIFY™), dopamine partial agonists (BIFEPRUNOX™, NORCLOZAPINE™ (ACP-104)), lamotrigine (LAMICTAL™), cannabidiol, LY2140023, droperidol, pimozide, butaperazine, carphenazine, remoxipride, piperacetazine, sulpiride, acamprosate, tetrabenazine (NITOMAN™, XENAZINE™) and the like.

Alternatively, the second therapeutic agent can be an antidepressant and/or mood stabilizer. In certain embodiments the antidepressant comprises a monoamine oxidase inhibitor (MAOI), a tricyclic antidepressant (TCA), a tetracyclic antidepressant (TeCA), a selective serotonin reuptake inhibitor (SSRI), a noradrenergic and specific serotonergic antidepressant (NASSA), a norepinephrine (noradrenaline) reuptake inhibitor, a norepinephrine-dopamine reuptake inhibitor, a serotonin-norepinephrine-dopamine reuptake inhibitor (SNDRI), a serotonin-norepinephrine reuptake inhibitor (SNRI), mood stabilizer, and/or monoamine oxidase inhibitor (MAOI). Exemplary SSRIs include fluoxetine (PROZAC™), paroxetine (PAXIL™, SEROXAT™), escitalopram (LEXAPRO™, ESIPRAM™), citalopram (CELEXA™), sertraline (ZOLOFT™), fluvoxamine (LUVOX™)). Exemplary SNRIs include venlafaxine (EFFEXOR™), milnacipram and duloxetine (CYM-BALTA™). Additional antidepressant include a noradrenergic and specific serotonergic antidepressant (NASSA) (e.g., mirtazapine (AVANZA™, ZISPIN™, REMERON™), or mianserin, a norepinephrine (noradrenaline) reuptake inhibitor (NRI) (e.g., reboxetine (EDRONAX™)), a norepinephrine-dopamine reuptake inhibitors (e.g., bupropion (WELLBUTRIN™, ZYBAN™)), amitriptyline, nortriptiline, protriptyline, desipramine, imipramine, trimipramine, amoxapine, bupropion, bupropion SR, clomipramine, doxepin, isocarboxazid, venlafaxine XR, tranylcypromine, trazodone, nefazodone, phenelzine, lamatrogine, lithium, topiramate, gabapentin, carbamazepine, oxacarbazepine, valporate, maprotiline, mirtazapine, brofaromine, gepirone, moclobemide, isoniazid, iproniazid, and the like.

In some embodiments, the anxiolytic includes Atarax, Benadryl, azaspirones, benzodiazepines, such as lorazepam, prazepam, flurazepam, klonazepam, chlordiazepoxide, halazepam, temazepam, oxazepam, chlorazepate, diazepam, alprazolam, beta blockers, such as propranolol, atenolol and others as will be appreciated by the skilled artisan.

In some embodiments, the second therapeutic agent can be an agent for the treatment of ADD and/or ADHD. Suitable ADHD medications include, but are not limited to amphetamine, modafinil, desoxyn, methamphetamine, cocaine, arecoline, dexmethylphenidate (focalin, focalin XR), dextroamphetamine (dexedrine, dexedrine spansules, dextroamphetamine ER, dextrostat), methylphenidate (concerta, daytrana, metadate CD, metadate ER, methylin, methylin ER, ritalin, ritalin-LA, ritalin-SR), lisdexamfetamine dimesylate (Vyvanse), mixed salts amphetamine (Adderall, Adderall XR), atomoxetine (Strattera), clonidine hydrochloride (Catapres), guanfacine hydrochloride (Tenex), arecoline, and pemoline.

Further, in some embodiments, the second therapeutic agent may be an agent for use in treating a cognitive disorder, and/or a condition characterized by neurodegeneration (e.g., Alzheimer's disease, or Parkinson's disease). Such therapeutic agents include, but are not limited to tacrine, rivastigmine, donepezil (Aricept™), physostigmine, nicotine, arecoline, huperzine alpha, selegiline, rilutek™ (riluzole), memantine (AXURA™, AKATINOL™, NAMENDA™, EBIXA™, ABIXA™), vitamine c, vitamine e, carotenoids, ginkgo biloba, and the like.

In certain embodiments, the additional pharmaceutical agent is an agent for treating and/or reducing the risk for tuberculosis selected from isoniazid, rifampin, ethambutol, pyrazinamide, rifabutin, rifapentine, capreomycin, kanamycin, amikacin, streptomycin, fluoroquinolone antibiotics (e.g. levofloxacin, moxifloxacin, ofloxcin, gatifloxacin), prothionamide, para-aminosalicylic acid, ethionamide, terizadone, clofazimine, clarithromycin, linezolid, amoxicillin-clavulanate, thiacetazone, bedaquiline, delamanid, carbapenmem antibiotics (e.g. imipenem, meropenem and doripenem).

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

Example 1: Preparation of D-cycloserine Succinate Salt (4:1) Form

D-cycloserine (250 mg) and succinic acid (145 mg) was added in 2 mL deionized water and stirred at 800 rpm under room temperature. The solution was added dropwise into 50 mL isopropanol and stirred at 800 rpm under room temperature for 10 minutes. The mixture was filtered and dried in vacuum to obtain the D-cycloserine succinate (4:1) salt form (yield=315.4 mg, 79.8%). The salt thus obtained was analyzed by $^1$H nuclear magnetic resonance ($^1$H-NMR), X-ray powder diffraction (XRPD) and thermoanalyses (including TGA and DSC analyses) as described herein.

$^1$H-NMR: $^1$H-NMR analysis was performed on Bruker Fourier 400 (Bruker) in a deuterated solvent such as dimethyl sulfoxide or deuterium oxide at 25° C.

XRPD: X-ray powder diffraction patterns were obtained on D8 ADVANCE (Bruker AXS Gmbh, Germany). Samples were scanned in continuous mode from 4-45° (2θ) with step size of 0.02° on a spinning stage at 40 kV and 40 mA with Cu Kα radiation. The incident beam path was equipped with a 0.2 mm divergence slit and 0.02 mm air scattering screen. The diffracted beam was equipped with Ni-filter. Detection was accomplished with a Lynxeye detector (Bruker AXS).

Thermogravimetric analysis (TGA): TGA data were measured by TGA Q50 (TA Instruments) with platinum crucibles at a heating rate of 10° C./min between 35° C.-400° C.

Differential Scanning Calorimetry (DSC): The melting point of the salt form was determined using the differential scanning calorimeter (DSC) method. The DSC data were measured and collected by DSC 25 (TA Instruments) with T-zero aluminum low-mass pan at the heating rate of 10° C./min between 40° C.-300° C.

The $^1$H-NMR, XRPD and thermoanalyses results of D-cycloserine, succinic acid, and the salt obtained by the method described in Example 1 are shown in FIGS. 1 to 12.

Example 2: Preparation of D-cycloserine L-tartrate (1:1) Salt Form

D-cycloserine (1000 mg) and L-tartaric acid (1470 mg) were added in 10 mL and 2 mL deionized water respectively, and stirred at 800 rpm under room temperature respectively. When they were dissolved, the L-tartaric acid solution was added into D-cycloserine solution. The resulting solution was added dropwise into 200 mL isopropanol and stirred at 800 rpm under room temperature for 10 minutes. The mixture was filtered and dried in vacuum to obtain the D-cycloserine L-tartrate (1:1) salt form (yield=2047.9 mg, 82.91%).

The $^1$H-NMR, XRPD and thermoanalyses results of L-tartaric acid and the salt obtained by the method described in Example 2 above are shown in FIGS. 13 to 20.

Example 3: Preparation of D-cycloserine Maleate (1:1) Salt Form

D-cycloserine (1000 mg) and maleic acid (1136.8 mg) were added in 8 mL deionized water and stirred at 800 rpm under room temperature. The solution was added dropwise into 200 mL of 70% ether in ethanol and stirred at 800 rpm under room temperature for 10 minutes. The mixture was filtered and dried in vacuum to obtain the D-cycloserine maleate (1:1) salt form (yield=1563.7 mg, 73.18%).

The $^1$H-NMR, XRPD and thermoanalyses results of maleic acid and the salt obtained by the method described in Example 3 above are shown in FIGS. 21 to 28.

Example 4: Preparation of D-cycloserine D-tartrate (2:1) Salt Form

D-cycloserine (1000 mg) and D-tartaric acid (1470 mg) were added in 10 mL and 3 mL deionized water separately and stirred at 800 rpm under room temperature respectively. When they were dissolved, the D-tartaric acid solution was added into D-cycloserine solution and stirred for 10 minutes. The resulting solution was added dropwise into 200 mL isopropanol and stirred at 800 rpm under room temperature for 10 minutes. The mixture was filtered and dried in vacuum to obtain the D-cycloserine D-tartrate (2:1) salt form (yield=2047.9 mg, 82.91%).

The $^1$H-NMR, XRPD and thermoanalyses results of D-tartaric acid and the salt obtained by the method described in Example 4 above are shown in FIGS. 29 to 36.

Example 5: D-cycloserine and D-cycloserine Salt at 40° C./75% Relative Humidity (RH) in Closed System for Stress Study 200 mg of D-cycloserine from Strides Shasun Ltd. and Macleods Pharmaceuticals Ltd., L-tartaric acid, maleic acid, D-tartaric acid, D-cycloserine L-tartrate (1:1) salt form and D-cycloserine maleate (1:1) salt form and D-cycloserine D-tartrate (2:1) salt form were independently put into a colorless glass bottle and kept at 40 ° C./75% RH within a close system (i.e. with the cap of the bottle closed) for a stress study respectively.

At the very beginning, appearance results indicated that D-cycloserine from Macleods Pharmaceuticals Ltd., L-tartaric acid, maleic acid, D-tartaric acid, D-cycloserine L-tartrate (1:1) salt form, and D-cycloserine maleate (1:1) salt form and D-cycloserine D-tartrate (2:1) salt form still remained as fine white powder, however, D-cycloserine from Strides Shasun Ltd. remained was pale yellow power. But After one month stress study, both D-cycloserine from Strides Shasun Ltd. and Macleods Pharmaceuticals Ltd. were disintegrated and turned into dark yellow.

Figure 37:
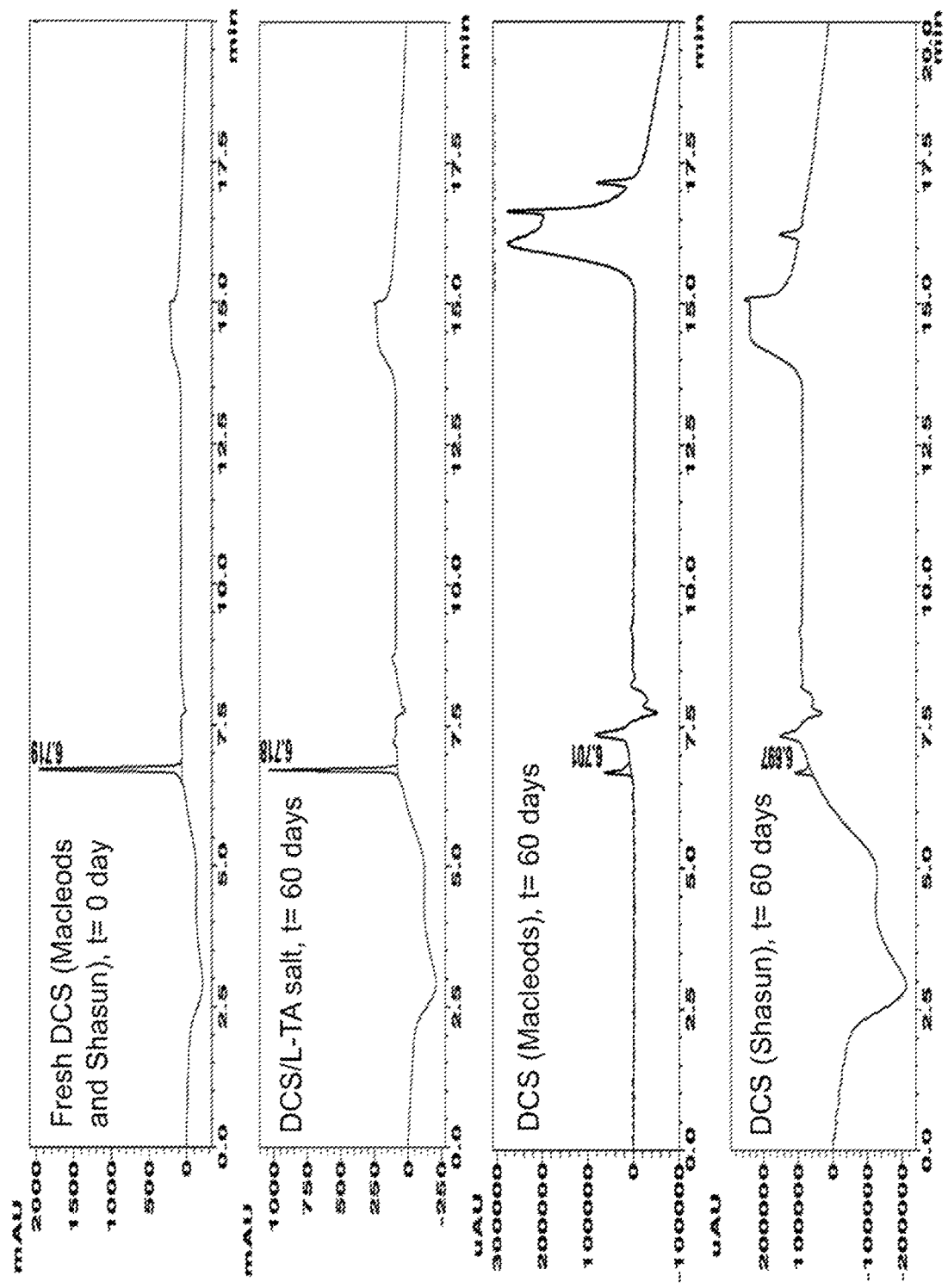
FIG. 37 shows the HPLC analysis of (1) fresh D-cycloserine from Macleods Pharmaceuticals Ltd. and Strides Shasun Ltd. (t=0 day), (2) D-cycloserine L-tartrate (1:1) salt form , (3) D-cycloserine from Macleods Pharmaceuticals Ltd. and (4) D-cycloserine from Strides Shasun Ltd., kept at 40/75% RH for 60 days, as described in Example 5. The results indicate D-cycloserine L-tartrate (1:1) salt was stable while the rest are not.

After 60-day stress study, D-cycloserine from Strides Shasun Ltd. and Macleods Pharmaceuticals Ltd., L-tartaric acid and D-cycloserine L-tartrate (1:1) salt form, and fresh D-cycloserine from Macleods Pharmaceuticals Ltd. and Strides Shasun Ltd. (t=0 day) were analyzed by high performance liquid chromatography (HPLC), as shown in FIG. 37. Only D-cycloserine L-tartrate (1:1) salt form is stable after the 60-day stress study.

Figure 38:
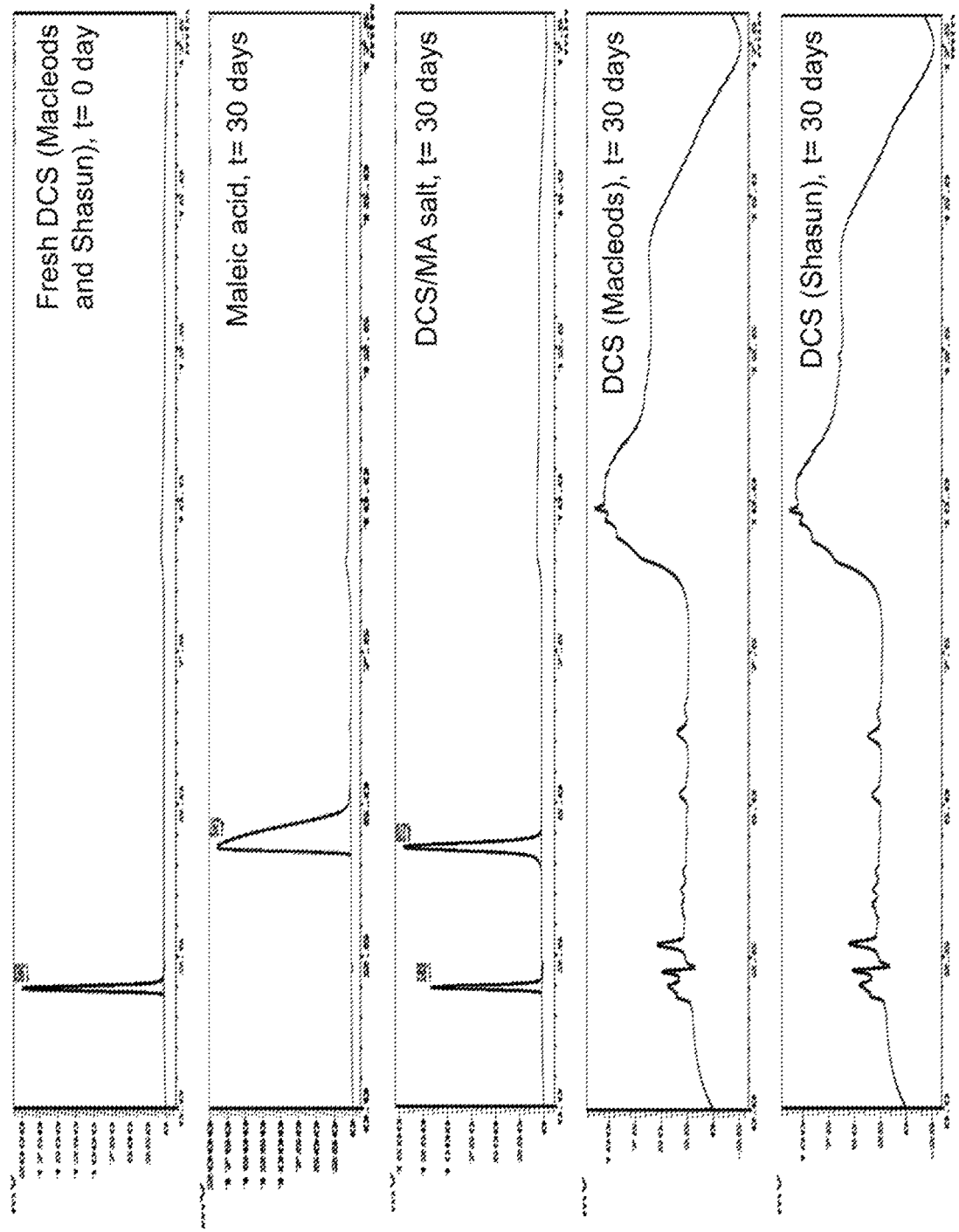
FIG. 38 shows the result of HPLC analysis of (1) fresh D-cycloserine from Macleods Pharmaceuticals Ltd. and Strides Shasun Ltd. (t=0 day), and (2) maleic acid, (3) D-cycloserine maleate (1:1) salt form, (4) D-cycloserine from Macleods Pharmaceuticals Ltd. (5) D-cycloserine from Strides Shasun Ltd. kept at 40/75% RH for 30 days, as described in Example 5. After 30 days, D-cycloserine maleate (1:1) salt was stable, while the rest are not.

In addition, after 30-day stress study, D-cycloserine from Strides Shasun Ltd. and Macleods Pharmaceuticals Ltd., maleic acid, D-cycloserine maleate (1:1) salt form, and fresh D-cycloserine from Macleods Pharmaceuticals Ltd. and Strides Shasun Ltd. (t=0 day) were also analyzed by HPLC, as shown in FIG. 38. Only D-cycloserine maleate (1:1) salt form is stable after the 30-day stress study.

Figure 39:
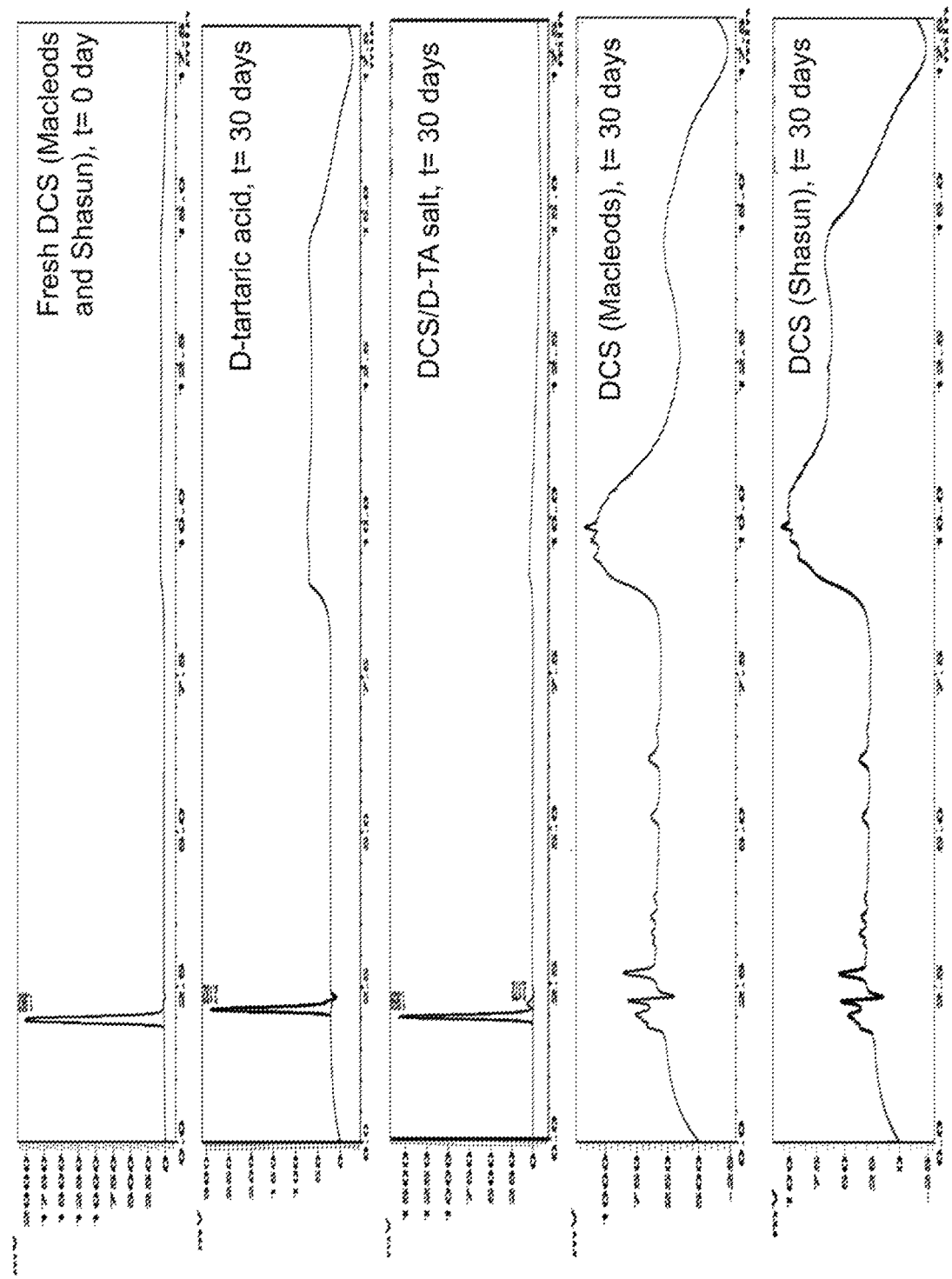
FIG. 39 shows the HPLC analysis of (1) fresh D-cycloserine from Macleods Pharmaceuticals Ltd. and Strides Shasun Ltd. (t=0 day), and (2) D-tartaric acid (3) D-cycloserine D-tartrate (2:1) salt form, (4) D-cycloserine from Macleods Pharmaceuticals Ltd. and (5) D-cycloserine from Strides Shasun Ltd. kept at 40/75% RH for 30 days, as described in Example 5. Only the D-cycloserine D-tartrate (2:1) salt is stable under the condition.

D-cycloserine from Strides Shasun Ltd. and Macleods Pharmaceuticals Ltd., D-tartaric acid, D-cycloserine D-tartrate (2:1) salt form, and fresh D-cycloserine from Macleods Pharmaceuticals Ltd. and Strides Shasun Ltd. (t=0 day) were also analyzed by HPLC, as shown in FIG. 39. Only D-tartaric acid, D-cycloserine D-tartrate (2:1) salt form is stable.

Figure 40:
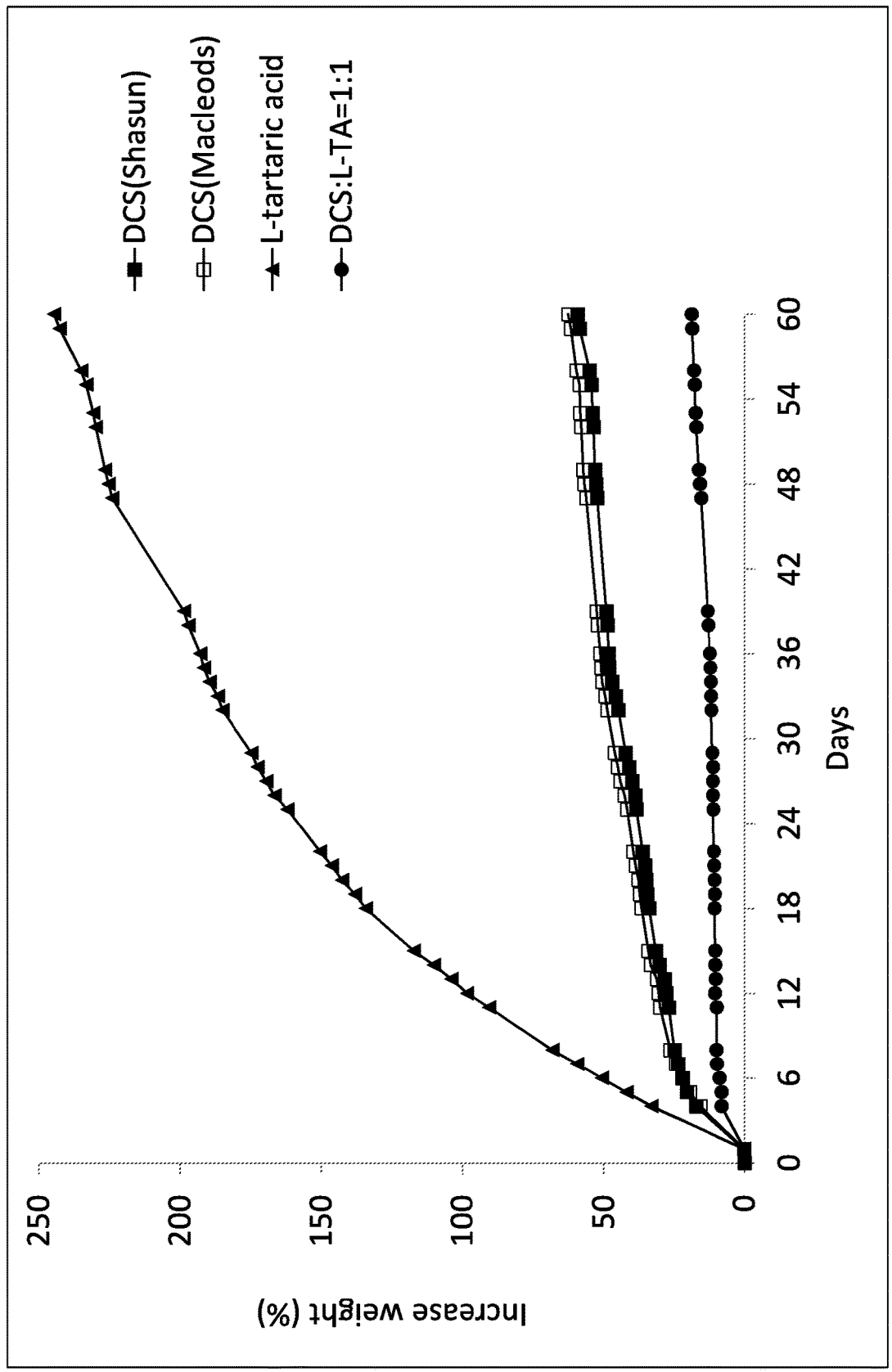
FIG. 40 shows the result of the hygroscopicity test of D-cycloserine from Strides Shasun Ltd. (top curve), D-cycloserine from Macleods Pharmaceuticals Ltd., L-tartaric acid, and D-cycloserine L-tartrate (1:1) salt form (bottom curve) at room temperature/95% RH in an open system for 60 days, as described in Example 6. D-cycloserine L-tartrate (1:1) salt form was not hygroscopic while the others are.
Figure 41:
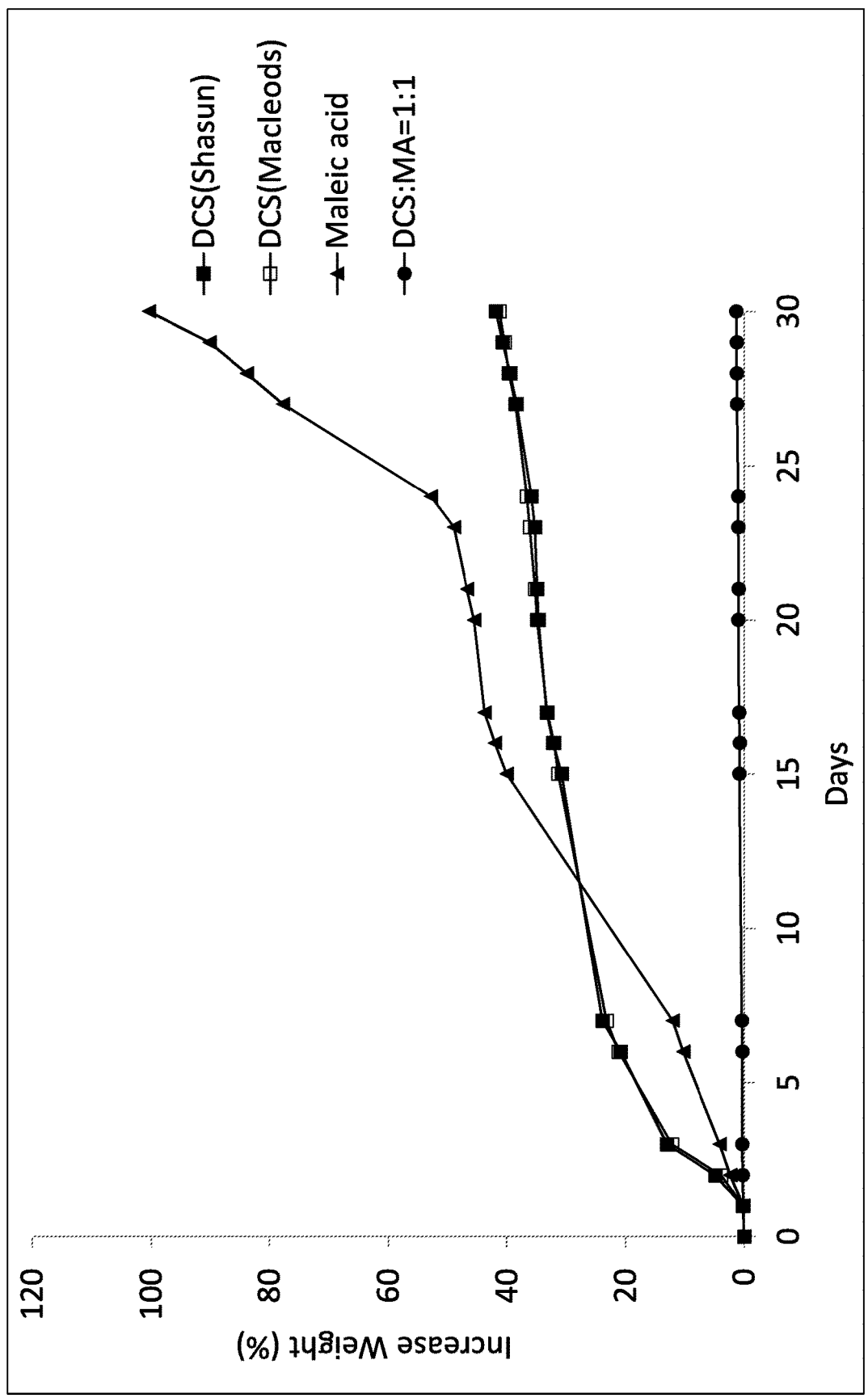
FIG. 41 shows the result of the hygroscopicity test of D-cycloserine from Strides Shasun Ltd. (top curve), D-cycloserine from Macleods Pharmaceuticals Ltd., maleic acid and D-cycloserine maleate (1:1) salt form (bottom curve) at room temperature/95% RH in an open system for 30 days, as described in Example 6. D-cycloserine L-tartrate (1:1) salt form was not hygroscopic while the others are.
Figure 42:
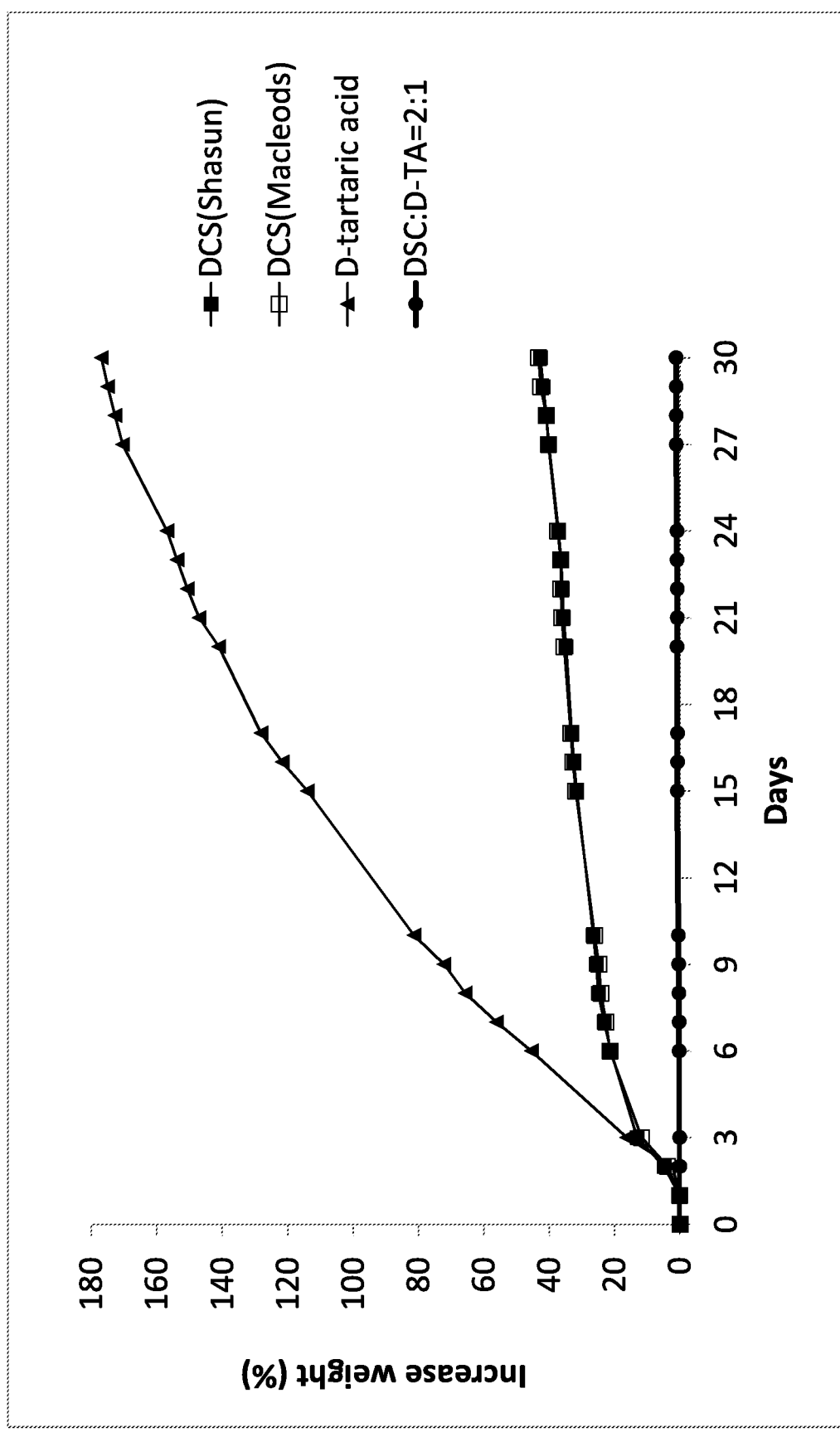
FIG. 42 shows the result of the hygroscopicity test of D-cycloserine from Strides Shasun Ltd. (top curve), D-cycloserine from Macleods Pharmaceuticals Ltd., D-tartaric acid, and D-cycloserine D-tartrate (2:1) salt form (bottom curve) at room temperature/95% RH in an open system for 30 days, as described in Example 6. D-cycloserine D-tartrate (2:1) salt form was not hygroscopic while the others are.

Example 6: Hygroscopicity Test of D-cycloserine and D-cycloserine Salt Form at Room Temperature/95% RH with an Open System for Stress Stability Study 200 mg of D-cycloserine from Strides Shasun Ltd. and Macleods Pharmaceuticals Ltd., L-tartaric acid, maleic acid, D-tartaric acid, D-cycloserine L-tartrate (1:1) salt form D-cycloserine maleate (1:1) salt form and D-cycloserine D-tartrate (2:1) salt form were each put into a colorless glass bottle and kept at room temperature/95% RH in an open system (i.e. the bottle was open) for a stress study. Compounds with bottle were weighed every day. The result indicated that D-cycloserine from Strides Shasun Ltd. and Macleods Pharmaceuticals Ltd. absorbed 59.2% and 62.5% at the 60$^{th}$ day, respectively (as shown in FIG. 40); they absorbed 41.9% and 41.3% of water at the 30$^{th}$ day, respectively (as shown in FIG. 41).); and they absorbed 42.7% and 43.3% of water at the 30$^{th}$ day, respectively (as shown in FIG. 42). L-tartaric acid and D-cycloserine L-tartrate salt form absorbed 244.6 and 18.9% of water at the 60$^{th}$ day, respectively (as shown in FIG. 40). Maleic acid and D-cycloserine Maleate salt form absorbed 100.4 and 1.3% of water at the 30$^{th}$ day, respectively (as shown in FIG. 41). D-tartaric acid and D-cycloserine D-tartrate salt form absorbed 177.0 and 1.3% of water at the 30$^{th}$ day, respectively (as shown in FIG. 42). This suggested that the D-cycloserine L-tartrate (1:1) salt form, D-cycloserine maleate (1:1) salt form and D-cycloserine D-tartrate (2:1) salt form are much less hygroscopic than D-cycloserine and the carboxylic acids alone.

EQUIVALENTS AND SCOPE

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A salt of formula [A][B],
wherein [A] is a cation form of a cycloserine compound; and
[B] is an anion form of a compound of formula (I):

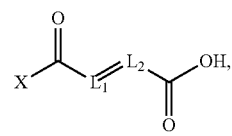

in which
X is —NH$_2$ or —OH;
each of L$_1$ and L$_2$, independently, is C$_{1-6}$ alkylene, C$_{2-6}$ alkenylene, or C$_{2-6}$ alkynylene, or one of L$_1$ and L$_2$ is N, O, or S, and the other one is C$_{1-6}$ alkylene, C$_{2-6}$ alkenylene, or C$_{2-6}$ alkynylene, as valency permits;
===== is either a single or double bond; and
wherein the ratio of [A] and [B] in the salt ranges from 5:1 to 1:5.

2. The salt of claim 1, wherein the cycloserine compound is of formula:

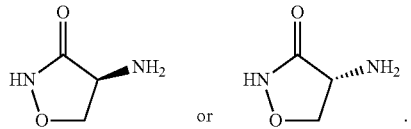 [SMILES: N[C@H]1CONC1=O ; N[C@@H]1CONC1=O]

3. The salt of claim 2, wherein the compound of formula (I) is of formula:

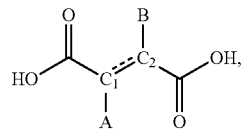

wherein:
each instance of A and B, independently, is —NH$_2$, —OH, or —H;
and C$_1$═══C$_2$ is —C$_1$-C$_2$- or —C$_2$═C$_1$-.

4. The salt of claim 3, wherein the compound of formula (Ia) is of formula:

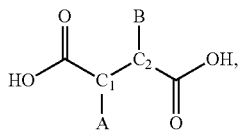
(Ib)

wherein
each instance of A and B, independently, is —OH or —H.

5. A salt of formula [A][B],
wherein:
[A] is a cation form of a cycloserine compound; and
[B] is an anion form of a compound selected from the group consisting of:

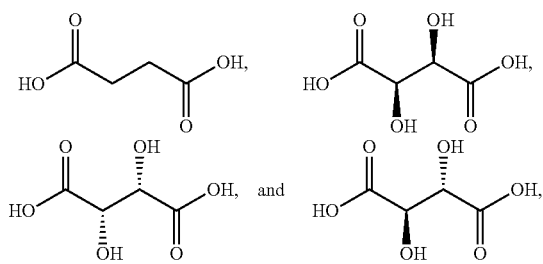

and
wherein the ratio between [A] and [B] ranges from 5:1 to 1:1.

6. The salt of claim 5, wherein [B] is an anion form of a compound of formula

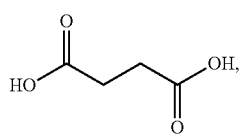

and the ratio between [A] and [B] is 4:1.

7. The salt of claim 5, wherein [B] is an anion form of a compound of formula

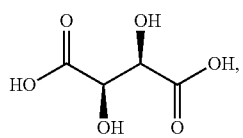

and the ratio between [A] and [B] is 2:1.

8. The salt of claim 5, wherein [B] is an anion form of a compound of formula

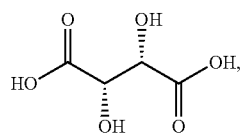

and the ratio between [A] and [B] is 1:1.

9. A salt of formula [A][B],
wherein [A] is a cation form of a cycloserine compound; and
[B] is an anion form of a compound of formula (Ic):

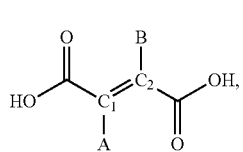
(Ic)

wherein A and B, independently, is —OH or —H; and
wherein the ratio between [A] and [B] ranges from 5:1 to 1:1.

10. The salt of claim 9, wherein the compound of formula (Ic) is selected from the group consisting of

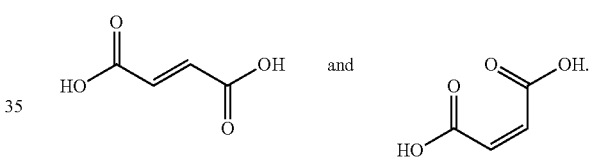

11. The salt of claim 10, wherein the compound of formula (Ic) is

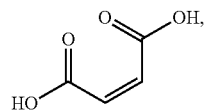

and the ratio between [A] and [B] is 1:1.

12. A composition comprising the salt of claim 5 and a carrier.

13. A composition comprising the salt of claim 9 and a carrier.

14. The composition of claim 12, wherein the composition is a pharmaceutical composition, a nutraceutical composition, a health food, or a medical food.

15. The composition of claim 13, wherein the composition is a pharmaceutical composition, a nutraceutical composition, a health food, or a medical food.

* * * * *